(12) United States Patent
Farrell et al.

(10) Patent No.: US 11,788,149 B2
(45) Date of Patent: Oct. 17, 2023

(54) SINGLE-STRANDED OLIGONUCLEOTIDE PROBES FOR CHROMOSOME OR GENE COPY ENUMERATION

(71) Applicant: Ventana Medical Systems, Inc., Tucson, AZ (US)

(72) Inventors: Michael Farrell, Tucson, AZ (US); Antony Hubbard, Tucson, AZ (US); Donald Johnson, Tucson, AZ (US); Brian Kelly, Tucson, AZ (US); Taylor Shingler, Tucson, AZ (US); Lei Tang, Oro Valley, AZ (US); Wenjun Zhang, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 318 days.

(21) Appl. No.: 16/879,228

(22) Filed: May 20, 2020

(65) Prior Publication Data

US 2021/0002726 A1 Jan. 7, 2021

Related U.S. Application Data

(60) Division of application No. 15/242,471, filed on Aug. 19, 2016, now Pat. No. 10,752,955, which is a continuation of application No. PCT/EP2015/053555, filed on Feb. 20, 2015.

(60) Provisional application No. 62/094,543, filed on Dec. 19, 2014, provisional application No. 61/943,196, filed on Feb. 21, 2014.

(51) Int. Cl.
*C12Q 1/6886* (2018.01)
*C12Q 1/6841* (2018.01)

(52) U.S. Cl.
CPC ......... *C12Q 1/6886* (2013.01); *C12Q 1/6841* (2013.01); *C12Q 2600/156* (2013.01); *C12Q 2600/158* (2013.01)

(58) Field of Classification Search
CPC ............ C12Q 1/68; C07H 21/00; C12P 19/34
See application file for complete search history.

(56) References Cited

U.S. PATENT DOCUMENTS

| | | | |
|---|---|---|---|
| 5,447,841 | A | 9/1995 | Gray et al. |
| 5,750,340 | A | 5/1998 | Kim et al. |
| 7,807,356 | B2 | 10/2010 | Sampson et al. |
| 8,445,206 | B2 | 5/2013 | Bergmann et al. |
| 2002/0160401 | A1 | 10/2002 | Nozaki et al. |
| 2003/0017491 | A1 | 1/2003 | Shi |
| 2007/0218480 | A1 | 9/2007 | Katz et al. |
| 2008/0050748 | A1 | 2/2008 | Cohen et al. |
| 2008/0299555 | A1 | 12/2008 | Nitta et al. |
| 2010/0136549 | A1 | 6/2010 | Christiansen et al. |
| 2013/0338023 | A1 | 12/2013 | Willard-Gallo et al. |
| 2014/0222443 | A1 | 8/2014 | Danenberg et al. |
| 2017/0212983 | A1 | 7/2017 | Cai et al. |

FOREIGN PATENT DOCUMENTS

| | | |
|---|---|---|
| EP | 0511750 A1 | 11/1992 |
| JP | 2002-516667 | 6/2002 |
| JP | 2002296279 | 10/2002 |
| JP | 2005-503158 A | 2/2005 |
| JP | 2007-319051 A | 12/2007 |
| JP | 2008298654 | 12/2008 |
| WO | 99/61665 A2 | 12/1999 |
| WO | 0157277 A2 | 8/2001 |
| WO | 03025127 A2 | 3/2003 |

OTHER PUBLICATIONS

Meyne et al., Human chromosome-specific repetitive DNA probes: Targeting in situ hybridization to chromosome 17 with a 42-base-pair alphoid DNA oligomer. Genomics 4(4) : 472-478 (Year: 1989).*

An, et al., Generation of digoxigenin-labelled double-stranded andsingle-stranded probes using the polymerase chain reaction. Molecular and Cellular Cell. Probes 6(3) :193-200 (Year: 1992).

Bergstrom Lucas et al., Designing Custom Oligo FISH Probes for the Detection of Chromosomal Rearrangements in FFPE Tissue; (Abstract/Program #3217F), Presented at the 63rd Annual Meeting of The American Society of Human Genetics, Oct. 25, 2013 in Boston, Massachusetts, 1 page.

Cox, et al., Detection of mRNAs in Sea Urchin Embryos by Situ Hybridization Using Asymmetric RNA Probes Developmental Biology 101(2): 485-502 (Year: 1984).

Dal Lago, et al., Correction for chromosome-17 is critical for the determination of true Her-2/neu geneamplification status in breast cancer. Mo. Cancer Ther.5 (10) :2572 (year: 2006).

FDA, Summary of Safety and Effectiveness Data (SSED), FDA Summary of Safety and Effectiveness Data, 2011, 1-42, PMA No. P100027.

Gao, F. et al., Bright-Field HER2 Dual In Situ Hybridization (DISH) Assay vs Fluorescence In Situ Hybridization (FISH), Am. J. Clin. Pathol., 2014, 102-110, 141 (1).

Grogan et al., Ventana Inform HER2 Dual ISH DNA Probe Cocktail Assay, Interpretation Guide, Jan. 1, 2010, Whole Document, unknown, Roche Diagnostics Gmbh, Mannheim.

Gruver, Aaron M., "Out of the darkness and into the light: bright field in situ hybridisation for delineation of ERBB2 (HER2) status in breast carcinoma". Journal of Clinical Pathology, 2010, 210-219, 63(3).

Haar et al., "A rapid FISH technique for quantitative microscopy", Biotechniques 17(2) : 346-352 (year: 1994).

(Continued)

Primary Examiner — Ethan C Whisenant
(74) Attorney, Agent, or Firm — Ventana Medical Systems, Inc.

(57) ABSTRACT

Single-stranded oligonucleotide probes, systems, kits and methods for chromosome enumeration, gene copy enumeration, or tissue diagnostics. The probes are particularly suited for detecting gene amplification, deletion, or rearrangement in tissue samples in a single, dual, or multiplexed assay. The probes exhibit improved performance compared to industry leading dual-stranded probes; particularly in terms of the rate of hybridization.

12 Claims, 25 Drawing Sheets

Specification includes a Sequence Listing.

(56) References Cited

OTHER PUBLICATIONS

Hannon, et al., Synthesis of PCR-Derived, Single-Stranded DNA Probes Suitable for in Situ Hybridization. Analytical Biochemistry 212(2):421-427, (Year: 1993).

Hicks et al, Assessment of the HER2 status in breast cancer by fluorescence in situ hybriization: a technical review with interpretive guidelines, Human Pathology, 2005, pp. 250-261, vol. 36.

IPEA, International Preliminary Reporton Patentability, International Preliminary Report on Patentability, dated Sep. 8, 2015. 1-17, N/A.

ISA, International Search Report, International Search Report, dated May 8, 2015, 1-7, N/A, WO.

ISA, ISA written Opinion, Written Opinion, dated May 11, 2015, 1-15, N/A.

Kourilsky, et al., Hybridization on filters with competitor DNA in the liquid phase in a standard and a micro-assay. Biochimie 56(9), 1215-1221 (Year: 1974).

Laakso et al., "Dual-colour chromogenic in situ hybridization for testing of HER-2 oncogene amplification in archival breast tumours", J. of Pathology 210: 2-9 (year: 2006).

Lai, E Tal, Anatomic Pathology, HER-2 Testing in Breast Cancer Using Immunohistochemical Analysis and Fluorescence In Situ Hybridization, 2004, pp. 631-636, vol. 121.

Lebeau, et al., HER-2/neu Analysis in Archival Tissue Samples of Human Breast Cancer: Comparison of Immunohistochemistry and Fluorescence In Situ Hybridization. Journal of Clinical Oncology; 19 (2): 354 (Year: 1985).

Lewis, et al., In Situ Hybridization HistochemistryWith Synthetic Oligonucleotides: Strategies and Methods . Peptides 6 Suoppl. 2: 75-87 (Year: 1985).

Lichstein, et al., Studies of the Effect of Sodium Azide on Microbic Growth and Respiration, Journal of Bacteriology, 1944, 47(3), 221-230. (Year: 1944).

Martin, et al., Synergism between hydrogen peroxide and seventeenacids against six bacterial strains. Journal of Applied Microbiology 2012, 113, 578-590 (Year: 2012).

Matthiesen, et al, Plos One, Fast and Non-Toxic In Situ Hybridization without Blocking of Repetitive Sequences, 2012, pp. e40675, pp. 1-8, vol. 7.

Mistry, et al., Image Similarity based on Joint Entropy (Joint Histogram). Proc. International Conference on advances in Engineering and Technology 2013 (year: 2013).

Modern Media, (2012), pp. 49-57 / in JP language, vol. 58 No. 2.

Moelans, et al, Breast Cancer Research, Absence of chromosome 17 polysomy in breast cancer:, 2010, pp. 1-7, vol. 120.

Navin, N. et al., Genome analysis: Prober: oligonucleotide FISH probe design software, Bioinformatics, 2006, pp. 2437-2438, vol. 22, No. 19.

Nederlof, et al, Cytometry, Three-Color Fluorescense in Situ Hybridization for the Simultaneous Detection of Multiple Nucleic Acid Sequences, 1989, pp. 20-27, 10.

Nitta, H. et al., Development of automated brightfield double In Situ hybridization (BDISH) application for HER2 gene and chromosome 17 centromere (CEN 17) for breast carcinomas and an assay performance comparison to manual dual color HER2 fluorescence, Diagnostic Pathology, BioMed Central, (2008), 1-12, vol. 3, No. 41.

O'Keefe, et al, Human Molecular Genetics, Oligonucleotide probes for alpha satellite DNA variants can distinguish homologous chromosomes by FISH, 1996, pp. 1793-1799, vol. 5 No. 11.

Pai, et al., Arch pathol lab Med, Utility of Alternate Noncentromeric Chromosome 17 Ref Probe for Human Epidermal Growth Factor Receptor Fluorescence, 2018, pp. 626-633, vol. 142.

Pauletti, et al., Assessment of Methods for Tissue-Based Detection of theHER-2/neu Alteration in Human Breast Cancer: A DirectComparison of Fluorescence In Situ Hybridization andImmunohistochemistry. Journal of Clinical Oncology: 18 (21) : 3651 (Year: 2000).

Press, et al., Evaluation of HER-2/neu Gene Amplification and Overexpression: Comparison of Frequently Used Assay Methods in a Molecularly Characterized Cohort of Breast Cancer Specimens. J. of Clinmical Oncology 20(14): 3095 (Year: 2002.

Ross, et al., Molecularand Cellular Proteomics, Targeted Therapy in Breast Cancer, 2004, pp. 379-398, 3.4.

Taneja, et al., Use of Oligodeoxynucleotide Probes for quantitative in situ hybridization to actin mRNA. Analytical Biochemistry 166:389 (Year: 1987).

Van Dekken et al., "Targeted cytogenetic analysis of gastric tumors by in situ hybridization with a set of chromosome-specific DNA probes", Cancer 66 : 491-497 (year: 1990).

Vera-Roman, et al, Arch Pathol Lab Med, Comparative Assays for the HER-2/neu Oncogene Status in Breast Cancer, 2004, pp. 627-633, vol. 128.

Wang, et al, Anatomic Pathology, Assessment of HER-2/neu Status in Breast Cancer, 2001, pp. 495-503, vol. 116.

Wang, G. et al, "HIV integration site selection: Analysis by massively parallel pyrosequencing reveals association with epigenetic modifications", Genome Research, 2007, 1186-1194, 17(8).

Warburton et al., Interhomologue Sequence Variation of Alpha Satellite DNA from Human Chromosome 17: Evidence for Concerted Evolution Along Haplotypic Lineages, Journal of Molecular Evolution, 1995, pp. 1006-1015, 41.

Waye, J. et al, Structure, Organization, and Sequence of Alpha Satellite DNA from Human Chromosome 17: Evidence for Evolution by Unequal Crossing-Over and an Ancestral Pentamer Repeat Shared with the Human X Chromosome, Molecular and Cellular Biology, (1986), pp. 3156-3165, vol. 6.

Willard, H. F., Chromosome-Specific Organization of Human Alpha Satellite DNA, Am J Hum Genet, 1985, pp. 524-532, 37.

Willard, H. F., et al., Molecular Organization and Haplotype Analysis of Centromeric DNA from Human Chromosome 17: Implications for Linkage in Neurofibromatosis, Genomics, 1987, pp. 368-373, 1.

Willard, H. F., Evolution of alpha satellite, Current Opinion in Genetics and Development, 1991, pp. 509-514, 1.

Wolff et al, 2007, "American Society of Clinical Oncology/College of American Pathologists Guideline Recommendations for Human Epidermal Growth Factor Receptor 2 Testing in Breast Cancer", Jounal of Clinical Oncology, 25(1):118-145.

Yamada et al., Visualization of fine-scale genomic structure by oligonucleotide-based high-resolution FISH, Cytogenetic and Genome Research, vol. 132, Issue 4, pp. 248-254 (e-published Dec. 18, 2010).

* cited by examiner

5'-T[DNP]CTCGTCTCGGCCCCCGACCT
[DNP]GCGTCCTGGGCCCGCAGGGG[DNP]
AGTCCTGCCCCATGCTCC**CG[DNP]
GG**CGGGGCCGCCCTGTGCCC[DNP]T-3'

[AminoC6+Dig]TATTTTTATTTT[Am~Uni+Dig]AATTCGTTGGA
AACGGGATAATTTCAGCTGACTAAACAGAAGCAGTCTCAGAAT
CTTCTTTGTGATGTTTGCATTCAAA

| CHR17 oligos | Length | # hits on CHR17 | # off-target hits | | |
|---|---|---|---|---|---|
| | nt | >85% identity | >85% identity | Continuous stretch | chromosomes |
| M1.1 | 79 | 23 | 5 | >=78nt | 1, 3, 20 |
| M11.2 | 71 | 17 | 8 | 71nt | X, 1 |
| M12.1 | 80 | 7 | 7 | 80nt | X |
| M13.1 | 80 | 19 | 18 | >=78nt | 1, 9, 20 |
| M16.1 | 80 | 19 | 16 | 80 nt | 1 |
| M16.2 | 80 | 16 | 11 | 80nt | 1 |
| M2.1 | 79 | 21 | 33 | 79nt | 1 |
| M2.2 | 79 | 18 | 14 | >=72nt | X |
| M3.1 | 79 | 23 | 16 | >=70nt | 22, 20, X, 2, 14, 11, 21, 3 |
| M5.1 | 83 | 25 | 33 | >=71nt | 1 |
| M5.2 | 87 | 16 | 22 | >=76nt | 1, 3, 16 |
| M8.2 | 71 | 19 | 38 | >=66nt | 1, X, 14 |
| M9.1 | 58 | 19 | 20 | >=57nt | 1, X, 11, 12 |
| M9.2 | 65 | 17 | 7 | >=58nt | 1, X, 11, 22 |

FIG. 15

SEQUENCE LISTING

```
<160> NUMBER OF SEQ ID NOS: 16

<210> SEQ ID NO 1
<211> LENGTH: 82
<212> TYPE: DNA
<213> ORGANISM: Homo sapiens

<400> SEQUENCE: 1
tctcgtctcg gcccccgacc tgcgtcctgg gcccgcaggg gagtcctgcc ccatgctccc    60
gggcggggcc gccctgtgcc ct                                             82

<210> SEQ ID NO 2
<211> LENGTH: 91
<212> TYPE: DNA
<213> ORGANISM: Homo sapiens

<400> SEQUENCE: 2
tatttttatt ttaattcgtt ggaaacggga taatttcagc tgactaaaca gaagcagtct    60
cagaatcttc tttgtgatgt ttgcattcaa a                                   91

<210> SEQ ID NO 3
<211> LENGTH: 79
```

```
<212> TYPE: DNA
<213> ORGANISM: Homo sapiens

<400> SEQUENCE: 3
aattcgttgg aaacgggata atttcagctg actaaacaga agcagtctca gaatcttctt      60
tgtgatgttt gcattcaaa                                                   79

<210> SEQ ID NO 4
<211> LENGTH: 79
<212> TYPE: DNA
<213> ORGANISM: Homo sapiens

<400> SEQUENCE: 4
cttcgttcga aacgggtata tcttcacatg ccatctagac agaagcatcc tcagaagctt      60
ctctgtgatg actgcattc                                                   79

<210> SEQ ID NO 5
<211> LENGTH: 79
<212> TYPE: DNA
<213> ORGANISM: Homo sapiens

<400> SEQUENCE: 5
tgaactctcc ttttgagagc gcagttttga aactctcttt ctgtggcatc tgcaagggga      60
catgtagacc tctttgaag                                                   79

<210> SEQ ID NO 6
<211> LENGTH: 79
<212> TYPE: DNA
<213> ORGANISM: Homo sapiens

<400> SEQUENCE: 6
tttcgttgga aacggaatca tcttcacata aaaactacac agatgcattc tcaggaactt      60
tttggtgatg tttgtattc                                                   79

<210> SEQ ID NO 7
<211> LENGTH: 83
<212> TYPE: DNA
<213> ORGANISM: Homo sapiens

<400> SEQUENCE: 7
cctatggtag taagggaat agcttcatag aaaaactaga cagaagcatt ctcagaaaat       60
actttgtgat gattgagttt aac                                              83

<210> SEQ ID NO 8
<211> LENGTH: 87
<212> TYPE: DNA
<213> ORGANISM: Homo sapiens

<400> SEQUENCE: 8
cacagagctg aacattcctt tggatggagc aggtttgaga cactctttt gtacaatcta       60 caagtggata tttggacctc tctgagg                                          87

<210> SEQ ID NO 9
<211> LENGTH: 71
<212> TYPE: DNA
<213> ORGANISM: Homo sapiens

<400> SEQUENCE: 9
gtttcacatt gcttttcata gagtagttct gaaacatgct tttcgtagtg tctacaagtg      60
```
gacatttgga g                                                              71

<210> SEQ ID NO 10
<211> LENGTH: 58
<212> TYPE: DNA
<213> ORGANISM: Homo sapiens

<400> SEQUENCE: 10
cctgtggtgg aaaacgaatt atcgtcacgt aaaaactaga gagaagcatt gtcagaaa           58

<210> SEQ ID NO 11
<211> LENGTH: 65
<212> TYPE: DNA
<213> ORGANISM: Homo sapiens

<400> SEQUENCE: 11
tgcattcaac tcacagagtt gaaggttcct tttcaaagag cagtttccaa tcactctttg         60
tgtgg                                                                     65

<210> SEQ ID NO 12
<211> LENGTH: 71
<212> TYPE: DNA
<213> ORGANISM: Homo sapiens

<400> SEQUENCE: 12 cattccctttt gacagagcag tttggaaact ctctttgtgt agaatctgca agtggagata        60
tggaccgctt t                                                              71

<210> SEQ ID NO 13
<211> LENGTH: 80
<212> TYPE: DNA
<213> ORGANISM: Homo sapiens

<400> SEQUENCE: 13
cctatggtag taaaggaaat agcttcatat aaaagctaga cagtagcatt cacagaaaac         60
tcttggtgac gactgagttt                                                     80

<210> SEQ ID NO 14
<211> LENGTH: 80
<212> TYPE: DNA
<213> ORGANISM: Homo sapiens

<400> SEQUENCE: 14
atttcgttgg aaacgggata aaccgcacag aactaaacag aagcattctc agaaccttct         60
tcgtgatgtt tgcattcaac                                                     80

<210> SEQ ID NO 15
<211> LENGTH: 80
<212> TYPE: DNA
<213> ORGANISM: Homo sapiens

<400> SEQUENCE: 15
cgtagtaaag gaaataactt cctataaaaa gaagacagaa gctttctcag aaaattcttt         60
gggatgattg agttgaactc                                                     80

<210> SEQ ID NO 16
<211> LENGTH: 79
<212> TYPE: DNA
<213> ORGANISM: Homo sapiens

```
<400> SEQUENCE: 16
acagagctga gcattccttg cgatgtagca gtttagaaac acactttctg cagaatctgc     60
aattgcatat ttggacctt                                                  79
```

SINGLE-STRANDED OLIGONUCLEOTIDE PROBES FOR CHROMOSOME OR GENE COPY ENUMERATION

CROSS-REFERENCE TO RELATED APPLICATIONS

This patent application is a continuation of International Patent Application No. PCT/EP2015/053555 filed Feb. 20, 2015, which claims priority to and the benefit of U.S. Provisional Patent Application No. 62/094,543 filed Dec. 19, 2014 and U.S. Provisional Patent Application No. 61/943,196 filed Feb. 21, 2014. Each patent application is incorporated herein by reference as if set forth in its entirety.

SEQUENCE LISTING

The sequence listing entitled "P32027_sequence_listing_ST25.txt," which was created on 19 Aug. 2016 and has a size of 3,901 bytes, filed herewith, is incorporated-by-reference.

FIELD

This disclosure relates to oligonucleotide probes, systems, kits, and methods for using said probes and systems for chromosome enumeration, for detection of nucleic acid target sequences (e.g., genomic DNA or RNA), for gene copy number enumeration, and/or for tissue diagnostics.

BACKGROUND

Probes have been developed for a variety of diagnostic and research purposes. Hybridization of chromosome or gene-specific probes has made possible detection of chromosomal abnormalities associated with numerous diseases and syndromes, including constitutive genetic anomalies (such as microdeletion syndromes, chromosome translocations, gene amplification and aneuploidy syndromes), neoplastic diseases, as well as pathogen infections. Detection of genetic changes in these regions can provide diagnostic and prognostic information for patients and in some cases, inform treatment decisions.

Dual detection and enumeration of human chromosome 17 (CHR17) and human epidermal growth factor receptor 2 (HER2) is important for the selection of appropriate patients for HER2 targeted therapy in breast cancer (Miff A C, et al., *J Clin Oncol* 2007, 25:118-145; Gruver A M, et al., *J Pathol* 2010 March; 63(3):210-9), but existing probes that may be used for such dual detection and enumeration are known for requiring long assay times to obtain specific and sensitive detection.

Double-stranded CHR17 centromere probes are typically generated from the p17H8 plasmid sequence, which is directed to human CHR17's alpha satellite. The alpha satellite of human CHR17 contains a ~2,700 base pair higher order repeat unit that consists of 16 monomers and is present in 500 to 1,000 copies per CHR17 (Waye J S, et al., *Molecular and Cellular Biology*, September 1986, p. 3156-3165). Double-stranded HER2 probes are typically generated from bacterial artificial chromosomes (BACs) and span the HER2 gene (Dal Lago L, et al., *Mol Cancer Ther* 2006, 5:2572-2579; Gruver A M, et al., *J Clin Pathol* 2010 March; 63(3):210-9). These double-stranded probes have repetitive sequences that are common to centromere regions of other human chromosomes. Consequently, a significant drawback to these probes is the noise-generating repetitive elements. That is, probes to the centromere regions typically have significant cross-reactivity to other chromosome centromeres. As such, blocking DNA has been required to be used in conjunction with these probes to reduce non-specific binding (See Pinkel and Gray, U.S. Pat. No. 5,447,841). Assays employing these probes require extensive hybridization time to achieve sufficient hybridization because of their double-stranded nature and the required competition with the blocking DNA, e.g., about 6 to 18 hours. This time consuming step reflects low hybridization efficiency, in part due to self-hybridization of the double-stranded probe and in part because of the competition with the blocking DNA. Libraries of BAC probes are also cumbersome to generate and maintain, laborious to purify, and are prone to contamination. The benchmark and ground-breaking assay using this technology was disclosed by Nitta et al. in 2008 and is commercially available as the INFORM HER2 Dual ISH DNA Probe Cocktail, Ventana Medical Systems, Catalog Number: 780-4422 (Nitta et al. *Diagnostic Pathology*, 3:41, 2008).

Recently, Matthiesen and Hansen (Matthiesen S H, et al., *PLoS One*, 2012; 7(7), 2012) claimed that with no change in the HER2 and CHR17 probe configuration, substitution of ethylene carbonate (EC) for formamide in the hybridization buffer reduced FISH hybridization time and requires no blocking DNA. The HER2 IQFISH pharmDx™ assay (Dako) was introduced to the market based on this technology. While a useful technique, fluorescence in situ hybridization (FISH) has its drawbacks. Implementation of conventional FISH requires a dedicated fluorescence imaging system and well-trained personnel with specific expertise, making this system incompatible with some clinical workflows. Furthermore, when compared to bright-field in situ hybridization (ISH) approaches, FISH studies provide relatively limited morphological assessment of overall histology, lack stability of the fluorescent detection signal(s) over time, and have a higher overall cost of testing.

In an effort to alleviate drawbacks associated with clone-based probes, investigators have proposed the use of "specific primers" to generate probes from genomic DNA (Navin et al., *Bioinformatics* 22:2437-2438 (2006)). However, this process is cumbersome and time consuming in that it requires multiple specific amplification reactions and downstream processing with upfront hands-on time (See also Yamada et al., *Cytogenet Genome Res.* 1-7 (2010)).

For some applications, the use of single-stranded probes has a distinct advantage over the use of double-stranded probes. For example, single-stranded probes generally have higher sensitivity than double-stranded probes because a proportion of the denatured double-stranded probe renatures to form probe homoduplexes, thus preventing their capture of genomic targets in the test samples (Taneja K et al., *Anal Biochem*, 166, 389-398 (1987), Lewis M E, et al., Peptides, 6 Suppl 2:75-87 (1985); Strachan T, Read A P, Human Molecular Genetics. 2nd edition. New York: Wiley-Liss (1999); Kourilsky P, et al., *Biochimie*, 56(9):1215-21 (1974)). Several laboratories have reported that single-stranded probes provide higher hybridization sensitivity than double-stranded probes (An SF, et al., *Mol Cell Probes*, 6(3)193-200 (1992); Hannon K, et al., *Anal Biochem*, 212 (2):421-7 (1993); Cox K H, et al., *Dev Biol.*, 101(2):485-502 (1984)).

Synthetic single-stranded oligonucleotide probes have been used to detect genomic targets, mostly for FISH. For example, Bergstrom et al., Designing Custom Oligo FISH Probes for the Detection of Chromosomal Rearrangements in FFPE Tissues, *American Society of Human Genetics* 2073

*Meeting* (2013) reported SureFISH probes comprising thousands of unique, long single-stranded oligonucleotides with fluorescence labels. The oligonucleotide sequences tile across the targeted chromosomal region of translocation breakpoints for the detection of chromosomal rearrangements. Although Bergstrom discloses single-stranded probes, the probes were not directed to CHR17 and the Bergstrom reference does not appear to provide any solutions to the difficulties associated with CHR17 probes, such as specificity and robustness to detect CHR17 polymorphisms in a human population. Also, the Bergstrom reference does not disclose assays (and probes) for gene copy number enumeration wherein a target probe and a reference probe are used in combination to calculate a target gene to reference chromosome ratio.

The use of single-stranded oligonucleotide probes for genomic targets has been extremely limited. For example, U.S. Pat. No. 8,445,206 (Bergmann et al., 2012) describes a set of at least 100 single-stranded oligonucleotide probes directed against (or complementary to) portions of the HER2 gene. The disclosure appears to be limited to detection of the HER2 gene target without a reference probe (e.g., CHR17), which is useful for gene copy number assessment as the HER2/CHR17 ratio is diagnostically important as evidenced from the teachings of Wolff A C, et al., *J Clin Oncol* 2007, 25:118-145.

Comparative genome hybridization (CGH) assays may be used for providing information on the relative copy number of one sample (such as a tumor sample) compared to another (such as a reference sample, for example a non-tumor cell or tissue sample). Thus, CGH may be used for determining whether genomic DNA copy number of a target nucleic acid is increased or decreased as compared to the reference sample. However, CGH does not provide information as to the exact number of copies of a particular genomic DNA or chromosomal region.

For genomic labeling of CHR17, a previous 42-mer oligonucleotide derived from p17H8 was demonstrated to be specific to CHR17. But, because of significant differences in the sizes of the 42-mer CHR17 probe and the preferred oligomeric HER2 probes (ranging from about 100 bp to about 400 bp) disclosed herein, the dual HER2-CHR17 ISH assay required a lengthy procedure to sequentially detect HER2 and CHR17 signals under different stringency wash temperatures (72° C. for HER2 and 59° C. for CHR17). Importantly, dual ISH experiments using the 42-mer CHR17 probe and single-stranded HER2 probes of a similar size did not resolve the incompatibility of the probe sets (See FIG. 14A-D and Example 2). Further, even if the incompatibility between the 42-mer CHR17 probe and the single stranded HER2 probes were resolved, a single oligonucleotide probe (e.g., the 42-mer CHR17 probe) specific for only a one monomer of the alpha satellite's 16 monomers as taught by Nitta would not be sufficient to detect CHR17 throughout the human population since each individual human being may carry different combinations of the monomers and their related variants (Waye J S and Willard H F, *NAC* 1986; 14(17); Willard, H. F. et al, 1987, *Genomics*, 1; Warburton, P. E. and Willard, H. F., 1995, *J. Mol. Evol.*, 41). Thus, the 42-mer CHR17 probe as taught by Nitta would not be robust enough across the entire population.

Despite the appeal of the use of a single-stranded CHR17 probe, workers in this field thought it is not possible to make short, single-stranded CHR17 probes that are specific enough to CHR17 (e.g., specific enough to eliminate the need for blocking DNA), and robust enough to sufficiently detect CHR17 throughout the human population. One of the reasons for this understanding is that it was believed that the fundamental repetitive nature of alpha satellite DNA makes the likelihood of finding short oligonucleotides specific enough to CHR17 impossibly improbable. For example, Willard (Willard, H. F., 1985, *Am J Hum Genet*, 37; Willard, H. F., 1991, *Curr Opin Genet Dev.* 1) found sequences of the same monomer in different higher order repeat units that showed a level of similarity approaching 99%. Further, there appear to be a significant number of off-target hits to other chromosomes. For example, bioinformatics research revealed that 14 oligonucleotide sequences derived from plasmid p17H8 (comprising the higher order repeat units in the centromere region of CHR17) had high homology to several other chromosomes (e.g., chromosome 1, X, 11, 9, 20, 22, etc.). Although a number of sequences of each oligonucleotide had high homology (85-100%) to CHR17, there were also many off-target hits. For instance, a representative oligonucleotide (M2.1) had 21 on-target hits but also had 33 hits on chromosome 1; another oligonucleotide (M2.2) had 18 on-target hits but also had 14 hits on chromosome X (See FIG. 15). These results suggest that the centromere region of CHR17 may not contain sufficiently specific sequences for targeting. Indeed, examining the centromere region from a bioinformatics perspective indicates that designing probes uniquely specific to the centromere, which would be capable of providing selective signal without the use of blocking DNA, is not reasonable or expected to be possible.

Another reason that workers in the field expected it was not possible to make short, single-stranded CHR17 probes specific enough to CHR17 (e.g., specific enough to eliminate the need for blocking DNA) is because of the lack of robustness of a single (or a few number of) single-stranded oligonucleotide probe(s). As discussed above, human CHR17-specific alpha satellite contains a higher order repeat unit that consists of 16 monomers, and each individual human being may carry different combinations of these monomers and their related variants (Waye J S and Willard H F, *Molecular and Cellular Biology*, September 1986, p. 3156-3165). A single oligonucleotide probe, e.g. the 42mer described above, or even a few number of oligonucleotides covering a small number of monomers, may not be robust enough to detect CHR17 polymorphism in a human population (Waye J S, Willard H F., *NAC* 1986; 14(17); Willard, H. F. et al, 1987, *Genomics*, 1; Warburton, P. E. and Willard, H. F., 1995, *J. Mol. Evol.*, 41). Indeed, a single CHR17-specific oligonucleotide probe (79mer) did not show equivalent (or better) sensitivity to the p17H8 plasmid derived probe. In particular, when the single 79mer CHR17 oligonucleotide was compared to the commercial probe (p17H8 probe), it was found that it passed (signal intensity $\geq 2$, coverage $\geq 50\%$, and background <2) only 41.5% (113/272) at 1 μg/mL, 1 hr compared to 61.1% (148/242) at 0.75 μg/mL, 6 hr. Accordingly, the Chr17 Oligonucleotide (a single 79mer) failed to show equivalent sensitivity to the commercial probe design.

Another reason that workers in the field expected it was not possible to make short, single-stranded CHR17 probes specific enough for CHR17 was because the making of such oligonucleotide probes is very cumbersome and the manufacturability of such product is heretofore, not readily known. In particular, to span a 1 million bp genomic region with probes hybridizing to at least 60 kb of target, as many as 1200 unique 50-mer oligonucleotide probes may be needed. Manufacturing 1200 unique probes and combining them within a single reagent is difficult, expensive, and breaks new ground from a regulatory perspective.

SUMMARY

A set of 14 unique single-stranded probes that are highly specific for CHR17 and are highly robust enough to account for polymorphisms in a human population were created and synthesized. These single-stranded probes are fully compatible for use for the detection of HER2. In fact, these newly discovered oligonucleotide probes are so highly specific that the inventors were able to eliminate the use of blocking DNA in the assays disclosed herein. Furthermore, it was surprisingly discovered that these oligonucleotide probes have enhanced hybridization efficiency, which requires a significantly reduced hybridization time. These single-stranded oligonucleotide probes to CHR17 also enabled discrete enumerable rounded signals that are superior to those previously available. In particular, the detectable signals contrast to the nick-translation labeled double-stranded probes, which tend to generate signals with a wide range of sizes and shapes.

The single-stranded oligonucleotide probes to CHR17 of the present invention may be used in combination with one or more target probes directed to a target gene of interest. This allows for gene copy enumeration (e.g., determination of the ratio of a target gene to its corresponding chromosome), which may be important for tissue diagnostics. Alterations in DNA copy number are the hallmark of many types of cell proliferative disorders such as cancer. Indeed, some investigators have hypothesized that these are thought to drive some cancer pathogenesis processes. Representative alterations include large chromosomal gains and losses in addition to smaller scale amplifications and deletions. Considering that genomic instability may trigger the activation of oncogenes and/or the silencing of tumor suppressors, mapping regions of genomic aberrations is a useful tool to identify cancer-related genes. Such information—genomic aberrations—may provide useful information relative to diagnosis of cancer or as a prognostic aide. As mentioned above, HER2 is a gene found on CHR17; the present invention also features the use of single-stranded oligonucleotide probes to detect (and enumerate gene copy number) the HER2 gene on CHR17 in combination with CHR17 detection and enumeration using the aforementioned single-stranded oligonucleotide probes.

In an illustrative embodiment, systems for in situ hybridization may comprise a control probe specific to a control region of a chromosome, e.g., CHR17. The control probe is configured to hybridize to formalin fixed paraffin embedded (FFPE) tissue in about 3 hours or less, e.g., 1 hour or less. In some embodiments, the control probe is a plurality of synthetic single-stranded oligonucleotides. The system may also feature a target probe specific to a target region of the chromosome, wherein the target probe is also configured to hybridize in about 3 hours or less, e.g., 1 hour or less. In some embodiments, the control region is a centromere. The target region may be a gene or gene locus.

In yet another illustrative embodiment, systems for in situ hybridization may comprise a control probe specific to a control region of CHR17, the control probe is labeled with at least one first label, the control probe is configured to achieve a staining intensity of ≥2 and staining coverage of ≥50% of the number of total nuclei of a control sample within 3 hours of hybridization.

In some embodiments, the systems for in situ hybridization may feature a target probe specific to a target region of CHR17, e.g., a HER2 probe specific to the HER2 gene on CHR17, wherein the target probe is labeled with at least one label, the target probe is configured to achieve an enumerable signals and staining coverage of ≥50% of the number of total nuclei of a target sample within 3 hours of hybridization.

In other illustrative embodiments, methods for in situ hybridization of a tissue sample may comprise contacting the tissue sample with a control probe, hybridizing the control probe to the control region under conditions for a period of time less than about 3 hours, rinsing the sample to remove unbound probe, and detecting presence of the hybridized probe. The control may comprise a plurality of single-stranded labeled synthetic oligonucleotides. In one embodiment, the method further comprises applying chromogenic detection reagents that recognize labels and amplify the signal associated with the probes. In further embodiments, methods using and kits pertaining to the aforementioned systems are disclosed.

In some illustrative embodiments, methods for obtaining two bright-field chromogenic in situ hybridization signals per cell may comprise contacting a tissue sample containing a plurality of cells with a control probe specific to a control region of a single chromosome, the probe selected so as to not evidently bind non-specifically in the absence of blocking DNA; hybridizing the control probe to the control region of said chromosome; rinsing the sample to remove unbound probe; and detecting the presence of the hybridized probe via a chromogenic reagent so as to generate two bright-field chromogenic in situ hybridization signals per cell.

Additional features of the present disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

FIG. 15 shows that 14 oligonucleotide sequences comprising the higher order repeat units in the centromere region of CHR17 had high homology to several other chromosomes (e.g., chromosome 1, X, 11, 9, 20, 22, etc.). For example, Oligonucleotide M2.1 had 21 on-target hits but also had 33 hits on chromosome 1; Oligonucleotide M2.2 had 18 on-target hits but also had 14 hits on chromosome X.

FIG. 16(B-D) show examples of concentric circles and simple closed curves used for evaluating enumerable signals: (i) where the minimum radius (or inner radius ($R_{in}$)) is 80% of the maximum radius (or outer radius ($R_{out}$)) (in FIG. 16(B)), (ii) where the minimum radius (or inner radius ($R_{in}$)) is 50% of the maximum radius (or outer radius ($R_{out}$)) (in FIG. 16(C)), and (iii) where the minimum radius (or inner radius ($R_{in}$)) is 75% of the maximum radius (or outer radius ($R_{out}$)) (in FIG. 16(D)).

SEQUENCES

Figures 1A, 1B:
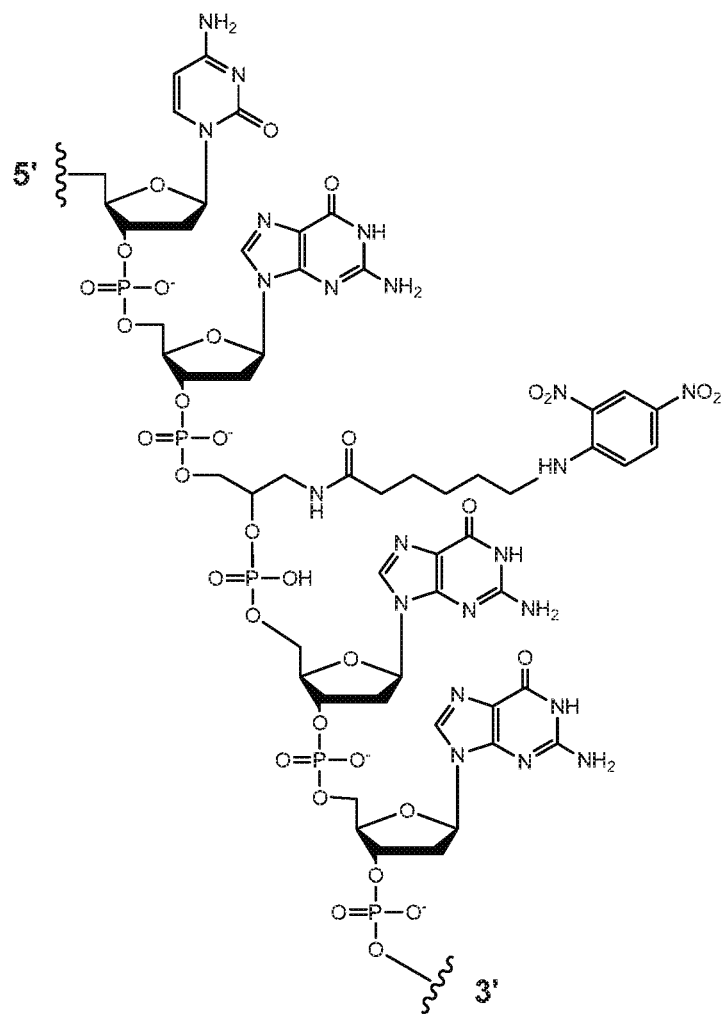
FIG. 1(A-B) is a sequence (SEQ. ID. NO: 1) showing label locations and structural perspective of a disclosed probe showing an illustrative labeling approach.

The nucleic acid sequences provided herein are shown using standard letter abbreviations for nucleotide bases, as defined in 37 C.F.R. 1.822. Only one strand of each nucleic acid sequence is shown, but the complementary strand is understood as included by any reference to the displayed strand. In the provided sequences:

SEQ ID NOs: 1-16 are examples of nucleic acid sequences of probes, e.g., probes with labels, to human chromosome 17.

DETAILED DESCRIPTION

I. Definitions

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999.

All publications, patent applications, patents, and other references mentioned herein are incorporated by reference in their entirety for all purposes.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Conjugating, joining, bonding or linking: Covalently linking one molecule to another molecule to make a larger molecule. For example, making two polypeptides into one contiguous polypeptide molecule, or covalently attaching a mass tag, hapten, nucleic acid, or other molecule to a polypeptide, such as a scFv antibody.

Contacting refers to placement that allows association between two or more moieties, particularly direct physical association, for example both in solid form and/or in liquid form (for example, the placement of a biological sample, such as a biological sample affixed to a slide, in contact with a composition, such as a solution containing the probes disclosed herein).

Detect: To determine if an agent (such as a signal or particular antigen, protein or nucleic acid) is present or absent, for example, in a sample. In some examples, this can further include quantification, and/or localization, for example localization within a cell or particular cellular compartment. "Detecting" refers to any method of determining if something exists, or does not exist, such as determining if a target molecule is present in a biological sample. For example, "detecting" can include using a visual or a mechanical device to determine if a sample displays a specific characteristic. In certain examples, light microscopy and other microscopic means are used to detect a detectable label bound to or proximally to a target.

Detectable label: A molecule or material that can produce a detectable (such as visually, electronically or otherwise) signal that indicates the presence and/or concentration of a target, such as a target molecule, in a sample, such as a tissue sample. When conjugated to a molecule capable of binding directly or proximally to a target, the detectable label can be used to locate and/or quantify the target. Thereby, the presence and/or concentration of the target in a sample can be detected by detecting the signal produced by the detectable label. A detectable label can be detected directly or indirectly, and several different detectable labels conjugated to different molecules can be used in combination to detect one or more targets. Multiple detectable labels that can be separately detected can be conjugated to different molecules that bind directly or proximally to different targets to provide a multiplexed assay that can provide detection of the multiple targets in a sample. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in Molecular Cloning: A Laboratory Manual, 3rd Ed., Cold Spring Harbor Laboratory Press (2001) and Ausubel et al., in Current Protocols in Molecular Biology, Greene Publishing Associates and Wiley-Intersciences (1987, and including updates).

Hapten: A molecule, typically a small molecule that can combine specifically with an antibody, but typically is substantially incapable of being immunogenic except in combination with a carrier molecule.

HER2: Also known as v-erb-b2 avian erythroblastic leukemia viral oncogene homolog 2 (ErbB2), human epidermal growth factor receptor 2, Her2/neu, c-erb B2/neu, and neuroblastoma/glioblastoma derived oncogene homolog; GenBank Gene ID Accession No. 2064. A member of the epidermal growth factor receptor tyrosine kinase family. Her2 heterodimerizes with other ligand-bound EGF receptor family members, though it lacks a ligand binding domain and cannot bind ligands itself. Amplification and/or overexpression of Her2 occur in several types of cancer, including breast and ovarian cancer.

Her2 nucleic acid and protein sequences are publicly available. For example, the Her2 gene is located on chromosome 17q12 and its sequence is disclosed as GenBank Accession No. NC_000017.10 (37844167-37884915). GenBank Accession Nos. NM_001005862, NM_004448, XM_005257139, and XM_005257140 disclose Her2 nucleic acid sequences, and GenBank Accession Nos.: NP_001005862, NP_004439, XP_005257196, and XP_005257197 disclose Her2 protein sequences, all of which are incorporated by reference as provided by GenBank on Oct. 4, 2013.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. The presence of a chemical which decreases hybridization (such as formamide) in the hybridization buffer will also determine the stringency (Sadhu et al., *J. Biosci.*, 6:817-821, 1984). Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). Hybridization conditions for ISH are also discussed in Landegent et al., *Hum. Genet.*, 77:366-370, 1987; Lichter et al., *Hum. Genet.*, 80:224-234, 1988; and Pinkel et al., *Proc. Natl. Acad. Sci. USA*, 85:9138-9142, 1988.

Isolated: An "isolated" biological component (such as a nucleic acid molecule, protein, or cell) has been substantially separated or purified away from other biological components in a preparation, a cell of an organism, or the organism itself, in which the component occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. In some examples, the nucleic acid probes disclosed herein are isolated nucleic acid probes.

Linker: As used herein, a linker is a molecule or group of atoms positioned between two moieties. For example, a mass tag conjugate may include a linker between the mass tag and the specific binding moiety. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker.

Multiplex, -ed, -ing: Embodiments of the present invention allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Probe: A nucleic acid molecule that is capable of hybridizing with a target nucleic acid molecule (e.g., genomic target nucleic acid molecule) and, when hybridized to the target, is capable of being detected either directly or indirectly. Thus probes permit the detection, and in some examples quantification, of a target nucleic acid molecule. In particular examples, a probe includes at least two segments complementary to uniquely specific nucleic acid sequences of a target nucleic acid molecule and are thus capable of specifically hybridizing to at least a portion of the target nucleic acid molecule. Generally, once at least one segment or portion of a segment has (and remains) hybridized to the target nucleic acid molecule other portions of the probe may (but need not) be physically constrained from hybridizing to those other portions' cognate binding sites in the target (e.g., such other portions are too far distant from their cognate binding sites); however, other nucleic acid molecules present in the probe can bind to one another, thus amplifying signal from the probe. A probe can be referred to as a "labeled nucleic acid probe," indicating that the probe is coupled directly or indirectly to a detectable moiety or "label," which renders the probe detectable.

Sample: A specimen containing DNA (for example, genomic DNA), RNA (including mRNA), protein, or combinations thereof, obtained from a subject. Examples include, but are not limited to, chromosomal preparations, peripheral blood, urine, saliva, tissue biopsy, fine needle aspirate, surgical specimen, bone marrow, amniocentesis samples, and autopsy material. In one example, a sample includes genomic DNA. In some examples, the sample is a cytogenetic preparation, for example which can be placed on microscope slides. In particular examples, samples are used directly, or can be manipulated prior to use, for example, by fixing (e.g., using formalin).

Sequence identity: The identity (or similarity) between two or more nucleic acid sequences is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.*, 2:482, 1981; Needleman & Wunsch, *J. Mol. Biol.*, 48:443, 1970; Pearson & Lipman, *Proc. Natl. Acad. Sci. USA*, 85:2444, 1988; Higgins & Sharp, *Gene*, 73:237-44, 1988; Higgins & Sharp, *CABIOS* 5:151-3, 1989; Corpet et al., *Nuc. Acids Res.*, 16:10881-90, 1988; Huang et al. *Computer Appls. in the Biosciences*, 8:155-65, 1992; and Pearson et al., *Meth. Mol. Bio.*, 24:307-31, 1994. Altschul et al., *J. Mol. Biol.*, 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology and on the Internet, for use in connection with the sequence analysis programs blastp, blastn, blastx, tblastn and tblastx. Additional information can be found at the NCBI web site.

BLASTN may be used to compare nucleic acid sequences, while BLASTP may be used to compare amino acid sequences. If the two compared sequences share homology, then the designated output file will present those regions of homology as aligned sequences. If the two compared sequences do not share homology, then the designated output file will not present aligned sequences.

The BLAST-like alignment tool (BLAT) may also be used to compare nucleic acid sequences (Kent, Genome Res. 12:656-664, 2002). BLAT is available from several sources, including Kent Informatics (Santa Cruz, Calif.) and on the Internet (genome.ucsc.edu).

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 15 consecutive nucleotides from an identified sequence as follows contains a region that shares 75 percent sequence identity to that identified sequence (that is, 15÷20100=75).

Subject: Any multi-cellular vertebrate organism, such as human or non-human mammals (e.g., veterinary subjects).

Target nucleic acid sequence or molecule: A defined region or particular portion of a nucleic acid molecule, for example a portion of a genome (such as a gene or a region of mammalian genomic DNA containing a gene of interest). In an example where the target nucleic acid sequence is a target genomic sequence, such a target can be defined by its position on a chromosome (e.g., in a normal cell), for example, according to cytogenetic nomenclature by reference to a particular location on a chromosome; by reference to its location on a genetic map; by reference to a hypothetical or assembled contig; by its specific sequence or function; by its gene or protein name; or by any other means that uniquely identifies it from among other genetic sequences of a genome. In some examples, the target nucleic acid sequence is mammalian genomic sequence (for example human genomic sequence).

In some examples, alterations of a target nucleic acid sequence (e.g., genomic nucleic acid sequence) are "associated with" a disease or condition. In some examples, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by polynucleotide polymorphisms, and/or the two different forms can be quantitatively distinguishable, such as by the number of copies of the target nucleic acid sequence that are present in a cell.

Uniquely specific sequence: A nucleic acid sequence (for example, a sequence of at least of at least 20 bp (such as at least 20 bp, 30 bp, 40 bp, 50 bp, 60 bp, 70 bp, 80 bp, 90 bp, 100 bp, or more) that is present only one time in a haploid genome of an organism. In a particular example, a uniquely specific nucleic acid sequence is a nucleic acid sequence from a target nucleic acid that has 100% sequence identity with the target nucleic acid and has no significant identity to any other nucleic acid sequences present in the specific haploid genome that includes the target nucleic acid.

Vector: Any nucleic acid that acts as a carrier for other ("foreign") nucleic acid sequences that are not native to the vector. When introduced into an appropriate host cell a vector may replicate itself (and, thereby, the foreign nucleic acid sequence) or express at least a portion of the foreign nucleic acid sequence. In one context, a vector is a linear or circular nucleic acid into which a nucleic acid sequence of interest is introduced (for example, cloned) for the purpose of replication (e.g., production) and/or manipulation using standard recombinant nucleic acid techniques (e.g., restriction digestion). A vector can include nucleic acid sequences that permit it to replicate in a host cell, such as an origin of replication. A vector can also include one or more selectable marker genes and other genetic elements known in the art. Common vectors include, for example, plasmids, cosmids, phage, phagemids, artificial chromosomes (e.g., BAC, PAC, HAC, YAC), and hybrids that incorporate features of more than one of these types of vectors. Typically, a vector includes one or more unique restriction sites (and in some cases a multi-cloning site) to facilitate insertion of a target nucleic acid sequence.

II. Systems for In Situ Hybridization for Chromosome Enumeration

The present disclosure describes an automated brightfield dual ISH assay for the simultaneous detection of a gene target (e.g. HER2) and a centromere target (e.g. CHR17) using single-strand oligonucleotide probes. One aspect of this assay is the discovery of particular probes that enable compatibility between the centromere probe and the gene probe. In particular, a pool of single-strand oligonucleotide probes for the centromere targets was discovered that are highly compatible with a pool of single-strand oligonucleotide probes for the gene target. The centromere oligonucleotide sequences are selected to avoid the need for using human blocking DNA. The probes, as used in a dual in situ hybridization (DISH) assay achieved comparable staining performance to commercial dual-strand probe products; however, the single-strand probes hybridize in 1 hour while the dual-strand probes required longer (e.g. 6 hours). The two probe types were highly concordant on the diagnosis of gene status, but the single-strand probe achieved a lower assay failure rate. When tested on specimens with unknown pre-analytical conditions and tissue quality, the single-strand probe proved to be more robust than dual-strand probe products even using the highly disparate hybridization times (e.g. 1 hour versus 6 hours).

Gene copy number assessment is a major ISH application in both cytogenetics and anatomical pathology laboratories. For example, determination of HER2 gene status requires the use of chromosome 17 centromere (CEN 17) enumeration, so the HER2/CEN 17 ratio can be calculated. In order to take advantages of the single-strand oligonucleotide probe approach for this application, however, several technical hurdles had to be overcome. First, CHR17 oligonucleotide probe needs to accommodate the assay conditions for HER2 oligonucleotide probe; Second, CHR17 oligonucleotide probe needs to be robust enough for adequate sensitivity; Third, CHR17 oligonucleotide probe needs to be specific enough to CHR17 centromere and therefore there is no need for the suppressive hybridization reagents such as human placenta or Cot1 DNA.

Currently, all commercially available HER2 ISH assays use labeled segments of double strand DNA obtained from bacterial artificial chromosome (BAC) as the original source (See HER2 FISH PHARMDX Kit Interpretation guide—breast cancer, PATHVYSION HER2 DNA Probe Kit, and Interpretation Guide Ventana INFORM HER2 Dual ISH DNA Probe Cocktail Assay). BACs are either directly labeled with fluorophore molecules as probes (HER2 FISH PHARMDX Kit, Dako and PATHVYSION HER2 DNA Probe Kit, Abbott Molecular, Inc.), or as template to generate more specific sequences by physical subtraction or avoidance of repetitive sequences (SPOT-LIGHT HER2 CISH Kit, Life Technologies, Inc. and INFORM HER2 Dual ISH assay, Ventana Medical Systems, Inc.). It is well known that these double strand probes require prolonged hybridization time (i.e. from 6 hrs to 18 hrs) to ensure sufficient hybridization to the targets. The extended time reflects low hybridization efficiency. Importantly, it has a negative impact on patients who must wait for their diagnosis for because of the extended turnaround times associated with tissue-based ISH assays. The criteria in TABLE 1 are typically used to evaluate whether a particular DISH assay is acceptable or not acceptable.

TABLE 1

Analytical slide scoring criteria.

| | Acceptable (A) | Not Acceptable (N) |
|---|---|---|
| Signal Intensity | 3, Signals are bright and easily identified in >80% of cells within the target region. 2, Specific signals are sufficiently intense to reliably identify in >50% | 1, Specific signals are visible but too weak to reliably identify in ≥50% of the targeted region. 0.5, Signals are visible but absent or too weak to reliably identify in |

TABLE 1-continued

Analytical slide scoring criteria.

| | Acceptable (A) | Not Acceptable (N) |
|---|---|---|
| Background | of cells within the targeted region. 1, Background signals (either punctate signals or diffuse, hazy staining) are present but are sufficiently weak in intensity within the nuclei to permit reliable identification of specific signals in >50% of cells within the target region. 0, Background staining is not observed in >80% of cells within the target region. | 80% of cells. 0, Signals are not visible. 3, Background signals (punctate signals, diffuse staining, haze) cover 75-100% of cells within the target region and are sufficiently intense to obscure specific signals. 2, Background signals (punctate signals, diffuse staining, haze) cover 50-75% of cells within the target region and are sufficiently intense to obscure specific signals |

There have been several approaches to enhance the hybridization efficiency, so as to decrease the turnaround times for these assays. One approach for accelerating hybridization reaction rates was to change the composition of the hybridization buffer. Currently, formamide is routinely used to lower the melting point and annealing temperature of nucleic acid strands. The benefit of lowering the temperature is to better preserve the tissue morphology (See McConaughy B L, et al., *Biochemistry* 8: 3289-3295 (1969) and Blake R D, Delcourt S G, *Nucleic Acids Res* 24: 2095-2103 (1996), the disclosures of which are incorporated in their entirety herein by reference). However, a long hybridization is required to obtain sufficient signal intensity as formamide reduces hybridization rate. Recently, Matthiesen S H et al., *PLoS One*. 2012; 7(7) reported ethylene carbonate (EC) as the substitute for formamide in hybridization buffers with the effect of reducing FISH hybridization time to one hour. It is understood that this technology underlies the new commercial product HER2 IQFISH PHARMDX (Dako).

Another approach has been to switch from double strand to single strand probes. Single strand probes are understood to have higher sensitivity than that of double strand probes, presumably because a proportion of the denatured double-strand probe renatures to form probe homoduplexes, thus preventing their hybridization to genomic targets in the test samples (See Taneja K and Singer R H, *ANALYTICAL BIOCHEMISTRY* 166, 389-398 (1987), Lewis M E, et al., *Peptides*. 6 Suppl 2:75-87 (1985) and Strachan T, Read A P. Human Molecular Genetics. 2nd edition. New York: Wiley-Liss (1999)).

In Kourilsky P, et al., *Biochimie*. 56 (9): 1215-21 (1974), it was found that the percentage of single strand nucleotides (available as probe) is inversely proportional to the amount of competitive strand nucleotide in the solution at the pre-hybridization step. A mathematical model developed in this study revealed that homologous competition is a powerful competitor of DNA-target hybridization. Several laboratories have reported that single-strand probes provide higher sensitivity on hybridization than double-stranded probes (See An SF, et al., *Mol Cell Probes*. June; 6(3):193-200 (1992), Hannon K, et al., *Anal Biochem*. August 1; 212(2):421-7 (1993), and Cox K H, et al., *Dev Biol*. February; 101(2):485-502 (1984)). In particular, An et al.'s work demonstrated digoxigenin (DIG) labeled single-strand probes were at least two-fold more sensitive than double-strand DIG PCR-labeled probes of the same size, and 10-fold more sensitive than nick translated double-strand probes of the same size in dot-blot hybridization. In ISH application, single stranded probes were more sensitive, i.e. detecting approximately two- to four-fold the number of infected cells than double-strand probes of the same size. Furthermore, it gave much less background staining than double-stranded probe of the same size in ISH. Single-strand probes did not need purification before use in ISH; in contrast, the double strand PCR probes needed purification; otherwise there was a large amount of nonspecific background staining. Further, it was demonstrated by Hannon et al. that the DIG-labeled single strand DNA probe was approximately 27% more intense (by an image analysis program) than that obtained using DIG-double strand probe. Cox K H et al., *Dev Biol*. February; 101(2):485-502 (1984) found eightfold more of the single strand probe hybridized to target sequence at apparent saturation, while the observed hybridization reaction with double strand probes terminated at a level far below saturation of available target sites. This implied that most of the double stand probe was removed from the ISH reaction relatively early. Consistent to the above findings, we discovered single strand HER2/CHR17 probes with 1 hour hybridization achieved comparable staining performance to that of dual strand probe with 6 hour hybridization. Surprisingly, the single strand probe with 1 hour hybridization also demonstrated superior robustness on a cohort of difficult tissues (TMA). Our data is aligned with previous observations that single strand probes tend to have higher hybridization efficiency than that of double strand probes.

While not being limited to a particular theory, we perceive another advantage of single strand probes being that that they more easily penetrate the tissue. Double strand probes are usually labeled by incorporating labeled dNTPs in an enzymatic DNA synthesis reaction. The labeled probes are sized to smaller fragments by DNase treatment or mechanical sonication. The optimal length of the labeled ISH probes is typically understood to be between 100 and 400 nucleotides according to Cox, et al., *Dev Biol*. February; 101(2): 485-502 (1984) and Haase et al. (See Haase, A. et al., in *Methods in Virology* (Maramorosch, K., and Koprowski, Eds.), Vol. 7, pp. 189-226, Academic Press, San Diego, Calif. (1984)). However, the "random" nature of the size-down process for the labeled probes is understood to render the majority of the probes within the correct size, but produce a wide population of sizes. Single strand probes generated by oligonucleotide synthesis have well-defined short lengths which facilitate the ability of the probe to penetrate tissue better than larger double strand probes, especially on difficult tissue specimens (e.g. over-fixed). It was discovered that the single strand probes described herein exhibit superior staining on a cohort of difficult tissues (TMA), which may be partially explained by better tissue penetration of short and uniform probes.

Furthermore, from the perspective of manufacturing and quality control, a single strand probe having an exact structure are more reproducibly manufactured using oligonucleotide synthesis compared to the approaches based on PCR, nick translation, or other random synthetic approaches.

Oligonucleotide probes ideally hybridize maximally with the target and minimally with non-targets (See Li X, et al., *Nucleic Acids Res.*, October 24; 33(19): 6114-23 (2005)). While these references applicable to solution or array based hybridization may be relevant to consider, the hybridization kinetics to genomic targets on formalin fixed paraffin embedded (FFPE) tissues is highly unpredictable in comparison. This unpredictability is understood to be imparted by the highly complex and variable nature of human tissues, especially in comparison to either a solution or an array. In microarray application, a 50-mer probe showing 75% identity to non-targets or with 15-, 20-, or 35-base stretches showed cross-reactivity in Kane M D, et al., *Nucleic Acids Res*. November 15; 28(22):4552-7 (2000). A 60-mer probe with 80% identity to non-targets showed cross-reactivity to non-target in Hughes T R, et al., *Nat Biotechnol*. April; 19(4):342-7 (2001). Similar results were shown with a 70-mer by Wang X, Seed B., *Bioinformatics*. May 1; 19(7): 796-802 (2003).

Li X, et al., *Nucleic Acids Res.*, October 24; 33(19): 6114-23 (2005) appears to have proposed an optimal choice for designing 50-mer oligonucleotides: identity of <87%, continuous stretch of <17 bases, and free energy of >29 kcal/mol. Both 50-mer and 70-mer probes were observed to have minimal cross-hybridization to sequences having less than 85% identity to the respective targets, whereas the signal intensity increased substantially for probes that had more than 90% identity to the respective targets (See He Z, et al., *Appl Environ Microbiol*. July; 71(7):3753-60 (2005)). He Z et al. suggested that a gene-specific probe should have an identity of <85% to non-targets under the conditions examined.

While synthetic oligonucleotide probes have been widely used for messenger RNA ISH, it has not been used on genomic targets until recently (See Bergstrom Lucas A, Ruvolo M, Kulkarni V, Chen S, Mullinax B, Venneri J, Barboza J, Happe S, Fulmer-Smentek S, Srinivasan M. Designing Custom Oligonucleotide FISH Probes for the Detection of Chromosomal Rearrangements in FFPE Tissues. *American Society of Human Genetics* 2073 *Meeting*). Bergstrom et al. reported SUREFISH probes with fluorescence labels that were understood to include thousands of unique oligonucleotides. The oligonucleotide sequences were tiled across the targeted chromosomal region of translocation breakpoints for the detection of chromosomal rearrangements. A short hybridization time (75 min) was reported for these probes.

The most common target of chromosome 17 ISH is the centromeric regions. The centromeric regions of all human chromosomes are characterized by distinct subsets of a diverse tandemly repeated DNA family, alpha satellite. The fundamental unit of alpha satellite is the diverged 171-bp monomer, by which higher-order chromosome-specific repeat units are organized. The human chromosome 17-specific alpha satellite contains approximately 1,000 polymorphic higher-order repeat units that range from 11 to 16 monomers. The predominant form of chromosome 17 alpha satellites is a ~2,700 base pair repeat unit that consists of 16 monomers, which is present in 500 to 1,000 copies per chromosome 17. Since alpha satellite DNA clusters most often contain monomer variants that differ from the consensus sequence by up to 40% (Rosandić M, Paar V, Glunčić M, Basar I, Pavin N, Croat Med J. 2003 August; 44(4):386-406), blocking DNA is usually included with the probes to suppress sequences contained within the target loci that are common to other chromosomes. One aspect of the present disclosure is the discovery of single strand oligonucleotides from the 2,700 base pair repeat unit with comparable melting temperature (Tm) range to that of a 80-mer single strand gene probe. In particular, it was discovered that 14 particular single strand oligonucleotides specific to the chromosome 17 centromere could robustly enable a gene/centromere DISH assay with the 80-mer gene probes. The sequences of the 14 oligonucleotides are from 10 of the 16 monomers;

therefore they increase the probability of recognizing haplotype-specific sequence variation in the population.

While the examples herein describe particularly a single strand oligonucleotide-based CHR17 (or HER2/CHR17 dual) ISH assay, it is understood that those of ordinary skill in the art could apply the discoveries disclosed herein to any gene/centromere combination of interest.

Difficulties frequently encountered in both IHC and ISH testing results from the manner in which the tissues are typically preserved. The mainstay of the diagnostic pathology laboratory has been for many decades the formalin-fixed, paraffin-embedded block of tissue, sectioned and mounted upon glass slides. Fixation in such a preservative causes cross-linking of macromolecules, both amino acids and nucleic acids. These cross-linked components must be removed to allow access of the probe to the target nucleic acid and to allow the antibody to recognize the corresponding antigen. "Unmasking" the antigen and/or nucleic acid is typically accomplished manually with multiple pretreatment, proteolytic digestion, and wash steps. Prior to staining, complete removal of the paraffin is also required so that it does not interfere with antibody or probe binding. Deparaffinization may be achieved by the use of multiple (e.g., two or three) successive clearing reagents that are paraffin solvents (e.g., xylene, xylene substitutes, or toluene).

In an illustrative embodiment, preparing includes the step of cell conditioning. Cell conditioning is discussed in greater detail in U.S. Pat. No. 6,855,552, Towne, et al. "Automated immunohistochemical and in situ hybridization assay formulations", the subject matter of which is expressly incorporated by reference. In illustrative cell conditioning steps, a cell conditioning reagent is applied and the sample is contacted at the appropriate temperature for an appropriate duration of time so that the antigens and/or nucleic acid targets are sufficiently expressed for detection. One aspect of the present disclosure is that the automated instrument can automatically adjust the cell conditioning duration and/or temperature in response to the user inputs. Cell conditioning may further include applying a protease reagent. Illustratively, a protease treatment may involve the step of contacting a protease solution to a biological sample. The protease treatment, as with cell conditioning, is intended to increase the expression of target antigens and/or nucleic acids.

Exemplary cell conditioning reagents include, for nucleic acid targets (ISH), a solution including ethylenediaminetetraacetic acid (EDTA) may be used. The contacting may be done at a temperature of about 95° C. for between about 2 and about 90 minutes. For protein targets (IHC), a cell conditioning solution may be a boric acid buffer. The contacting may be may be done at a temperature of about 100° C. for between about 2 and about 90 minutes. A partial list of possible reagents appears in Analytical Morphology, Gu, ed., Eaton Publishing Co. (1997) at pp. 1-40. Sodium dodecyl sulfate (SDS) and/or ethylene glycol may be included in the conditioning solution. Furthermore, metal ions or other materials may be added to these reagents to increase effectiveness of the cell conditioning. Exemplary cell conditioning solutions are available from Ventana Medical Systems, Inc., Tucson, Ariz. (Cell Conditioning 1 (CC1) catalog #: 950-124; Cell Conditioning 2 (CC2) catalog #: 950-123; SSC (10×) catalog #: 950-110; ULTRA Cell Conditioning (ULTRA CC1) catalog #: 950-224; ULTRA Cell Conditioning (ULTRA CC2) catalog #: 950-223, Protease 1 catalog #: 760-2018; Protease 2 catalog #: 760-2019; Protease 3 catalog #: 760-2020). In one embodiment, applying the immunohistochemical binding reagent or the in situ hybridization binding reagent occurs subsequent to applying the cell conditioning reagent and prior to applying the chromogenic reagent.

In illustrative embodiments, the method includes applying a rinsing reagent. Between various steps described herein and as part of the system described herein, rinse steps may be added to remove unreacted residual reagents from the prior step. Rinse steps may further include incubations, which include maintaining a rinsing reagent on the sample for a pre-determined time at a pre-determined temperature with or without mixing. The conditions appropriate for the rinsing steps may be distinct between the various steps. Exemplary rinsing reagents are available from Ventana Medical Systems, Inc., Tucson, Ariz. (Reaction Buffer (10×) catalog #: 950-300; Special Stains Wash (10×) catalog #: 860-015).

Exemplary automated systems available through Ventana Medical Systems, Inc., Tucson, Ariz. include SYMPHONY® Staining System, catalog #: 900-SYM3, VENTANA® BenchMark Automated Slide Preparation Systems, catalog #s: N750-BMKXT-FS, N750-BMKU-FS, VENTANA, and VENTANA® BenchMark Special Stains automated slide stainer. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

A. Chromosome 17

As previously discussed, the most common target for a control region of chromosome 17 (CHR17) ISH is the centromeric region. The centromeric regions of all human chromosomes are characterized by distinct subsets of a diverse tandemly repeated DNA family, alpha satellite. Since alpha satellite DNA clusters most often contain monomer variants that differ from the consensus sequence by up to 40%, blocking DNA is usually included with the probes to suppress sequences contained within the target loci that are common to other chromosomes.

We designed single-stranded probes directed to the control region (centromeric region) of chromosome 17 that achieved acceptable signal intensity levels and background levels within 1 hour of hybridization and without the use of blocking DNA (See TABLE 3 of Example 1). For example, the probes are configured to achieve a staining intensity of greater than or equal to 2 and staining coverage of greater than or equal to 50% of nuclei. We also designed single-stranded probes directed to a target region near and within the HER2 gene locus that also achieved acceptable signal intensity levels and background levels within 1 hour of hybridization and without the use of blocking DNA.

From the perspective of manufacturing and quality control, a single-stranded probe having an exact structure are more reproducibly manufactured using oligonucleotide synthesis compared to the approaches based on PCR, nick translation, or other random synthetic approaches. From the perspective of cost analysis, the probes that do not require blocking DNA provide for a less expensive assay.

The present disclosure describes systems for ISH featuring a control probe specific to a control region of a chromosome, e.g., a centromere target of a chromosome. The chromosome detected may be chromosome 17, or any other appropriate chromosome. The control probe is configured to achieve a staining intensity of greater than or equal to 2 and staining coverage of greater than or equal to 50% of the number of nuclei within 3 hours when applied to a control sample (e.g., as described above, TABLE 1). In some embodiments, the present invention achieves a staining coverage of ≥55% of the number of nuclei within 3 hours, e.g., ≥60% of the number of nuclei, ≥65% of the number of nuclei, ≥70% of the number of nuclei, ≥75% of the number of nuclei, ≥80% of the number of nuclei, ≥85% of the number of nuclei, ≥90% of the number of nuclei.

In some embodiments, the systems for ISH also feature a target probe specific for a target region (e.g., for detecting a target gene) on the corresponding chromosome.

In some embodiments, the control probe comprises a first plurality (e.g., a plurality of a single probe, a plurality of different probes such as a set or pool of probes) of single-stranded oligonucleotide probes. One or more of the plurality of probes may comprise a sequence selected from the group consisting of SEQ ID NOs: 3-16 (See TABLE 3 below). In some embodiments, one or more of the first plurality of probes comprise a truncated version (e.g., at least 30 contiguous bp, at least 35 contiguous bp, at least 40 contiguous bp, at least 45 contiguous bp, at least 50 contiguous bp, at least 55 contiguous bp, at least 60 contiguous bp, at least 65 contiguous bp, at least 70 contiguous bp, at least 75 contiguous bp, etc.) of one of the sequences in TABLE 3 (SEQ ID NOs: 3-16). In some embodiments, one or more of the first plurality of probes comprises a sequence that has at least 70% sequence identity, at least 75% sequence identity, at least 80% sequence identity, at least 85% sequence identity, at least 90% sequence identity, or at least 95% sequence identity to one of the sequences in TABLE 3 (SEQ ID NOs: 3-16). The first plurality of single-stranded oligonucleotide probes is configured to hybridize uniquely and specifically to a portion of the control region of human chromosome 17 so that other chromosomes or portions thereof are not evidently labeled.

As used herein, reference to use of SEQ ID NOs: 3-16 may also include the use of complementary sequences of SEQ ID NOs: 3-16.

In some embodiments, the probes target between 2 and 16 distinct portions within the control region. In some embodiments, the probes target between 4 and 16 distinct portions within the control region. In some embodiments, the probes target between 6 and 16 distinct portions within the control region. In some embodiments, the probes target between 8 and 16 distinct portions within the control region. In some embodiments, the probes target between 10 and 16 distinct portions within the control region. In some embodiments, the probes target between 12 and 16 distinct portions within the control region. In some embodiments, the probes target between 14 and 16 distinct portions within the control region. In some embodiments, the probes target between 2 and 12 distinct portions within the control region. In some embodiments, the probes target between 4 and 12 distinct portions within the control region. In some embodiments, the probes target between 6 and 12 distinct portions within the control region. In some embodiments, the probes target between 8 and 12 distinct portions within the control region. In some embodiments, the probes target between 10 and 12 distinct portions within the control region.

Without wishing to limit the present invention to any theory or mechanism, it is believed that the probes may be able to identify at least 60% of chromosome 17 polymorphisms, at least 70% of chromosome 17 polymorphisms, at least 80% of chromosome 17 polymorphisms, at least 90% of chromosome 17 polymorphisms, at least 95% of chromosome 17 polymorphisms, at least 99% of chromosome 17 polymorphisms, etc. It is not clear how many monomers would need to be probed to be sufficient for identifying at least 60% of chromosome 17 polymorphisms, at least 70% of chromosome 17 polymorphisms, at least 80% of chromosome 17 polymorphisms, at least 90% of chromosome 17 polymorphisms, at least 95% of chromosome 17 polymorphisms, at least 99% of chromosome 17 polymorphisms, etc.

The first plurality of single-stranded oligonucleotide probes may be constructed in a variety of lengths. For example, in some embodiments, the probes each comprise between 40 to 100 nucleotides. In some embodiments, the probes each comprise between 50 to 100 nucleotides. In some embodiments, the probes each comprise between 60 to 110 nucleotides. In some embodiments, the probes each comprise between 40 to 120 nucleotides. In some embodiments, the probes each comprise at least 40 nucleotides. In some embodiments, the probes each comprise at least 50 nucleotides. In some embodiments, the probes each comprise at least 60 nucleotides. In some embodiments, the probes each comprise at least 70 nucleotides.

The present invention also features slides with a plurality of nuclei stained for a chromosome control, e.g., CHR17 control. The slide may be contacted with one or more of the above systems (e.g., probes). The slide features enumerable signals indicative of the number of chromosome 17 centromere regions present in a cell, e.g., cells should exhibit two copies of the CHR17 centromere normally.

In some embodiments, more than 50% of the nuclei have enumerable signals for the chromosome. An enumerable signal may be a generally round shape. The round shape can be defined as shown in FIG. 16, wherein a round shape is a simple closed curve that fits within a first region, the first region lies on and outside an inner circle and on and inside a concentric outer circle, the inner circle has an inner radius ($R_{in}$) and the outer circle has a outer radius ($R_{out}$), wherein the simple close curve has a radius $R_{simple}$, wherein $R_{in} \leq R_{simple} \leq R_{out}$, and wherein, $R_{in}$ is ≥50% of $R_{out}$. A simple closed curve is a curve that does not cross itself and ends at the same point where it begins.

In some embodiments, the inner radius is no less than 40% of the outer radius. In some embodiments, the inner radius is no less than 50% of the outer radius. In some embodiments, the inner radius is no less than 55% of the outer radius. In some embodiments, the inner radius is no less than 60% of the outer radius. In some embodiments, the inner radius is no less than 65% of the outer radius. In some embodiments, the inner radius is no less than 70% of the outer radius. In some embodiments, the inner radius is no less than 75% of the outer radius. In some embodiments, the inner radius is no less than 80% of the outer radius. In some embodiments, the inner radius is no less than 85% of the outer radius. In some embodiments, the inner radius is no less than 90% of the outer radius.

In some embodiments, more than 60% of the nuclei have enumerable signals for the chromosome. In some embodiments, more than 70% of the nuclei have enumerable signals for the chromosome. In some embodiments, more than 80% of the nuclei have enumerable signals for the chromosome. In some embodiments, more than 90% of the nuclei have enumerable signals for the chromosome. The nuclei may not be enumerable if the tissue sectioning process has destroyed that portion of the cell, if that portion of the cell is divided between two slides, or if that portion of the cell is wholly within a separate slide. The nuclei may also be enumerable if the tissue condition prevents probe penetration to the specific binding site (i.e. the cell is not sufficiently accessible to the probe) or if the target region of DNA is substantially degraded.

In some embodiments, the sum of the surface area covered by staining signal is calculated and assigned a 100% value, and at least 50% of the sum of the surface area is derived from discrete round signals (or round shapes).

A round shape can be defined as shown in FIG. 16, wherein a round shape is a simple closed curve that fits within a first region, the first region lies on and outside an inner circle and on and inside a concentric outer circle, the inner circle has an inner radius ($R_{in}$) and the outer circle has a outer radius ($R_{out}$), wherein the simple close curve has a radius $R_{simple}$, wherein $R_{in} \leq R_{simple} \leq R_{out}$, and wherein, $R_{in}$ is $\geq 50\%$ of $R_{out}$.

In some embodiments, the inner radius is no less than 50% of the outer radius. In some embodiments, more than 60% of said sum of the surface area is derived from discrete round signals. In some embodiments, more than 70% of said sum of the surface area is derived from discrete round signals. In some embodiments, the inner radius is no less than 60% of the outer radius. In some embodiments, the inner radius is no less than 75% of the outer radius. In some embodiments, the inner radius is no less than 90% of the outer radius.

In some embodiments, the outer radius is between about 0.25 to 0.675 μm. In some embodiments, the outer radius is between about 0.2 to 0.75 μm. In some embodiments, the outer radius is between about 0.15 to 1 μm. In some embodiments, the average outer radius of the enumerable signals is between about 0.2 to 0.75 μm. In some embodiments, the average outer radius of the enumerable signals has a standard deviation of less than 0.5 μm. In some embodiments, the average outer radius of the enumerable signals has a standard deviation of less than 0.25 μm.

In some embodiments, the enumerable round signals are mono-sized. As used herein, a population of "mono-sized" round signals have the $R_{simple}$ being within 15% plus or minus of each other. In some embodiments, the population of "mono-sized" round signals have the $R_{simple}$ being within 10% plus or minus of each other. In some embodiments, the population of "mono-sized" round signals have the $R_{simple}$ being within 5% plus or minus of each other.

B. Target Gene (HER2)

In some embodiments, the systems for ISH also feature a target probe specific for a target region (e.g., for detecting a target gene, for gene copy enumeration) on the corresponding chromosome.

The target region may comprise the HER2 gene locus (or nearby nucleotides). Disclosed herein are probes directed to the human HER2 gene (See Terms for GenBank accession numbers). As described below in detail in EXAMPLE 1, the HER2 target probe is specific to a region between nucleotides 35,027,979 and 35,355,516 of human chromosome 17.

In some embodiments, the target probe comprises a second plurality (e.g., a plurality of a single probe, a plurality of different probes such as a set or pool of probes) of single-stranded oligonucleotide probes. The second plurality of single-stranded oligonucleotide probes is configured to hybridize uniquely and specifically to a portion of the target region of the corresponding chromosome so that other genes or chromosomes or portions thereof are not evidently labeled.

The present invention also features means of making the control region of chromosome 17 visible. In some embodiments, the means of making the control region of chromosome 17 visible comprises the step of contacting the probes with a detection reagent specific to the probes. Detection reagents are well known in the art. For example, the detection reagent may comprise an antibody or other probe, which binds to the control probe. The detection reagent may comprise a molecule (e.g., enzyme, substrate, tag) that makes the first label of the probe visible. The detection reagent may comprise a plurality of reagents effective for making the probe visible (e.g., more than one antibody, enzyme, substrate, chromogen, etc.). In some embodiments, the detection reagent emits a color. Additional detection reagents (labels, tags, enzymes, substrates, chromogens, antibodies, etc.) are further disclosed herein. The present invention also features means of visualizing the control region of chromosome 17, wherein the probe (e.g., first label) is made visible by a detection reagent and the visibility of the first label is indicative of the control region of chromosome 17. Means for visualizing labeled probes are well known to one of ordinary skill in the art. For example, in some embodiments, the means for visualizing the control region of chromosome 17 comprises a microscope (e.g., bright field microscope, fluorescence microscope, inverted microscope). In some embodiments, the means for visualizing the control region of chromosome 17 comprises a luminometer. In some embodiments, the means for visualizing the control region of chromosome 17 comprises a radiometric detection machine (e.g., gamma counter, etc.). In some embodiments, the means for visualizing the control region of chromosome 17 comprises a spectrometer. In some embodiments, the means for visualizing the control region of chromosome 17 comprises a real-time PCR machine. In some embodiments, the means for visualizing the control region of chromosome 17 comprises a scintillation and/or luminescence counter. In some embodiments, the means for visualizing the control region of chromosome 17 comprises a colorimeter. Other means for visualizing the control region of chromosome 17 are known in the art.

C. Kits

Also disclosed are kits including one or more of the oligonucleotide probes (for example, one or more of SEQ ID NOs: 3-16). For example, kits can include at least one probe (such as at least 1, 2, 3, 4, 5, 6, 7, 8, 9, 10, or more probes) or at least one probe set (such as at least 1, 2, 3, 4, or 5 probe sets) as described herein. In one example, the kit comprises probes such as at least 1, 2, 3, 4, 5, 6, 7, 8, 9, 10, 11, 12, 13, or all of SEQ ID NOs: 3-16 (or sequences at least 60%, at least 70%, at least 75%, at least 80%, at least 85%, or at least 90% identical to SEQ ID NOs: 3-16; or truncated versions of SEQ ID NOs: 3-16). In other examples, the probes (or the probe set) are in a single container.

The kits may also comprise one or more reagents for detecting the probe (for example, by in situ hybridization), or for producing a detectably labeled probe. For example, a kit can include at least one of the disclosed nucleic acid probes or probe sets, along with one or more buffers, labeled dNTPs, a labeling enzyme (such as a polymerase), primers, nuclease free water, and instructions for producing a labeled probe. In another example, the kit includes one or more of the disclosed nucleic acid probes (unlabeled or labeled) along with buffers and other reagents for performing in situ hybridization. For example, if one or more unlabeled probes are included in the kit, labeling reagents can also be included, along with specific detection agents (for example, fluorescent, chromogenic, luminescent and/or radiometric) and other reagents for performing an in situ hybridization assay, such as paraffin pretreatment buffer, protease(s) and protease buffer, prehybridization buffer, hybridization buffer, wash buffer, counterstain(s), mounting medium, or combinations thereof. In some examples, such kit components are present in separate containers. The kit can optionally further include control slides (such as positive or negative controls) for assessing hybridization and signal of the probe(s).

In certain examples, the kits include avidin, antibodies, and/or receptors (or other anti-ligands). Optionally, one or more of the detection agents (including a primary detection agent, and optionally, secondary, tertiary or additional detection reagents) are labeled, for example, with a hapten or fluorophore (such as a fluorescent dye or quantum dot). In some instances, the detection reagents are labeled with different detectable moieties (for example, different fluorescent dyes, spectrally distinguishable quantum dots, different haptens, etc.). For example, a kit can include two or more nucleic acid probes or probe sets that correspond to and are capable of hybridizing to different target nucleic acids (for example, any of the target nucleic acids disclosed herein). The first probe or probe set can be labeled with a first detectable label (e.g., hapten, fluorophore, etc.), the second probe or probe set can be labeled with a second detectable label, and any additional probes or probe sets (e.g., third, fourth, fifth, etc.) can be labeled with additional detectable labels. The first, second, and any subsequent probes or probe sets can be labeled with different detectable labels, although other detection schemes are possible. If the probe(s) are labeled with indirectly detectable labels, such as haptens, the kits can include detection agents (such as labeled avidin, antibodies or other specific binding agents) for some or all of the probes. In one embodiment, the kit includes probes and detection reagents suitable for multiplex ISH.

In one example, the kit also includes an antibody conjugate, such as an antibody conjugated to a label (e.g., an enzyme, fluorophore, or fluorescent nanoparticle). In some examples, the antibody is conjugated to the label through a linker, such as PEG, 6x-His, streptavidin, or GST.

D. Detectable Labels and Methods of Labeling

The probes disclosed herein may comprise one or more labels (e.g., at least 1 at least 2, at least 3, at least 4, at least 5, at least 6, etc.), for example to permit detection of the probe/nucleic acid sequence (or region) of interest. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or quantity (for example, gene copy number) of a target nucleic acid (to which the labeled uniquely specific nucleic acid molecule is bound or hybridized) in a sample. The disclosure is not limited to the use of particular labels, although examples are provided.

A label associated with one or more nucleic acid molecules (such as the disclosed probes) can be detected either directly or indirectly. A label can be detected by any known or yet to be discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies. Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2', 7'-difluorofluorescein (OREGON GREEN®); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates, which emit at approximately 617 nm (Heyduk and Heyduk, *Analyt. Biochem.*, 248:216-27, 1997; *J. Biol. Chem.*, 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Carlsbad, Calif.) and including the ALEXA FLUOR® series of dyes (for example, as described in U.S. Pat. Nos. 5,696,157, 6,130,101 and 6,716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912). In addition to the fluorochromes described above, a fluorescent label can be a fluorescent nanoparticle, such as a semiconductor nanocrystal, e.g., a quantum dot. Additional labels include, for example, radioisotopes (such as 3H), metal chelates such as DOTA and DPTA chelates of radioactive or paramagnetic metal ions like Gd3+, and liposomes.

Detectable labels that can be used with nucleic acid molecules (such as the disclosed probes) also include enzymes, for example horseradish peroxidase (HRP), alkaline phosphatase (AP), acid phosphatase, glucose oxidase, β-galactosidase, β-glucuronidase, or β-lactamase. Where the detectable label includes an enzyme, a chromogen, fluorogenic compound, or luminogenic compound can be used in combination with the enzyme to generate a detectable signal (numerous of such compounds are commercially available, for example, from Life Technologies). Particular examples of chromogenic compounds include diaminobenzidine (DAB), 4-nitrophenylphosphate (pNPP), fast red, fast blue, bromochloroindolyl phosphate (BCIP), nitro blue tetrazolium (NBT), BCIP/NBT, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, and tetrazolium violet.

Alternatively, an enzyme can be used in a metallographic detection scheme. For example, silver in situ hybridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate (See, for example, U.S. Pat. No. 7,632,652,). Metallographic detection methods also include using an oxido-reductase enzyme (such as horseradish peroxidase) along with a water soluble metal ion, an oxidizing agent and a reducing agent, again to form a detectable precipitate (See, for example, U.S. Pat. No. 6,670,113).

In non-limiting examples, the disclosed nucleic acid probes are labeled with dNTPs covalently attached to hapten molecules (such as a nitro-aromatic compound (e.g., 2,4-dinitrophenyl (DNP)), biotin, fluorescein, digoxigenin (DIG), etc.). Additional haptens suitable for labeling the disclosed probes include nitropyrazole, 3-hydroxyquinoxaline, thiazolesulfonamide, nitrocinnamic acid, rotenone, 7-(diethylamino)coumarin-3-carboxylic acid, benzodiazepine, or benzofuran haptens (See, e.g., International Pat. Publ. No. WO 2012/003476 incorporated herein by reference). Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955. Indeed, numerous labeled dNTPs are available commercially, for example from Life Technologies (Carlsbad, Calif.). A label can be directly or indirectly attached to a dNTP at any location on the dNTP, such as a phosphate (e.g., α, β or γ phosphate) or a sugar.

Detection of labeled nucleic acid molecules can be accomplished by contacting the hapten-labeled nucleic acid molecules bound to the genomic target nucleic acid with a primary anti-hapten antibody. In one example, the primary anti-hapten antibody (such as a mouse anti-hapten antibody) is directly labeled with an enzyme. In another example, a secondary anti-species antibody (such as a goat anti-mouse IgG antibody) conjugated to an enzyme is used for signal amplification. In chromogenic in situ hybridization CISH a chromogenic substrate is added, for SISH, silver ions and other reagents as outlined in the referenced patents/applications are added.

In some examples, a probe is labeled by incorporating one or more labeled dNTPs using an enzymatic (polymerization) reaction. For example, the disclosed nucleic acid probes (for example, incorporated into a plasmid vector) can be labeled by nick translation (using, for example, biotin, DNP, digoxigenin, etc.) or by random primer extension with terminal transferase (e.g., 3' end tailing). In some examples, the nucleic probe is labeled by a modified nick translation reaction where the ratio of DNA polymerase I to deoxyribonuclease I (DNase I) is modified to produce greater than 100% of the starting material. In particular examples, the nick translation reaction includes DNA polymerase I to DNase I at a ratio of at least about 800:1, such as at least 2000:1, at least 4000:1, at least 8000:1, at least 10,000:1, at least 12,000:1, at least 16,000:1, such as about 800:1 to 24,000:1 and the reaction is carried out overnight (for example, for about 16-22 hours) at a substantially isothermal temperature, for example, at about 16° C. to 25° C. (such as room temperature). If the probe is included in a probe set (for example, multiple plasmids, such as 2, 3, 4, 5, 6, 7, 8, 9, 10, or more plasmids), the plasmids may be mixed in an equal molar ratio prior to performing the labeling reaction (such as nick translation or modified nick translation).

In other examples, chemical labeling procedures can also be employed. Numerous reagents (including hapten, fluorophore, and other labeled nucleotides) and other kits are commercially available for enzymatic labeling of nucleic acids, including the disclosed nucleic acid probes. As will be apparent to those of skill in the art, any of the labels and detection procedures disclosed above are applicable in the context of labeling a probe, e.g., for use in in situ hybridization reactions. For example, the Amersham MULTIPRIME® DNA labeling system, various specific reagents and kits available from Molecular Probes/Life Technologies, or any other similar reagents or kits can be used to label the nucleic acids disclosed herein. In particular examples, the disclosed probes can be directly or indirectly labeled with a hapten, a ligand, a fluorescent moiety (e.g., a fluorophore or a semiconductor nanocrystal), a chromogenic moiety, or a radioisotope. For example, for indirect labeling, the label can be attached to nucleic acid molecules via a linker (e.g., PEG or biotin). Additional methods that can be used to label probe nucleic acid molecules are provided in U.S. Pat. No. 7,541,455.

E. Methods for In Situ Hybridization for Chromosome Enumeration

The present invention also features in situ hybridization (ISH) assays, e.g., bright-field ISH assays, for detection of a gene target and a chromosome (e.g., centromere target of a chromosome) using single-strand oligonucleotide probes. For example, a method comprises contacting a tissue sample with a control probe specific to a control region of a chromosome (e.g., chromosome 17), wherein the control probe is a single-stranded oligonucleotide probe labeled with at least one first label. The control probe may be configured to achieve a staining intensity of ≥2 and staining coverage of ≥50% of nuclei within 3 hours when applied to a control sample. The method further comprises hybridizing the control probe to the control region under conditions for a period of time less than about 3 hours (e.g., ≤about 2.5 hours, ≤about 2 hours, ≤about 1.5 hour, or ≤about 1 hour), rinsing the sample to remove unbound probe, and detecting the presence of the hybridized probe.

In some embodiments, the method further comprises contacting the tissue sample with a target probe specific to a target region (e.g., HER2) of the chromosome, wherein the target probe is a single-stranded oligonucleotide probe labeled with at least one second label.

In some embodiments, the method further comprises applying chromogenic detection reagents that recognize the first label and amplifying the signal associated with said first label. The method may feature the use of one or more probes (e.g., SEQ ID NOs: 3-16) or systems as described herein.

Genome-specific blocking DNA (such as human DNA, for example, total human placental DNA or Cot-1™ DNA) is usually included in a hybridization solution (such as for in situ hybridization) to suppress probe hybridization to repetitive DNA sequences or to counteract probe hybridization to highly homologous (frequently identical) off target sequences when a probe complementary to a human genomic target nucleic acid is utilized. In hybridization with standard probes, in the absence of genome-specific blocking DNA, an unacceptably high level of background staining (for example, non-specific binding, such as hybridization to non-target nucleic acid sequence) is usually present, even when a "repeat-free" probe is used. The disclosed nucleic acid probes exhibit reduced background staining, even in the absence of blocking DNA. In particular examples, the hybridization solution including the disclosed probes does not include genome-specific blocking DNA (for example, total human placental DNA or Cot-1™ DNA, if the probe is complementary to a human genomic target nucleic acid). This advantage is derived from the uniquely specific nature of the target sequences included in the nucleic acid probe; each labeled probe sequence binds only to the cognate uniquely specific genomic sequence. This results in dramatic increases in signal to noise ratios for ISH techniques.

As such, some methods herein may be free from the use of blocking DNA. However, in some embodiments, blocking DNA may be used. In some embodiments, an amount of blocking DNA is used but the amount of blocking DNA is sufficient to block out no more than a specified percent of the non-specific binding, e.g., no more than 50%, 40%, 30%, 20%, or 10%.

In order to determine an amount of blocking DNA that is sufficient to block out no more than a specified percent (e.g., 50%) of the non-specific binding, the following tests may be conducted. Set up an in situ hybridization assay, contact a tissue sample with a double strand control probe specific to a control region of a chromosome (in combination with zero to a serially, gradually increasing amount of blocking DNA); hybridize the double strand control probe to the control region; rinse the sample to remove unbound double strand probe; and detect the presence of the hybridized probe. Then observe the amount of background that is blocked by the serially increasing blocking DNA in each assay. The amount of blocking DNA that achieves a specified percent of the blocking of the background corresponds to the amount of blocking DNA that is sufficient to block out no more than a specified percent (e.g., 50%) of the non-specific binding. For example, the amount of blocking DNA that achieves blocking out 50% of percent of the background corresponds to the amount of blocking DNA that is sufficient to block out no more than 50% of the non-specific binding.

In some embodiments, said amount of blocking DNA is between about 1 pg/ml to 1 mg/ml. In some embodiments, said amount of blocking DNA is between about 1 pg/ml to 0.5 mg/ml. In some embodiments, said amount of blocking DNA is between about 1 pg/ml to 0.25 mg/ml. In some embodiments, said amount of blocking DNA is between about 1 pg/ml to 1 µg/ml.

In some illustrative embodiments, methods for obtaining two bright-field chromogenic in situ hybridization signals per cell may comprise contacting a tissue sample containing a plurality of cells with a control probe specific to a control region of a single chromosome, the probe selected so as to not evidently bind non-specifically in the absence of blocking DNA; hybridizing the control probe to the control region of said chromosome; rinsing the sample to remove unbound probe; and detecting the presence of the hybridized probe via a chromogenic reagent so as to generate two bright-field chromogenic in situ hybridization signals per cell. In order to determine that the selected probe does not evidently bind non-specifically in the absence of blocking DNA, a comparative assay (Assay 2) may be conducted along side with the aforementioned assay (Assay 1), wherein the same selected probe is employed in both Assay 1 and Assay 2. Assay 1 is free of the blocking DNA and Assay 2 employs a blocking DNA. Then the respective data of the two assays are compared. The selected probe does not evidently bind non-specifically in the absence of blocking DNA when the data of the two respective assays are the same or substantially the same.

In some examples the hybridization solution may contain carrier DNA from a different organism (for example, salmon sperm DNA or herring sperm DNA, if the genomic target nucleic acid is a human genomic target nucleic acid) to reduce non-specific binding of the probe to non-DNA materials (for example to reaction vessels or slides) with high net positive charge which can non-specifically bind to the negatively charged probe DNA.

Methods of the present invention may comprise detecting signals wherein more than 50% of the nuclei of the tissue sample have enumerable signals for said chromosome, wherein an enumerable signal is a generally round shape (e.g., as described above). In some embodiments, background signals are not observed in >70% of cells of the tissue sample. In some embodiments, background signals are not observed in >80% of cells of the tissue sample. In some embodiments, background signals are not observed in >90% of cells of the tissue sample. In some embodiments, background signals are present but are sufficiently weak in intensity so as to permit identification of enumerable signals in >50% of the nuclei.

In some embodiments, more than 60% of the nuclei have enumerable chromosome signals. In some embodiments, more than 70% of the nuclei have enumerable chromosome signals. In some embodiments, the inner radius is no less than 60% of the outer radius. In some embodiments, the inner radius is no less than 75% of the outer radius. In some embodiments, the inner radius is no less than 90% of the outer radius.

In situ hybridization (ISH) involves contacting a sample containing a target nucleic acid (e.g., a genomic target nucleic acid) in the context of a metaphase or interphase chromosome preparation (such as a cell or tissue sample mounted on a slide) with a labeled probe specifically hybridizable or specific for the target nucleic acid (for example, one or more of the probes disclosed herein). The slides are optionally pretreated, e.g., to remove paraffin or other materials that can interfere with uniform hybridization. The chromosome sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the target is performed using standard techniques.

For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin. Amplification of the FITC signal can be effected, if necessary, by incubation with biotin-conjugated goat anti-avidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). The enzyme reaction can be performed in, for example, AP buffer containing NBT/BCIP and stopped by incubation in 2×SSC. For a general description of in situ hybridization procedures, see, e.g., U.S. Pat. No. 4,888,278, the disclosure of which is incorporated in its entirety herein by reference.

Numerous procedures for FISH, CISH, and SISH are known in the art. For example, procedures for performing FISH are described in U.S. Pat. Nos. 5,447,841; 5,472,842; and 5,427,932; CISH is described in U.S. Pat. No. 6,942,970, and additional detection methods are provided in U.S. Pat. No. 6,280,929, the disclosures of which are incorporated in their entirety herein by reference.

Numerous reagents and detection schemes can be employed in conjunction with FISH, CISH, and SISH procedures to improve sensitivity, resolution, or other desirable properties. As discussed above, probes labeled with fluorophores (including fluorescent dyes and quantum dots) can be directly optically detected when performing FISH. Alternatively, the probe can be labeled with a non-fluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., quantum dot) or with another indirectly detectable moiety, or can be contacted with one or more additional specific binding agents (e.g., secondary or specific antibodies), which can in turn be labeled with a fluorophore. Optionally, the detectable label is attached directly to the antibody, receptor (or other specific binding agent).

Alternatively, the detectable label is attached to the binding agent via a linker, such as a hydrazide thiol linker, a polyethylene glycol linker, or any other flexible attachment moiety with comparable reactivities. For example, a specific binding agent, such as an antibody, a receptor (or other anti-ligand), avidin, or the like can be covalently modified with a fluorophore (or other label) via a heterobifunctional polyalkyleneglycol linker such as a heterobifunctional polyethyleneglycol (PEG) linker. A heterobifunctional linker combines two different reactive groups selected, e.g., from a carbonyl-reactive group, an amine-reactive group, a thiol-reactive group and a photo-reactive group, the first of which attaches to the label and the second of which attaches to the specific binding agent.

In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2007/0117153, the disclosures of which are incorporated in their entirety herein by reference.

In further examples, a signal amplification method is utilized, for example, to increase sensitivity of the probe. For example, tyramide signal amplification may be utilized (See U.S. Pat. No. 5,196,306, the disclosures of which are incorporated in their entirety herein by reference). In one variation of this method a biotinylated nucleic acid probe detects the presence of a target by binding thereto. Next a streptavidin-peroxidase conjugate is added. The streptavidin binds to the biotin. A substrate of biotinylated tyramide (tyramine is 4-(2-aminoethyl)phenol) is used, which presumably becomes a free radical when interacting with the peroxidase enzyme. The phenolic radical then reacts quickly with the surrounding material, thus depositing or fixing biotin in the vicinity. This process is repeated by providing more substrate (biotinylated tyramide) and building up more localized biotin. Finally, the "amplified" biotin deposit is detected with streptavidin attached to a fluorescent molecule. Alternatively, the amplified biotin deposit can be detected with avidin-peroxidase complex, that is then fed 3,3'-diaminobenzidine to produce a brown color. It has been found that tyramide attached to fluorescent molecules also serve as substrates for the enzyme, thus simplifying the procedure by eliminating steps. Yet another amplification approach is described in U.S. Patent Publ. No. 2013/0260379, the disclosures of which are incorporated in their entirety herein by reference.

In other examples, the signal amplification method utilizes branched DNA (bDNA) signal amplification. In some examples, target-specific oligonucleotides (label extenders and capture extenders) are hybridized with high stringency to the target nucleic acid. Capture extenders are designed to hybridize to the target and to capture probes, which are attached to a microwell plate. Label extenders are designed to hybridize to contiguous regions on the target and to provide sequences for hybridization of a preamplifier oligonucleotide. Signal amplification then begins with preamplifier probes hybridizing to label extenders. The preamplifier forms a stable hybrid only if it hybridizes to two adjacent label extenders. Other regions on the preamplifier are designed to hybridize to multiple bDNA amplifier molecules that create a branched structure. Finally, alkaline phosphatase (AP)-labeled oligonucleotides, which are complementary to bDNA amplifier sequences, bind to the bDNA molecule by hybridization. The bDNA signal is the chemiluminescent product of the AP reaction (See, e.g., Tsongalis, *Microbiol. Inf Dis.,* 126:448-453, 2006; U.S. Pat. No. 7,033,758, the disclosures of which are incorporated in their entirety herein by reference).

In further examples, the signal amplification method utilizes polymerized antibodies. In some examples, the labeled probe is detected by using a primary antibody to the label (such as an anti-DIG or anti-DNP antibody). The primary antibody is detected by a polymerized secondary antibody (such as a polymerized HRP-conjugated secondary antibody or an AP-conjugated secondary antibody). The enzymatic reaction of AP or HRP leads to the formation of strong signals that can be visualized.

It will be appreciated by those of skill in the art that by appropriately selecting labeled probe-specific binding agent pairs, multiplex detection schemes can be produced to facilitate detection of multiple target nucleic acids (e.g., genomic target nucleic acids) in a single assay (e.g., on a single cell or tissue sample or on more than one cell or tissue sample). For example, a first probe that corresponds to a first target nucleic acid can be labeled with a first hapten, such as biotin, while a second probe that corresponds to a second target nucleic acid can be labeled with a second hapten, such as DNP. Following exposure of the sample to the probes, the bound probes can be detected by contacting the sample with a first specific binding agent (in this case avidin labeled with a first fluorophore, for example, a first spectrally distinct quantum dot, e.g., that emits at 585 nm) and a second specific binding agent (in this case an anti-DNP antibody, or antibody fragment, labeled with a second fluorophore (for example, a second spectrally distinct quantum dot, e.g., that emits at 705 nm)). Additional probes/binding agent pairs can be added to the multiplex detection scheme using other spectrally distinct fluorophores. Numerous variations of direct, and indirect (one step, two step or more) can be envisioned, all of which are suitable in the context of the disclosed probes and assays.

Additional details regarding certain detection methods, e.g., as utilized in CISH and SISH procedures, can be found in Bourne, The Handbook of Immunoperoxidase Staining Methods, published by Dako Corporation, Santa Barbara, Calif.

Difficulties frequently encountered in ISH testing may result from the manner in which the tissues are typically preserved. The mainstay of the diagnostic pathology laboratory has been for many decades the formalin-fixed, paraffin-embedded block of tissue, sectioned and mounted upon glass slides. Fixation in such a preservative causes cross-linking of macromolecules, both amino acids and nucleic acids. These cross-linked components must be removed to allow access of the probe to the target nucleic acid and to allow the antibody to recognize the corresponding antigen. "Unmasking" the antigen and/or nucleic acid is typically accomplished manually with multiple pretreatment, proteolytic digestion, and wash steps. Prior to or staining, complete removal of the paraffin is also required so that it does not interfere with antibody or probe binding. Deparaffinization may be achieved by the use of multiple (e.g., two or three) successive clearing reagents that are paraffin solvents (e.g., xylene, xylene substitutes, or toluene).

In some embodiments, preparing the sample includes the step of cell conditioning. Cell conditioning is discussed in greater detail in U.S. Pat. No. 6,855,552, Towne, et al. "Automated immunohistochemical and in situ hybridization assay formulations", the subject matter of which is expressly incorporated by reference. In illustrative cell conditioning steps, a cell conditioning reagent is applied and the sample is contacted at the appropriate temperature for an appropriate duration of time so that the antigens and/or nucleic acid targets are sufficiently expressed for detection. One aspect of the present disclosure is that the automated instrument can automatically adjust the cell conditioning duration and/or temperature in response to the user inputs. Cell conditioning may further include applying a protease reagent. Illustratively, a protease treatment may involve the step of contacting a protease solution to a biological sample. The protease treatment, as with cell conditioning, is intended to increase the expression of target antigens and/or nucleic acids.

Cell conditioning reagents such as ethylenediaminetetraacetic acid (EDTA) for nucleic acid targets (ISH) may be used. The contacting may be done at a temperature of about 95° C. for between about 2 and about 90 minutes. A partial list of possible reagents appears in Analytical Morphology, Gu, ed., Eaton Publishing Co. (1997) at pp. 1-40. Sodium dodecyl sulfate (SDS) and/or ethylene glycol may be included in the conditioning solution. Furthermore, metal ions or other materials may be added to these reagents to increase effectiveness of the cell conditioning. Exemplary cell conditioning solutions are available from Ventana Medical Systems, Inc., Tucson, Ariz. (Cell Conditioning 1 (CC1) catalog #: 950-124; Cell Conditioning 2 (CC2) catalog #: 950-123; SSC (10×) catalog #: 950-110; ULTRA Cell Conditioning (ULTRA CC1) catalog #: 950-224; ULTRA Cell Conditioning (ULTRA CC2) catalog #: 950-223, Protease 1 catalog #: 760-2018; Protease 2 catalog #: 760-2019; Protease 3 catalog #: 760-2020). In some embodiments, applying the in situ hybridization binding reagent occurs subsequent to applying the cell conditioning reagent and prior to applying the chromogenic reagent.

In illustrative embodiments, the method includes applying a rinsing reagent. Between various steps described herein and as part of the system described herein, rinse steps may be added to remove unreacted residual reagents from the prior step. Rinse steps may further include incubations, which include maintaining a rinsing reagent on the sample for a pre-determined time at a pre-determined temperature with or without mixing. The conditions appropriate for the rinsing steps may be distinct between the various steps. Exemplary rinsing reagents are available from Ventana Medical Systems, Inc., Tucson, Ariz. (Reaction Buffer (10×) catalog #: 950-300; Special Stains Wash (10×) catalog #: 860-015).

Exemplary automated systems available through Ventana Medical Systems, Inc., Tucson, Ariz. include SYMPHONY® Staining System, catalog #: 900-SYM3, VENTANA® BenchMark Automated Slide Preparation Systems, catalog #s: N750-BMKXT-FS, N750-BMKU-FS, VENTANA, and VENTANA® BenchMark Special Stains automated slide stainer. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

While the present invention describes a single-stranded oligonucleotide-based HER2/CHR17 dual ISH assay, it is understood that those of ordinary skill in the art could apply the discoveries disclosed herein to other gene/centromere combination of interest.

In some embodiments, the disclosed systems (e.g., probes) can be used in methods of determining the copy number of a target nucleic acid (such as HER2) in a biological sample (such as a tissue sample). Methods of determining the copy number of a gene or chromosomal region are well known to those of skill in the art. In some examples, the methods include in situ hybridization (such as fluorescent, chromogenic, or silver in situ hybridization), comparative genomic hybridization, or polymerase chain reaction (such as real-time quantitative PCR). In some examples, methods of determining gene copy number include counting the number of ISH signals (such as fluorescent, colored, or silver spots) for the target nucleic acid in one or more individual cells. The methods may also include counting the number of ISH signals (such as fluorescent, colored, or silver spots) for a reference (such as a chromosome-specific probe) in the cells. In particular examples, the number of copies of the gene (or chromosome) may be estimated by the person (or computer, in the case of an automated method) scoring the slide. In some examples, an increased copy number relative to a control (such as an increase of about 1.5-fold, 2-fold, 3-fold, 5-fold, 10-fold, 20-fold, or more relative to a control sample or reference value) indicates an increase in the target nucleic acid copy number.

In some examples, the method includes counting the number of copies per cell or nucleus of a reference, such as a chromosomal locus known not to be abnormal, for example a centromere. In some examples, the reference is on the same chromosome as the gene of interest. Exemplary reference chromosomes that can be used for particular human genes of interest are provided in TABLE 2. In particular examples, the reference locus is detected by using a centromere-specific probe. Such probes are known in the art and are commercially available, for example, Vysis CEP probes (Abbott Molecular, Des Plaines, Ill.) and SPOT-LIGHT centromeric probes (Invitrogen, Carlsbad, Calif.). In some examples, a ratio of target nucleic acid copy number to reference copy number greater than about two (such as greater than about 2, 3, 4, 5, 10, 20, or more) indicates an increase in the target nucleic acid copy number.

TABLE 2

Exemplary reference chromosomes for particular target nucleic acids

| Target Nucleic Acid | Reference Chromosome |
|---|---|
| PTEN | 10 |
| HER2 | 17 |
| PIK3CA | 3 |
| TOP2A | 17 |
| MET | 7 |
| MDM2 | 12 |

F. Methods of Scoring

The present invention also features methods of scoring gene copy number of a target region and optionally comparing it to the copy number of a control region. For additional methods of scoring, which may be used with the methods described herein, reference is made to U.S. Publ. Appl. No. 2012/0141472, which is hereby incorporated by reference for disclosure related to scoring ISH.

In some examples, an increased gene copy number includes the gene copy number per nucleus (such as average gene copy number per nucleus) in the sample of greater than about two copies of the gene per nucleus (such as greater than 2, 3, 4, 5, 10, or 20 copies). In other examples, an increased gene copy number includes a ratio of gene copy number to its corresponding chromosome copy number (such as an average gene:chromosome ratio) in the sample of greater than about 2 (such as a ratio of greater than 2, 3, 4, 5, 10, or 20). In further examples, an increased gene copy number includes an increase in gene copy number relative to a control (such as an increase of about 1.5-fold, about 2-fold, about 3-fold, about 5-fold, about 10-fold, about 20-fold, or more). Therefore, in some examples, the method includes comparing the gene copy number in the sample from the subject to the gene copy number in a control or a reference value or range of values expected for the gene copy number in an appropriate normal tissue.

Also disclosed herein is a method of scoring (for example, enumerating) copy number of a gene in a sample from a subject, wherein the sample is stained by ISH (such as FISH, SISH, CISH, or a combination of two or more thereof) for the gene of interest and wherein individual copies of the gene are distinguishable in cells in the sample. In particular examples, the sample is a biological sample from a subject, such as a tumor sample (for example, a tumor biopsy). Methods of determining gene copy number by ISH are well known in the art.

In some embodiments, the method includes identifying individual cells in a sample with the highest number of signals per nucleus for the gene (such as the strongest signal in the sample), counting the number of signals for the gene in the identified cells, and determining an average number of signals per cell, thereby scoring the gene copy number in the sample. In additional embodiments, the method further includes counting the number of signals for a reference (such as a chromosomal locus known not to be abnormal, for example, centromeric DNA) and determining an average ratio of the number of signals for the gene to the number of signals for the reference per cell.

The scoring method may include identifying individual cells in the sample (such as a tissue section or tumor core) having the highest number of signals (such as the highest number of spots per cell or the brightest intensity of staining) for the gene of interest in the cells in the sample. Thus, the disclosed method may not determine gene copy number in a random sampling of cells in the sample. Rather, the method may include specifically counting gene copy number in those cells that have the highest gene copy number in the sample. In some examples, identifying the individual cells having the highest number of signals for the gene includes examining a sample stained by ISH for the gene under low power microscopy (such as about 20×magnification). Cells with the strongest signal (for example, highest amplification signal under higher power) are identified for counting by eye or by an automated imaging system. In some examples, such as when the sample is a tissue section, the sample is examined (for example, visually scanned) to identify a region that has a concentration of tumor cells that has amplification of the gene. Gene copy number in the cells with highest amplification in the selected region is then counted. In other examples, such as when the sample is a tumor core (such as a tumor microarray), most of the sample is visible in the field of view under low power magnification and the individual cells (such as tumor cells) with the strongest signal (for example, highest amplification signal under high power) are separately identified for counting. In particular examples, the cells chosen for counting the gene copy number may be non-consecutive cells, such as cells that are not adjacent to or in contact with one another. In other examples, at least some of the cells chosen for counting the gene copy number may be consecutive cells, such as cells that are adjacent to or in contact with one another.

The disclosed methods may include counting the number of ISH signals (such as fluorescent, colored, or silver spots) for the gene in the identified cells. The methods may also include counting the number of ISH signals (such as fluorescent, colored or silver spots) for a reference (such as a chromosome-specific probe) in the identified cells. In some examples, the number of spots per cells is distinguishable in the identified cells and the number of spots are counted (or enumerated) and recorded. In other examples, one or more of the identified cells may include a cluster, which is the presence of multiple overlapping signals in a nucleus that cannot be counted (or enumerated). In particular examples, the number of copies of the gene (or chromosome) may be estimated by the person (or computer, in the case of an automated method) scoring the slide. For example, one of skill in the art of pathology may estimate that a cluster contains a particular number of copies of a gene (such as 10, 20, or more copies) based on experience in enumerating gene copy number in a sample. In other examples, the presence of a cluster may be noted as a cluster, without estimating the number of copies present in the cluster.

The number of cells identified for counting is a sufficient number of cells that provides for detecting a change (such as an increase or decrease) in gene copy number. In some examples, the number of cells identified for counting is at least about 20, for example, at least 25, 30, 40, 50, 75, 100, 200, 500, 1000 cells, or more. In a particular example, about 50 cells are counted. In other examples, every cell in the sample or every cell in a microscope field of vision, or in a number of microscope fields (such as at least 2 microscope fields, at least 3, at least 4, at least 5, at least 6 microscope fields, and the like) which contains 3 or more copies of the gene of interest (such as 3, 4, 5, 6, 7, 8, 9, 10, 15, 20, or more) is counted.

Methods may feature obtaining a sample having undergone ISH according to methods disclosed herein. An area of neoplastic nuclei with the most copy numbers is identified and the enumerable signals for the chromosome/target are counted in 50-100 neoplastic nuclei and either 50 adjacent mesenchymal nuclei or 50 adjacent normal epithelial nuclei.

Scoring criteria may be as follows: no staining or <1 dot/10 cells is scored as 0; 1-3 dots/cell is scored as 1; 4-9 dots/cell, none or very few dot clusters is scored as 2; 10-15 dots/cell and <10% dots are in clusters is scored as 3; and >15 dots/cell and >10% dots are in clusters is scored as 4.

In some embodiments, the average number of target signals (e.g., HER2) per nuclei is calculated. In some embodiments, the average number of chromosome (e.g., CHR17) copies per nuclei is calculated. In some embodiments, the target signal to chromosome signal ratio is calculated.

The disclosure is further illustrated by the following non-limiting Examples.

EXAMPLES

Example 7

A. Specimens

Breast tissue samples were utilized for developing and optimizing the single strand oligonucleotide HER2 and/or CHR17 single and dual ISH assays. Samples were obtained from a tissue specimen archive maintained at Ventana Medical Systems, Inc. (Tucson, Ariz.). These samples were redundant clinical specimens that had been de-identified and unlinked from patient information and therefore patient informed consent was not required (6). Paraffin sections (4 μm) containing tissue cores of formalin-fixed, paraffin-embedded breast tissue were placed onto SUPERFROST Plus glass slides.

B. Probes

INFORM HER2 DUAL ISH DNA Probe reagent includes a probe dispenser that contains 12 μg/ml of dinitrophenyl (DNP)-labeled HER2 probe cocktailed with a digoxigenin-labeled (DIG) Chr17 probe with 4 mg/ml human blocking DNA in a formamide-based buffer.

The single strand oligonucleotide HER2 probe (HER2 oligonucleotide probe) is a dinitrophenyl (DNP)-labeled, repeat-free genomic probe specifically targeting the HER2 gene region. Similar to INFORM HER2 DUAL ISH DNA Probe, the HER2 oligonucleotide probe spans >327,000 nucleotides (nt) (35,027,979-35,355,516) of genomic DNA from human Chromosome 17, encompassing the HER2 target region (UCSC Genome Browser on Human May 2004 (NCBI35/hg17) Assembly). The HER2 oligonucleotide sequences were designed from the sequences in INFORM HER2 DUAL ISH DNA Probe. Each of the HER2 oligonucleotides was designed with 80-mer length; hence stringency level for non-target binding was raised higher according to the aforementioned oligonucleotide probe design criteria. Specificity of the HER2 oligonucleotide probe was experimentally validated on metaphase spreads under the examined ISH assay conditions.

Bioinformatic searches were used to identify HER2 specific nucleic acid sequences around the HER2 target region. The selected genomic target nucleic acid sequence is separated into consecutive non-overlapping 80 nt segments. One thousand one hundred and ninety-six (1196) ~80mer oligonucleotides were synthesized each carrying 5 DNP haptens on an abasic phosphoramidite spaced 20 nt apart. A representative structure for these oligonucleotides is shown in FIG. 1(A)-(B). The bolded portion of FIG. 1(A), also SEQ. ID NO: 1, is shown in more detail in FIG. 1(B). The oligonucleotides were affinity purified and analyzed by mass spectrometry and gel electrophoresis. HER2 oligonucleotide probe was bulked in a formamide-based buffer without human blocking DNA. In the initial screening process, the number of oligonucleotides, the number and spacing of DNP haptens were functionally tested in the formamide-based buffer without human blocking DNA for sensitivity and specificity to HER2 gene.

The double-stranded HER2 probe (HER2 ds probe) was DNP-labeled with the same HER2 DNA template in the INFORM HER2 DUAL ISH DNA Probe. HER2 ds probe was formulated with 4 mg/ml human blocking DNA in the formamide-based buffer. HER2 ds probe was only used in the single ISH assay.

The above-mentioned commercial product INFORM HER2 DUAL ISH DNA contains a dispenser containing 0.75 ug/ml of a DIG-labeled Chr17 probe cocktailed with the DNP-labeled HER2.

Figures 2A, 2B:
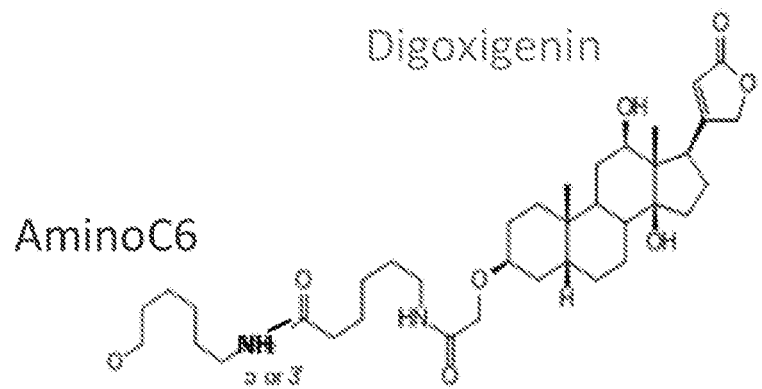
FIG. 2(A-C) is a sequence (SEQ. ID. NO: 2) and structural perspectives of a disclosed probe.
Figure 2C:
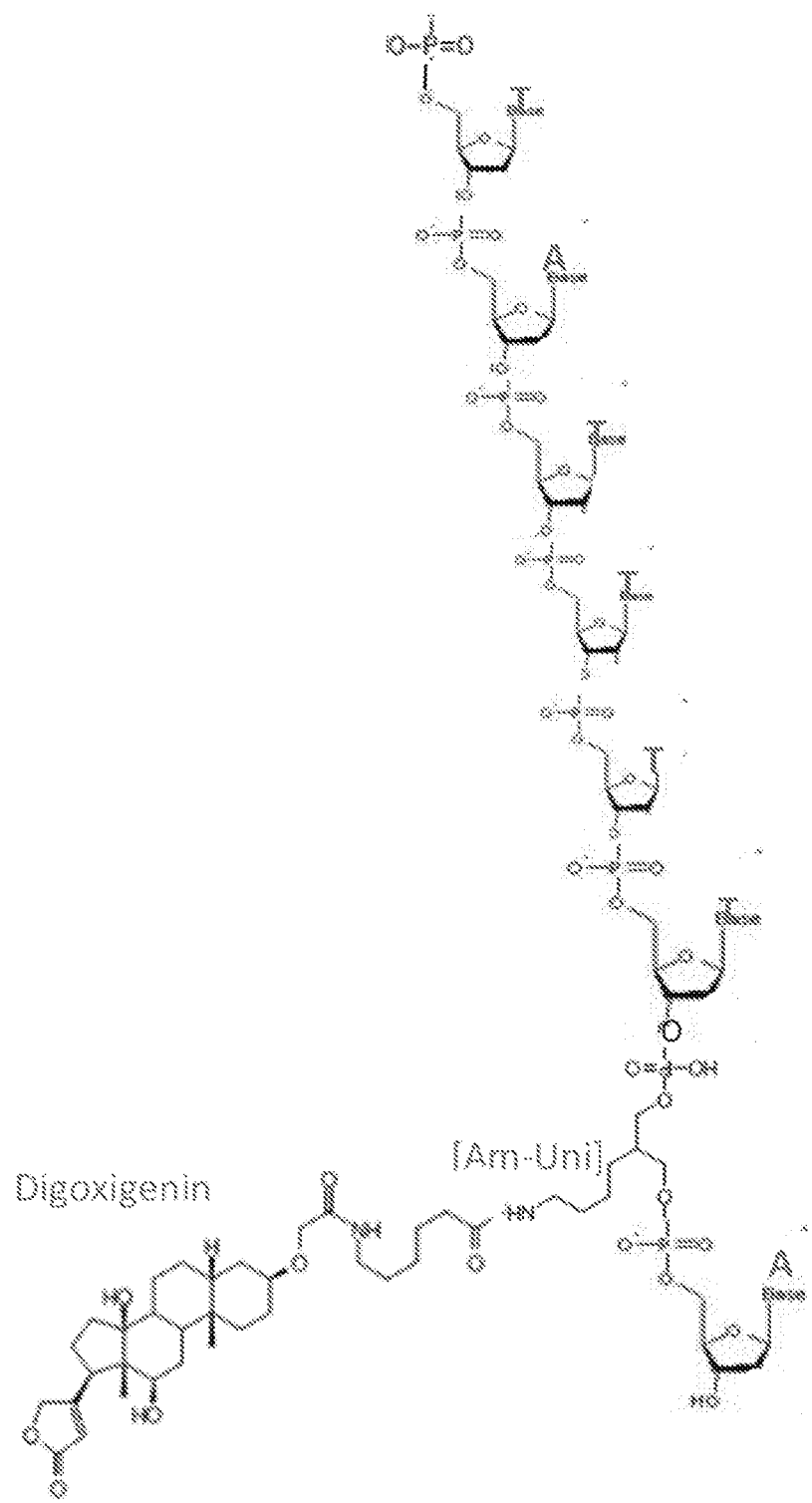

A single strand oligonucleotide Chr17 probe (Chr17 oligonucleotide probe) was made with a pool of 14 oligonucleotides with lengths from 58 bp to 87 bp. Each oligonucleotide was labeled with two DIG hapten molecules on a non-binding tail having the sequence TATTTTTATTTT at its 5' end (See FIG. 2(A)-(C), wherein FIG. 2(A) shows an exemplary Chr17 probe sequence (SEQ. ID. NO: 2) including the 5' tail and FIG. 2(B) shows a more detailed structure of the aminoC6+Dig bolded region of FIG. 2(A) and FIG. 2(B) shows a more detailed structure of the Am~Uni+Dig bolded region. These oligonucleotides were PAGE purified and analyzed with mass spectrometry. The Chr17 oligonucleotide probe was formulated in a formamide-based buffer without human blocking DNA. In the initial screening process, a total of 28 oligonucleotides were tested for specificity to the chromosome 17 centromere. They were individually formulated in the formamide-based buffer without human blocking DNA for this initial screening as a pool for testing as a DISH assay. HER2 oligonucleotide probe (15 µg/ml) and CHR17 oligonucleotide probe (0.5 µg/ml) were formulated in the formamide-based buffer without human blocking DNA. In illustrative embodiments, the Chr 17 probe comprises one or more of the sequences listed in TABLE 3.

TABLE 3

Chromosome 17 probe sequences

| Oligo name | Sequences | Length |
|---|---|---|
| CHR17_M1.1<br>SEQ ID. NO: 3 | AATTCGTTGGAAACGGGATAATTTCAGCTGACTAAACAGAAGCA<br>GTCTCAGAATCTTCTTTGTGATGTTTGCATTCAAA | 79 |
| CHR17_M2.1<br>SEQ ID. NO: 4 | CTTCGTTCGAAACGGGTATATCTTCACATGCCATCTAGACAGAA<br>GCATCCTCAGAAGCTTCTCTGTGATGACTGCATTC | 79 |
| CHR17_M2.2<br>SEQ ID. NO: 5 | TGAACTCTCCTTTTGAGAGCGCAGTTTTGAAACTCTCTTTCTGT<br>GGCATCTGCAAGGGGACATGTAGACCTCTTTGAAG | 79 |
| CHR17_M3.1<br>SEQ ID. NO: 6 | TTTCGTTGGAAACGGAATCATCTTCACATAAAAACTACACAGAT<br>GCATTCTCAGGAACTTTTTGGTGATGTTTGTATTC | 79 |
| CHR17_M5.1<br>SEQ ID. NO: 7 | CCTATGGTAGTAAAGGGAATAGCTTCATAGAAAAACTAGACAGA<br>AGCATTCTCAGAAAATACTTTGTGATGATTGAGTTTAAC | 83 |
| CHR17_M5.2<br>SEQ ID. NO: 8 | CACAGAGCTGAACATTCCTTTGGATGGAGCAGGTTTGAGACACT<br>CTTTTTGTACAATCTACAAGTGGATATTTGGACCTCTCTGAGG | 87 |
| CHR17_M8.2<br>SEQ ID. NO: 9 | GTTTCACATTGCTTTTCATAGAGTAGTTCTGAAACATGCTTTTC<br>GTAGTGTCTACAAGTGGACATTTGGAG | 71 |
| CHR17_M9.1<br>SEQ ID. NO: 10 | CCTGTGGTGGAAAACGAATTATCGTCACGTAAAAACTAGAGAGA<br>AGCATTGTCAGAAA | 58 |
| CHR17_M9.2<br>SEQ ID. NO: 11 | TGCATTCAACTCACAGAGTTGAAGGTTCCTTTTCAAAGAGCAGT<br>TTCCAATCACTCTTTGTGTGG | 65 |
| CHR17_M11.2<br>SEQ ID. NO: 12 | CATTCCCTTTGACAGAGCAGTTTGGAAACTCTCTTTGTGTAGAA<br>TCTGCAAGTGGAGATATGGACCGCTTT | 71 |
| CHR17_M12.1<br>SEQ ID. NO: 13 | CCTATGGTAGTAAAGGAAATAGCTTCATATAAAAGCTAGACAGT<br>AGCATTCACAGAAAACTCTTGGTGACGACTGAGTTT | 80 |
| CHR17_M13.1<br>SEQ ID. NO: 14 | ATTTCGTTGGAAACGGGATAAACCGCACAGAACTAAACAGAAG<br>CATTCTCAGAACCTTCTTCGTGATGTTTGCATTCAAC | 80 |
| CHR17_M16.1<br>SEQ ID. NO: 15 | CGTAGTAAAGGAAATAACTTCCTATAAAAAGAAGACAGAAGCTT<br>TCTCAGAAAATTCTTTGGGATGATTGAGTTGAACTC | 80 |
| CHR17_M16.2<br>SEQ ID. NO: 16 | ACAGAGCTGAGCATTCCTTGCGATGTAGCAGTTTAGAAACACAC<br>TTTCTGCAGAATCTGCAATTGCATATTTGGACCTT | 80 |

C. Automated Bright-Field In Situ Hybridization for Interphase Slides

The BenchMark ULTRA automated slide processing system (Ventana Medical Systems, Inc., Tucson, Ariz.) was used for the discovering and performance evaluation of the single strand oligonucleotide HER2 and/or CHR17 single and dual ISH assays for HER2 and CHR17 DNA targets. The FDA-approved INFORM HER2 DUAL ISH DNA Probe Assay protocol was used for tissue staining. A modification was introduced for shorter hybridization times (i.e. 16 min, 32 min and 1 hr). In certain testing scenarios, the single strand oligonucleotide HER2 and/or Chr17 probes were used in the over-labeled INFORM HER2/Chr17 probe dispenser. INFORM HER2 DUAL ISH DNA Probe Assay reagents include dinitrophenyl (DNP)-labeled HER2 and digoxigenin-labeled (DIG) Chr17 probe cocktails, the ultraView SISH and ultraView Alkaline Phosphatase Red ISH detection kits (Ventana Medical Systems, Inc.). The slides were deparaffinized at 69° C., followed by incubation with pH 6 citrate buffer at 82° C. and by digestion by ISH Protease 3 for 20 minutes. The probe(s) were first denatured for 8 minutes at 80° C., then hybridized for a set-up time (6 hours is the default for the FDA-approved protocol) at 44° C., followed by 3 stringency washes with pH 6.0 citrate buffer at 72° C. After the application of a horseradish peroxidase-labeled rabbit anti-DNP antibody linker, the specific hybridization of the DNP-linked HER2 probe to its target was visualized by an insoluble precipitate of silver chromogen. After the application of an alkaline phosphatase-labeled mouse anti-digoxigenin antibody linker, the visualization of digoxigenin-linked Chr17 probe was detected by the soluble precipitate of the alkaline phosphatase-based Fast Red chromogenic system. For visualizing the complete morphology of the tissue, the slides were counterstained with hematoxylin for 4 minutes and post-counterstained with bluing reagent for 4 minutes.

D. Automated Bright-Field Chromosome Metaphase Spread ISH Staining:

Metaphase chromosomes (CGH Metaphase Target Slides, Abbott Molecular) were UV crosslinked on Stratalinker 2400 (Stratagene Model #C00518) at energy level 200 mJ. They were then treated with 1% trypsin (Sigma cat #T1426) at room temperature for 5 s. The slides were then processed for ISH staining under the same conditions as described above except skipping steps for baking, deparaffin, cell conditioning and counterstaining. After the staining is completed on the instrument, slides were stained with 4% Giemsa (Gibco, cat #10092-03) diluted in Gurr buffer (Gibco, cat #10582-013) at room temperature for 5 min, and the staining was visualized with a regular light microscope.

E. Analytical Slide Scoring Criteria:

A board-certified pathologist (P. B.) with experience on interpreting HER2/Chr17 DISH stained slides reviewed and scored the slides. Each slide was scored for signal intensity and background. The analytical slide scoring criteria (TABLE 1) describe the "Acceptable" or "Not Acceptable" staining. The "Acceptable" or "Not Acceptable" criteria are corresponding to the capability whether the HER2 or the Chr17 pairs of signals are enumerable in 20 cells on a slide. The scoring criteria were developed and used as a stringent analytical tool for the purpose of assay optimization.

F. Signal Enumeration of HER2 and Chr17

Once an adequate target area was identified, the reader recorded the scores for HER2 and Chr17 copy numbers that were present in 20 representative nuclei. If the resulting HER2/Chr17 ratio falls within 1.8-2.2, the reader is recommended to score an additional 20 nuclei and the resulting ratio is calculated from the total 40 nuclei. HER2 gene status is reported as non-amplified (HER2/Chr17<2.0) or amplified (HER2/Chr17>2.0). Reference is made to Interpretation Guide Ventana INFORM HER2 Dual ISH DNA Probe Cocktail Assay, which is hereby incorporated by reference herein in its entirety for disclosure related to the assay.

Figure 3A:
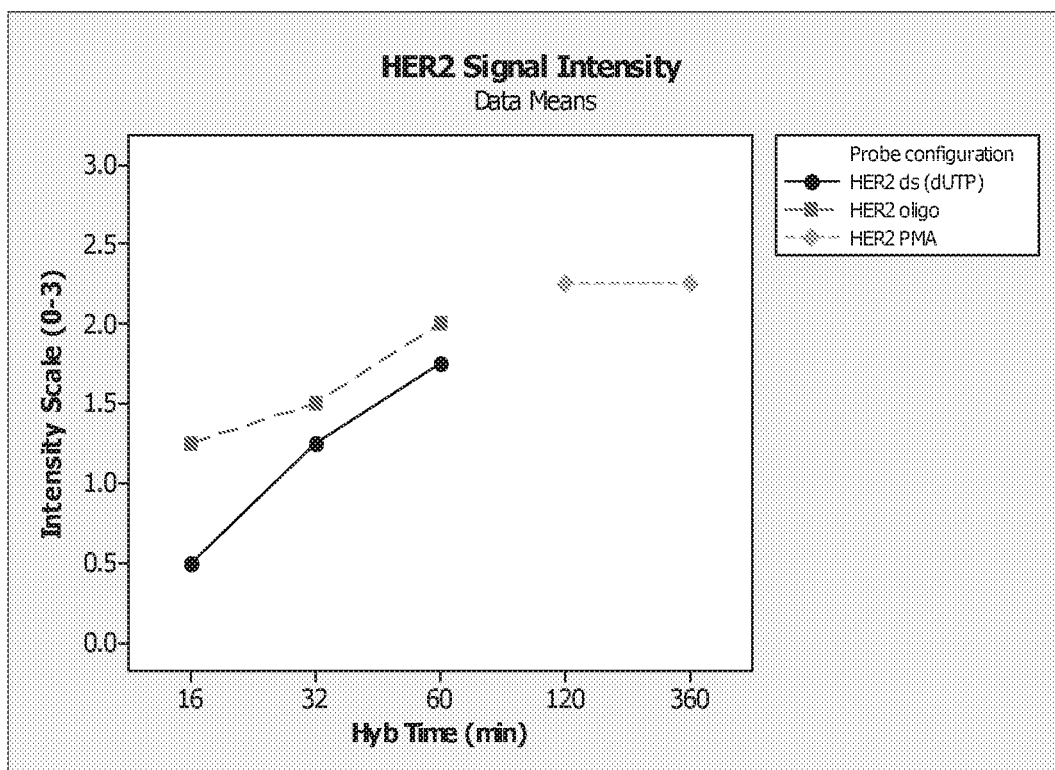
FIG. 3(A-D) are graphs (A) and (B) and photomicrographs (C) and (D) which show HER2 signal intensity and coverage for probes as disclosed herein compared to a commercially available probe (labeled HER2PMA).

G. HER2 Oligonucleotide Probe Performance Evaluation:

HER2 oligonucleotide probe hybridizes faster. A breast case with weak HER2 signal by INFORM HER2 DUAL ISH DNA Probe (FDA-approved protocol, 6 hr hybridization) was selected. Duplicate slides were stained with HER2 oligonucleotide probe and HER2 ds probe (6.0 ug/ml each) at shorter hybridization time (16, 32 and 60 min). For 16 min hybridization, HER2 oligonucleotide probe staining shows HER2 signals intensity 1.0 & 1.5 (FIGS. 3(A) and (C)) while HER2 ds probe staining intensities are 0.5 & 0.5 (FIGS. 3(B) and (D)). For 32 min hybridization, HER2 oligonucleotide probe staining shows HER2 signals intensity 1.5 & 1.5 while HER2 ds probe staining intensity is 1.0 & 1.5 (FIG. 3(A)). For 60 min hybridization, HER2 oligonucleotide probe staining shows HER2 signals intensity 2.0 & 2.0 while HER2 ds probe staining intensities are 2.0 & 1.5 (FIG. 3(A)).

Figure 3B:
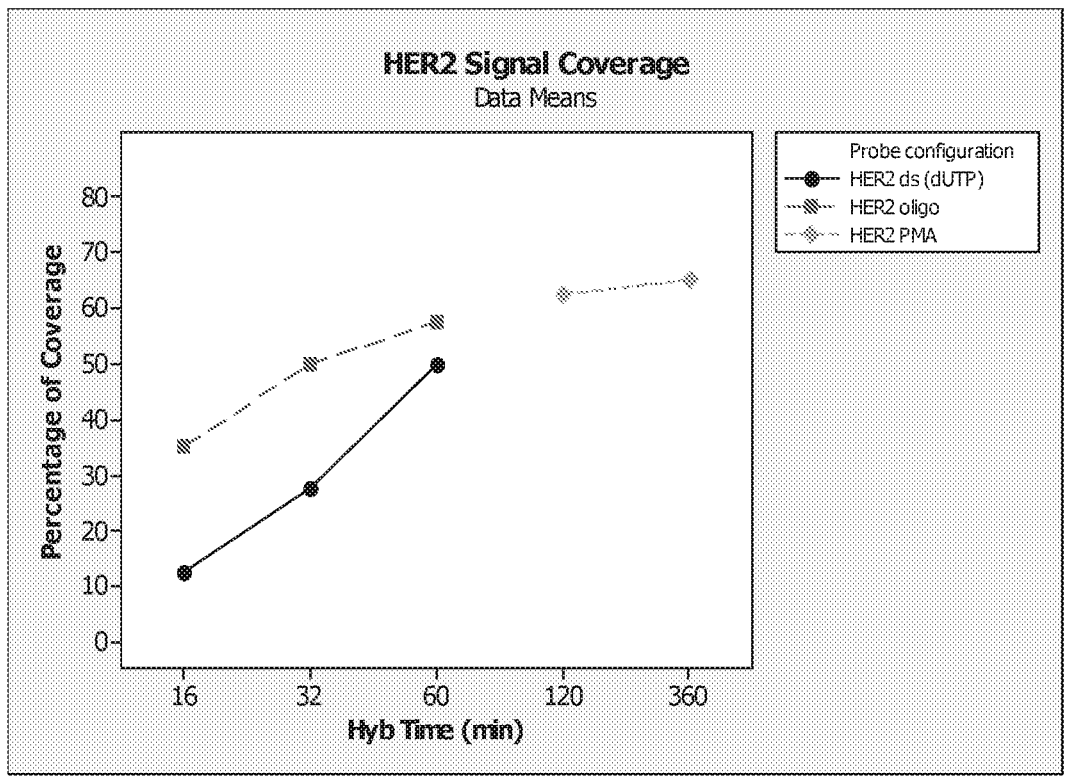
Figure 3C:
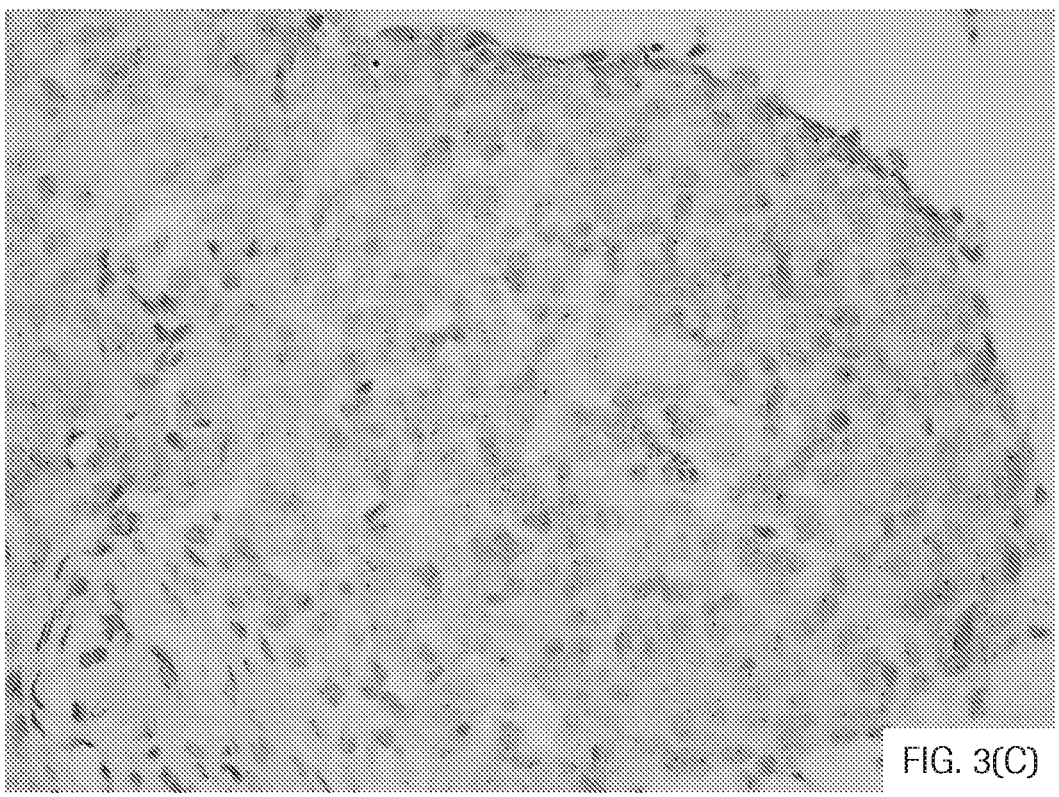
Figure 3D:
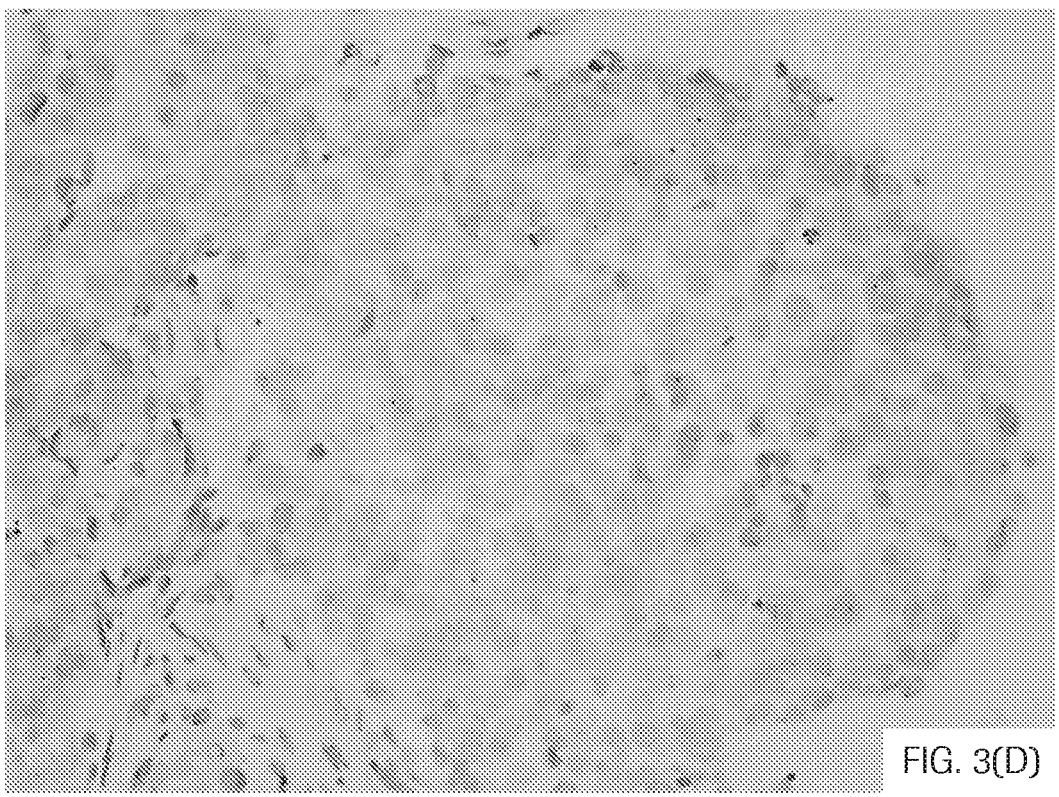

For 16 min hybridization, HER2 oligonucleotide probe staining shows HER2 signals coverage 40% & 30% (FIGS. 3(B) and (C)), while HER2 ds probe staining signal coverage is 5% & 20% (FIGS. 3(B) and (D)). For 32 min hybridization, HER2 oligonucleotide probe staining shows HER2 signal coverage 50% & 50%, while HER2 ds probe staining signal coverage is 30% & 25% (FIG. 3(B)). For 60 min hybridization, HER2 oligonucleotide probe staining shows HER2 signal coverage 55% & 60%, while HER2 ds probe staining signal coverage is 50% & 50% (FIG. 3(B)).

HER2 oligonucleotide probe did not show background signals on all the tested hybridization time points, while HER2 ds probe staining has mild background (0.75 and 0.25 at 32 min, and 0.25 and 0 at 60 min).

For 2 hr hybridization, INFORM HER2 DUAL ISH DNA Probe staining shows HER2 signals intensity 2 & 2.5 and coverage of 60% &65%. For 6 hr hybridization, INFORM HER2 DUAL ISH DNA Probe staining shows HER2 signals intensity 2 & 2.5 and coverage of 65% & 65%. No background was observed on these slides.

The above data suggest HER2 oligonucleotide hybridizes faster than HER2 ds probe. Higher signal intensity and better coverage was demonstrated at the earlier time points of hybridization process.

HER2 oligonucleotide probe staining exhibited favorable staining when comparing to HER2 ds probe at the same concentrations (3, 6, 9, and 12 µg/ml), hybridization times (1&2 hrs) and stringency wash temperatures (68, 70 and 72° C.). 6 µg/ml of HER2 oligonucleotide probe could achieve equivalent or better staining as 12 µg/ml of HER2 ds probe.

Figure 4A:
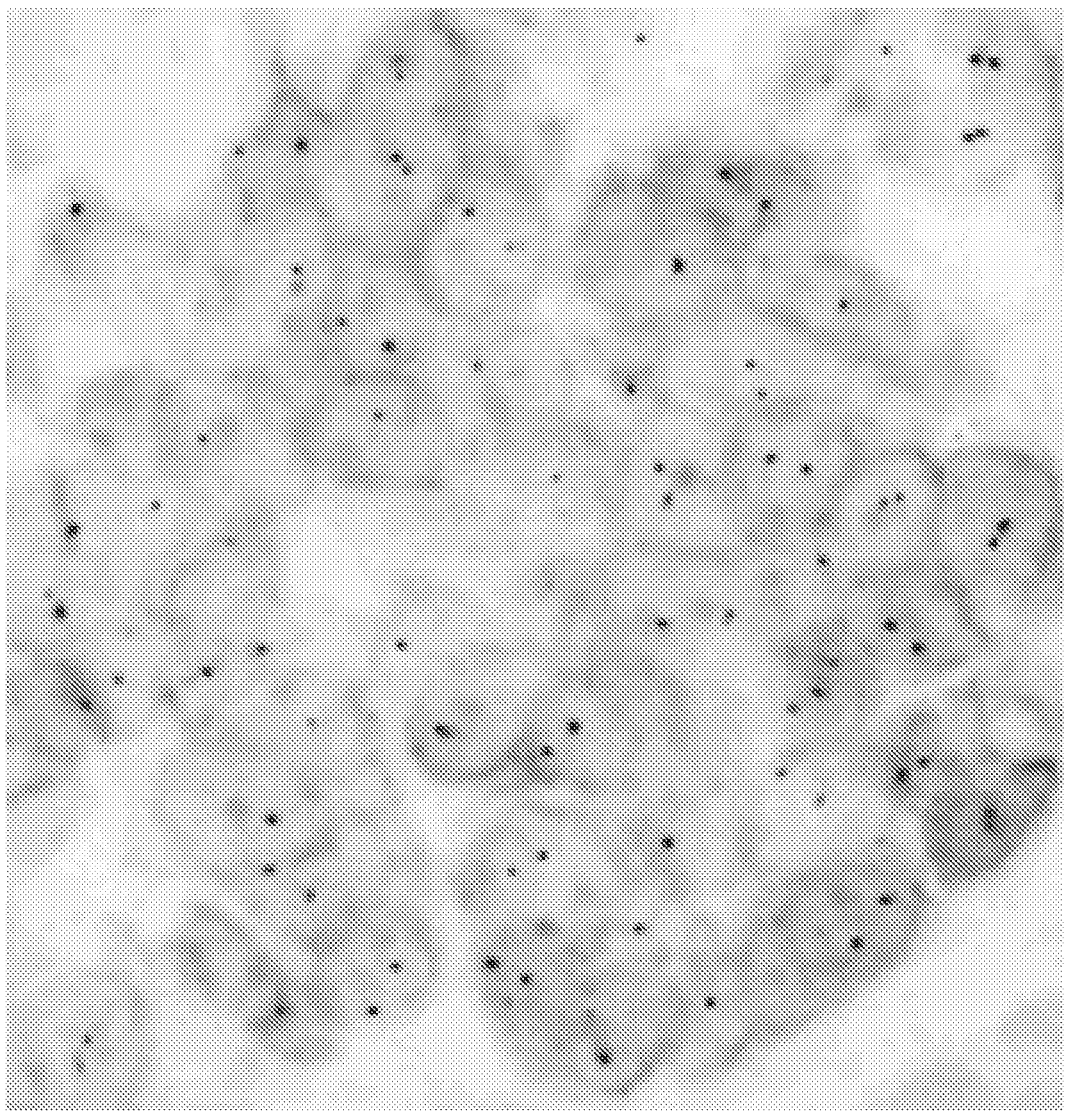
FIG. 4(A-B) are photomicrographs of stained breast tissue.
Figure 4B:
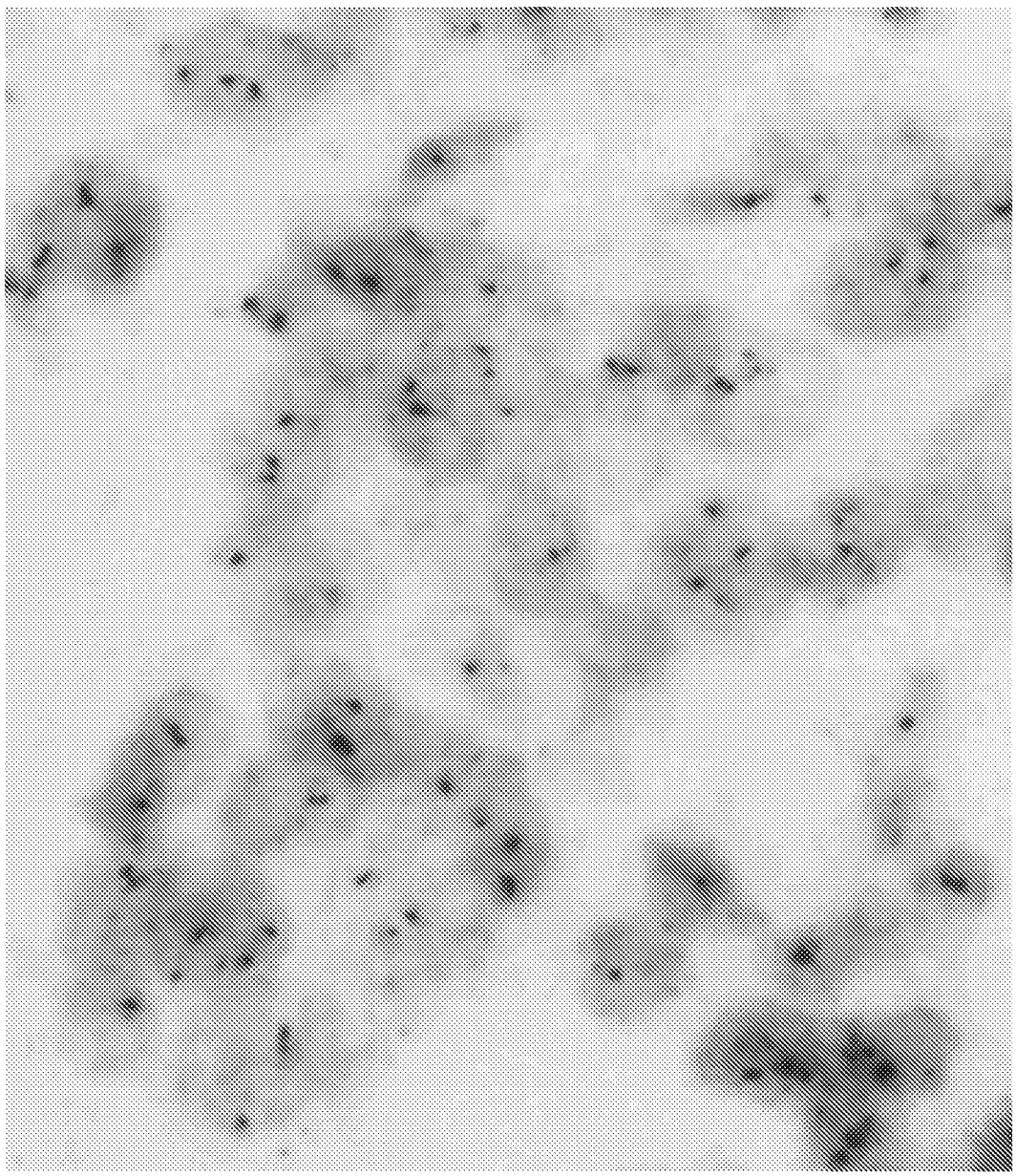

HER2 oligonucleotide probe staining (12.0 µg/ml) generates regular shape signals with uniformed sizes (FIG. 4(A)), while HER2 ds probe staining (12.0 µg/ml) has irregular signal shape with different sizes (FIG. 4(B)). HER2 oligonucleotide probe generates minimal background signal (FIG. 4(A)), while HER2 ds probe staining has some nuclear dusting background (FIG. 4(B)). Since HER2 oligonucleotide probe staining demonstrated minimal background signal when used at normal concentration ranges, we challenged it with extremely high concentration (24 µg/ml). HER2 oligonucleotide probe staining revealed brownish background that surrounds nuclear boundary, however, this background pattern does not interfere with signal enumeration. HER2 ds probe staining at 24 µg/ml exhibited nuclear dusting that may confuse weak specific signals from non-specific background signals.

HER2 oligonucleotide probe with 1 hr hybridization staining is robust enough to reach the performance level of INFORM HER2 DUAL ISH DNA Probe with 6 hr hybridization. In particular, 109 breast tissues were selected for HER2 oligonucleotide probe performance evaluation. These samples were first stained with INFORM HER2 DUAL ISH DNA Probe (FDA-approved protocol, 6 hr hybridization), and demonstrated adequate or "boarder-line" staining intensity (2 is cut-off for acceptable, 1.5 is boarder-line). This pre-screening helped eliminate poor-quality tissues due to pre-analytical conditions. 79 tissues (72.5%) were considered passed by INFORM HER2 DUAL ISH DNA Probe. See TABLE 4.

TABLE 4

| 109 breast cases with minimally adequate tissue quality | HER2 PMA 6 hr hyb | HER2 ds 1 hr hyb | HER2 oligo 1 hr hyb |
|---|---|---|---|
| # of passed tissue (%) | 79 (72.5%) | 32 (29.3%) | 94 (86.2%) |

Figure 5A:
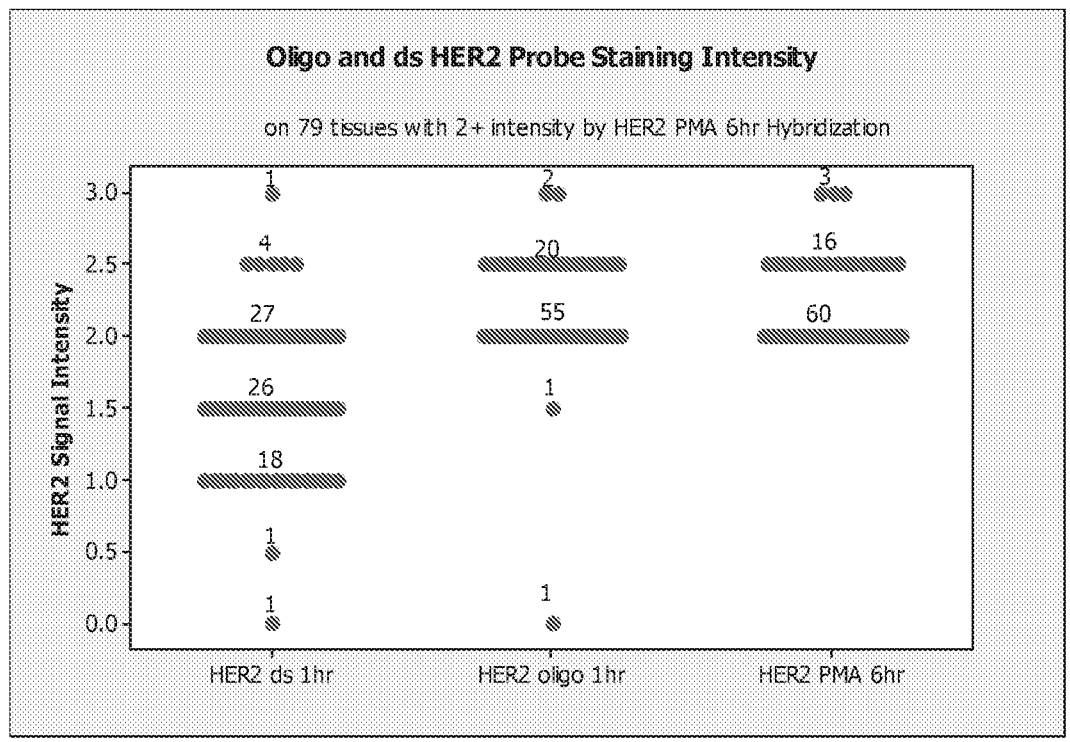
FIG. 5(A-B) are graphs showing HER2 staining for different hybridization conditions.
Figure 5B:
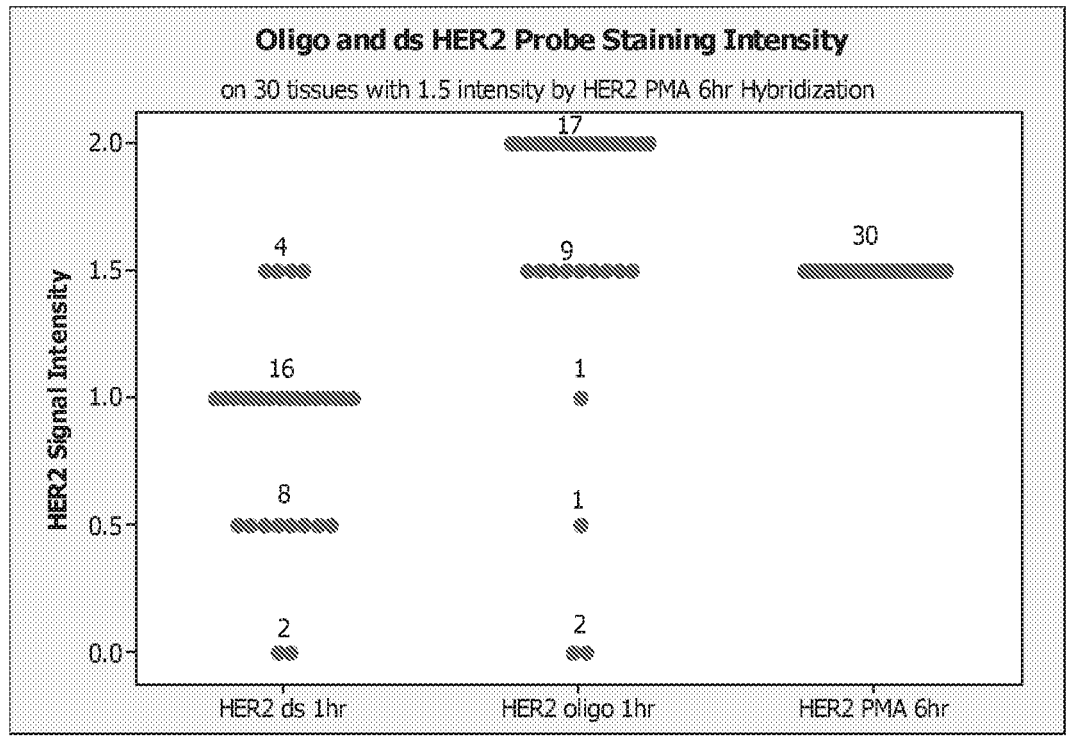

HER2 oligonucleotide probe (12 µg/ml) 1 hr hybridization staining had 94 (86.2%) tissues passed, while HER2 ds probe 1 hr hybridization had 32 (29.3%) tissues passed (TABLE 4). The data suggest HER2 oligonucleotide probe staining is robust enough to reach the level of performance of INFORM HER2 DUAL ISH DNA Probe with 6 hr hybridization. Among the 79 tissues with intensity by INFORM HER2 DUAL ISH DNA Probe (FIG. 5(A)), HER2 oligonucleotide probe achieved comparable performance (77 passed). Among the 30 tissues with 1.5 intensity by INFORM HER2 DUAL ISH DNA Probe (FIG. 5(B)), 17 tissues' staining was improved to intensity 2 (therefore passed).

H. Chromosome 77 Oligonucleotide Probe Performance Evaluation:

Selection of Chromosome 17-Specific Oligonucleotides

Figure 6A:
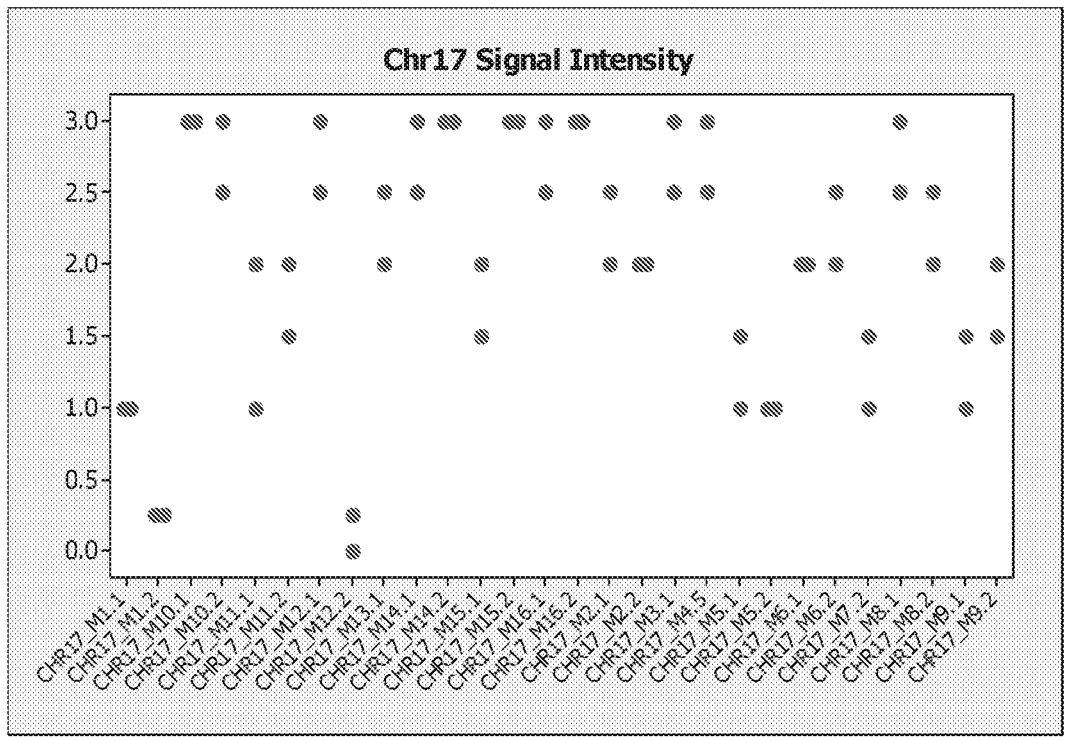
FIG. 6(A-D) are graphs and photomicrographs showing Chr17 signal intensity and background for particularly tested oligonucleotides.
Figure 6B:
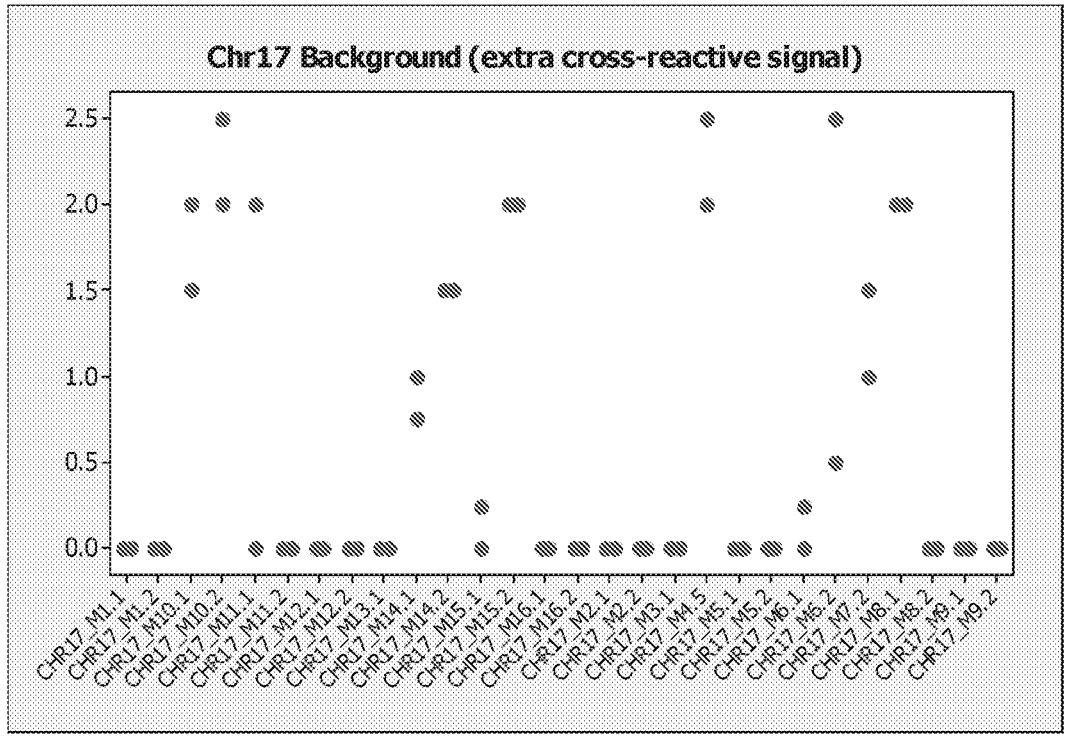
Figure 6C:
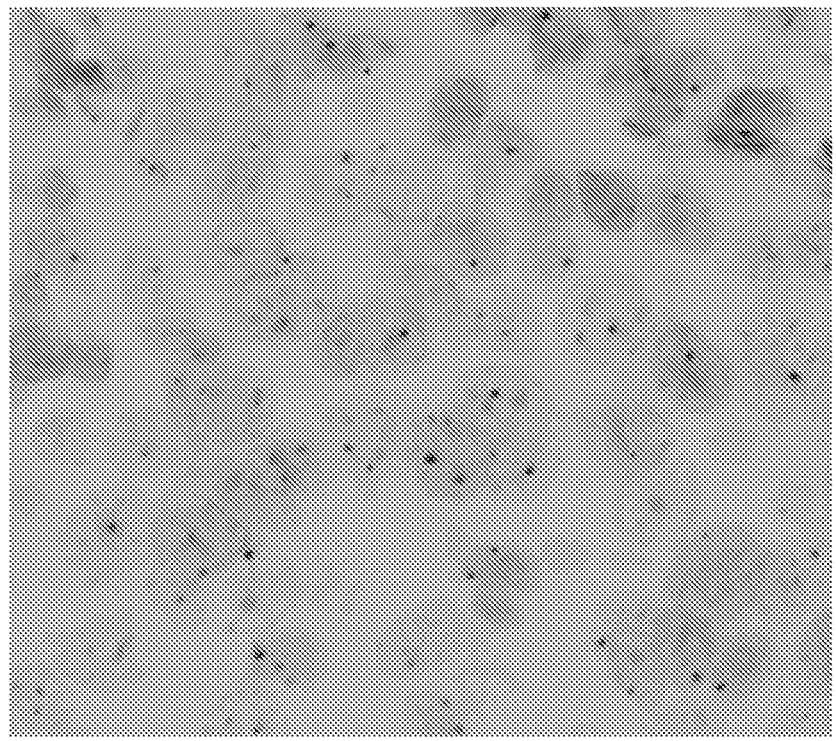
Figure 6D:
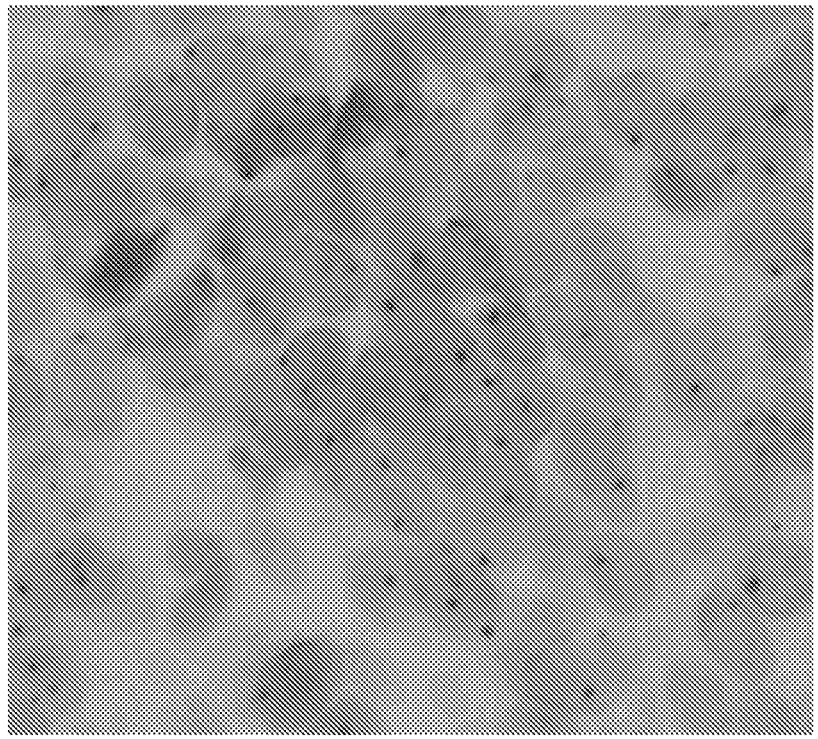

Each of the 28 chromosome 17 oligonucleotides (1.0 µg/ml) was stained on 2 breast tissues at stringency wash temperature 70 and/or 72° C. Fourteen oligonucleotides were excluded due to the extra cross-reactive signals, i.e. M4.5 (2.0&2.5), M6.1 (0&0.25), M6.2 (0.5&2.5), M7.2 (1.0&1.5), M8.1 (2.0&2.0), M10.1 (1.5&2), M10.2 (2&2.5), M11.1 (0&2), M14.1 (0.75&1.0), M14.2 (1.5&1.5), M15.1 (0&0.25), and M15.2 (2.0&2.0) (FIG. 6(B)). FIG. 6(D) is an example of M11.2 stained slide, one to two specific chr17 signals with adequate intensity are present in each cell. FIG. 6(C) shows an example of M7.2 stained slide, extra faint cross-reactive signals were present in addition to the major chr17 specific signals in the cells. Two oligonucleotides were excluded for the extremely weak signals, i.e. M1.2 (0.25&0.25) and M2.2 (0&0.25) (FIG. 6(A)). A total of 14 oligonucleotides (M1.1, M2.1, M2.2, M3.1, M5.1, M5.2, M8.2, M9.1, M9.2, M11.2, M12.1, M13.1, M16.1, and M16.2) were chosen enter the pool of Chr17 oligonucleotide probe as listed herein.

Figure 7A:
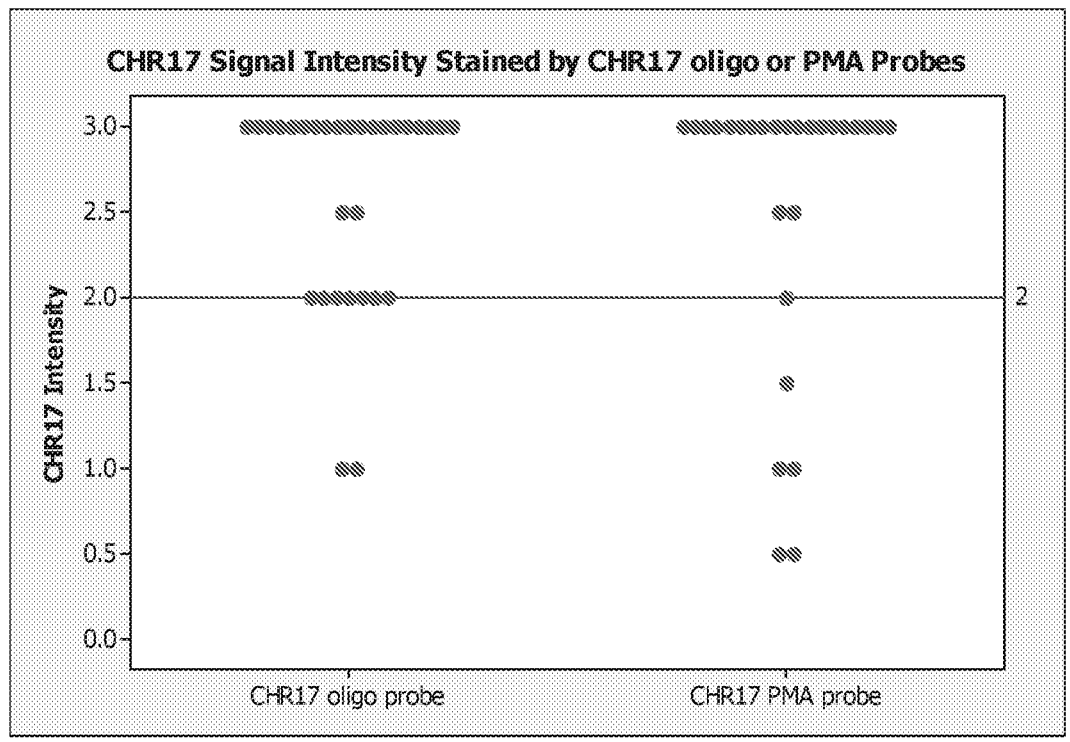
FIG. 7(A-D) are graphs showing Chr17 signal intensity, staining coverage, background, and pass/fail for a single strand probe versus a double strand commercial probe product.
Figure 7B:
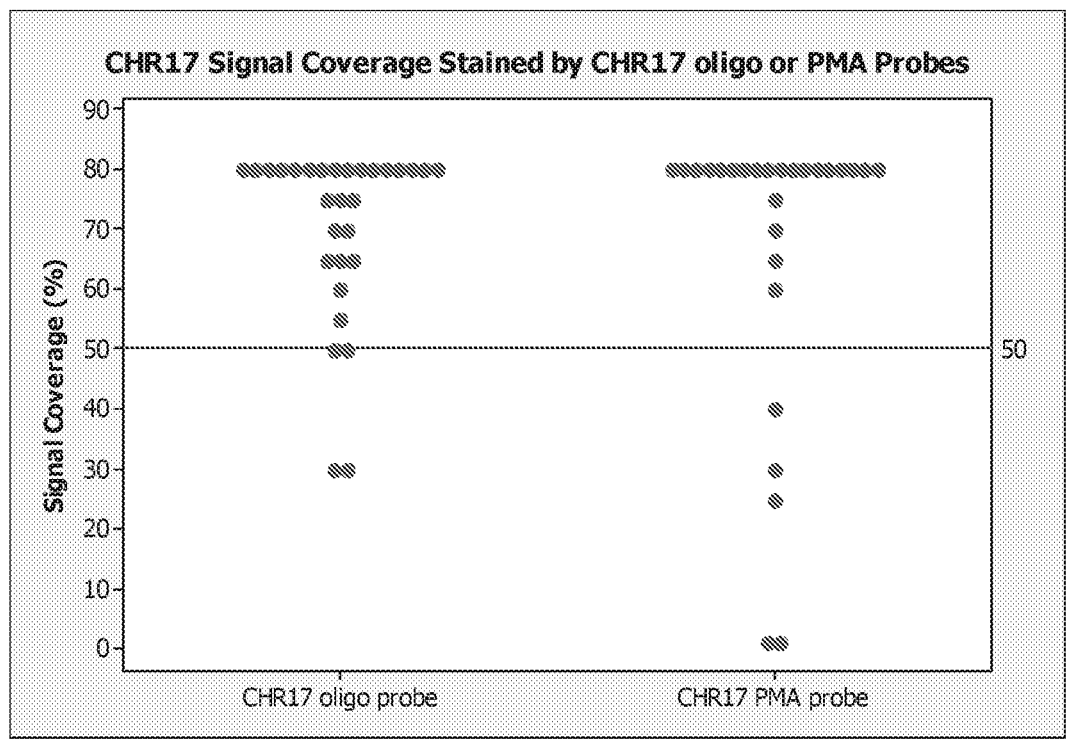
Figure 7C:
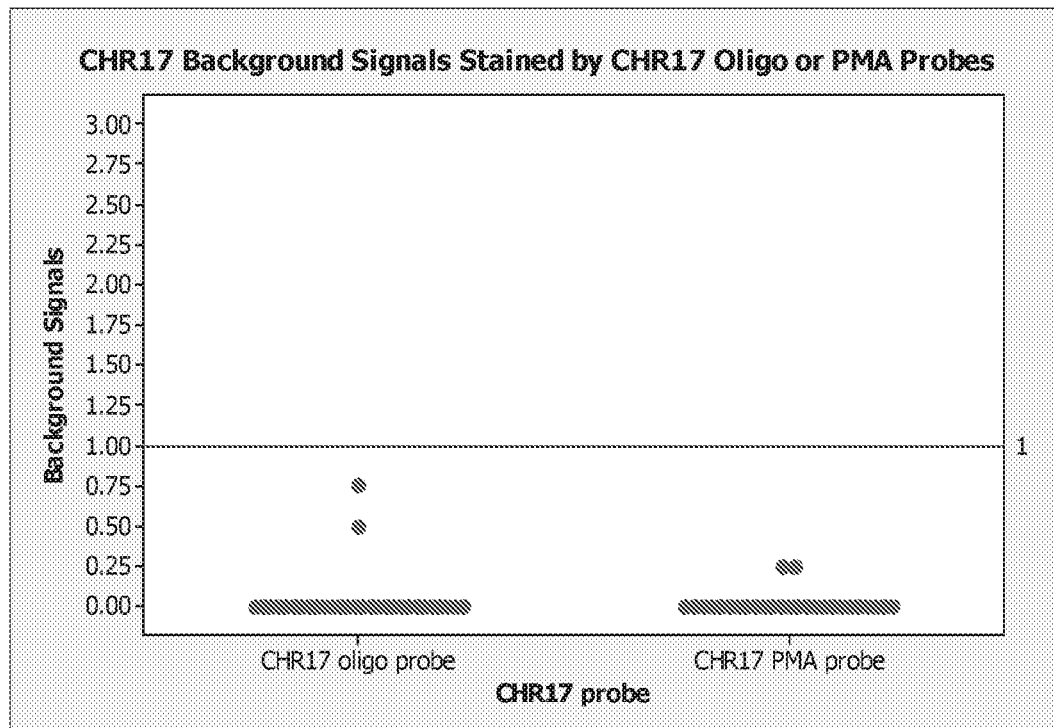
Figure 7D:
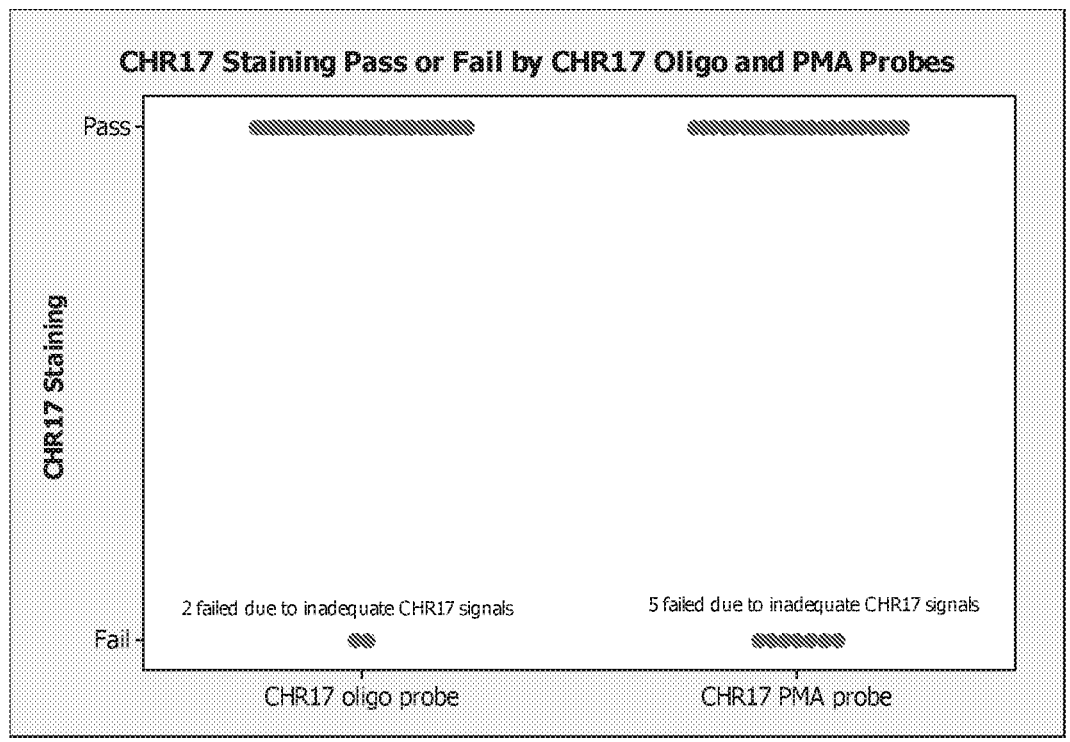

Fifteen (15) breast tissues were selected for Chr17 oligonucleotide probe performance evaluation. The chromosome 17 staining was performed earlier with INFORM HER2 DUAL ISH DNA Probe (FDA-approved protocol, 6 hr hybridization). Chromosome 17 signals in these samples (duplicate slides each) range from strong to weak intensities (0-3 scale). Chr17 oligonucleotide probe (0.5 µg/ml) 1 hr hybridization staining has comparable staining intensity (2.60±0.61 vs 2.54±0.84, p>0.05, FIG. 7(A)), coverage (70.50±14.46 vs 66.93±24.61, p>0.05, FIG. 5B) and background (0.04±0.16 vs 0.02±0.07, p>0.05, FIG. 7(C)) to those by Chr17 PMA probe. All non-acceptable chr17 staining are due to inadequate chr17 signal intensity, among which 2 failed by Chr17 oligonucleotide probe and 5 by Chr17 PMA probe (FIG. 7(D)). The data suggest Chr17 oligonucleotide probe 1 hr hybridization staining is robust enough to reach the level of performance of INFORM HER2 DUAL ISH DNA Probe with 6 hr hybridization.

Analytical Characterization of HER2/CHR17 Oligonucleotide Probe DISH Assay

Figure 8:
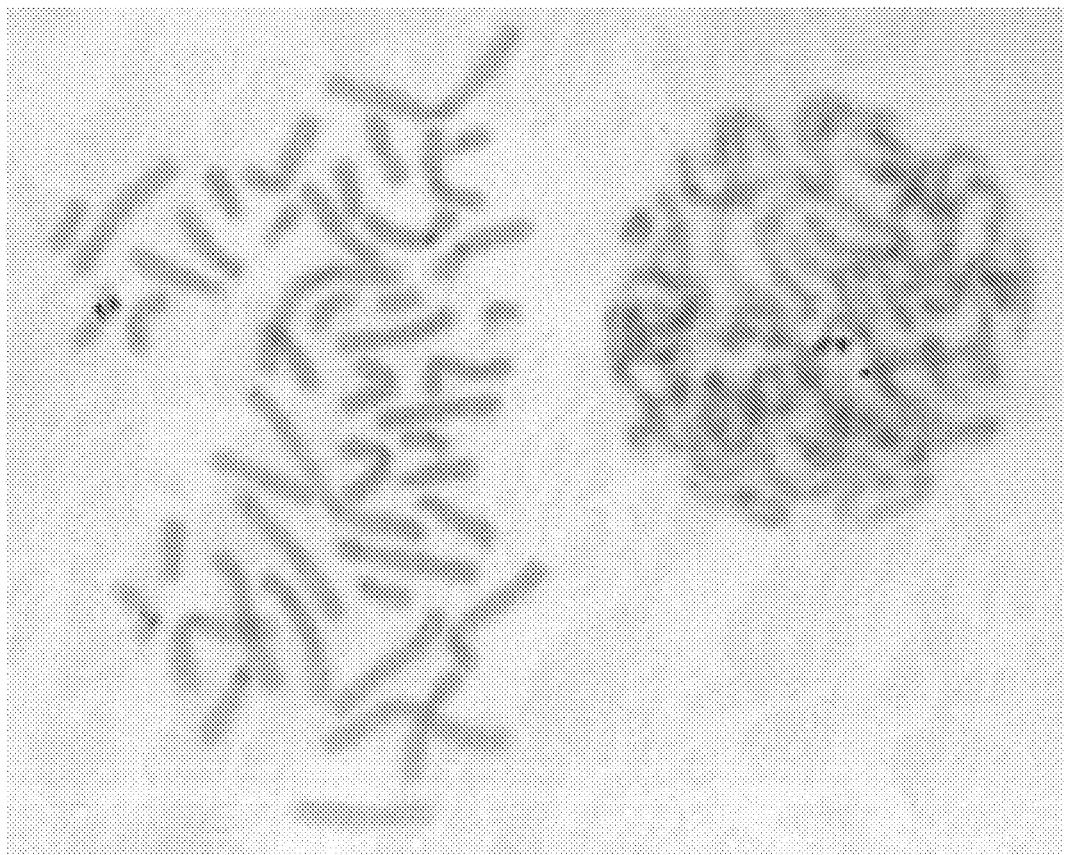
FIG. 8 is a photomicrograph of staining of a chromosomal metaphase spread showing specificity.

Analytical specificity of HER2/CHR17 Oligonucleotide Probe DISH on chromosomal metaphase spreads was tested. HER2 oligonucleotide probe (black signal) and CHR17 oligonucleotide probe (red signal) were localized to the same chromosome. No cross-hybridization of either HER2 probe or CHR17 probe to other chromosomes was observed (FIG. 8).

Figure 9:
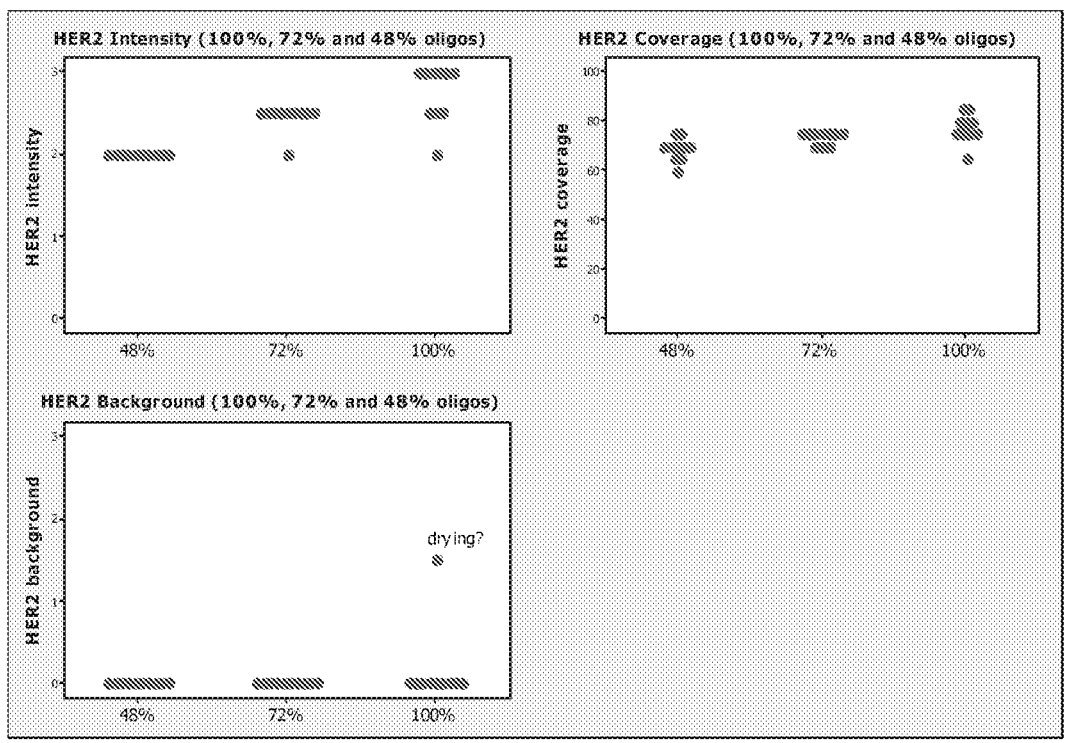
FIG. 9 is a series of graphs showing the effect of using 48%, 72%, and 100% of the 1196 HER2 oligonucleotide probes on intensity, coverage, and background.

Functional test on the minimally required number of HER2 oligonucleotides was tested. Forty-eight (48), 72 and 100% of the total number (1196) HER2 oligonucleotides were functionally tested on 30 slides from 5 breast cases. All slides passed for HER2 staining (with the criteria Intensity 2). 48% of 1196 HER2 oligonucleotides had HER2 intensity 2.00±0, 72% had HER2 intensity 2.45±0.16, and 100% had HER2 intensity 2.75±0.35. 100% (1196 oligonucleotides) had the most robust HER2 staining comparing to those by 48% and 72% (p<0.05). 48% of 1196 HER2 oligonucleotides had HER2 coverage 69.00±4.60, 72% had HER2 coverage 73.50±2.42, and 100% had HER2 coverage 77.50±5.89. 100% (1196 oligonucleotides) had significantly higher HER2 staining coverage than that by 48% (p<0.05) (FIG. 9).

Figure 10:
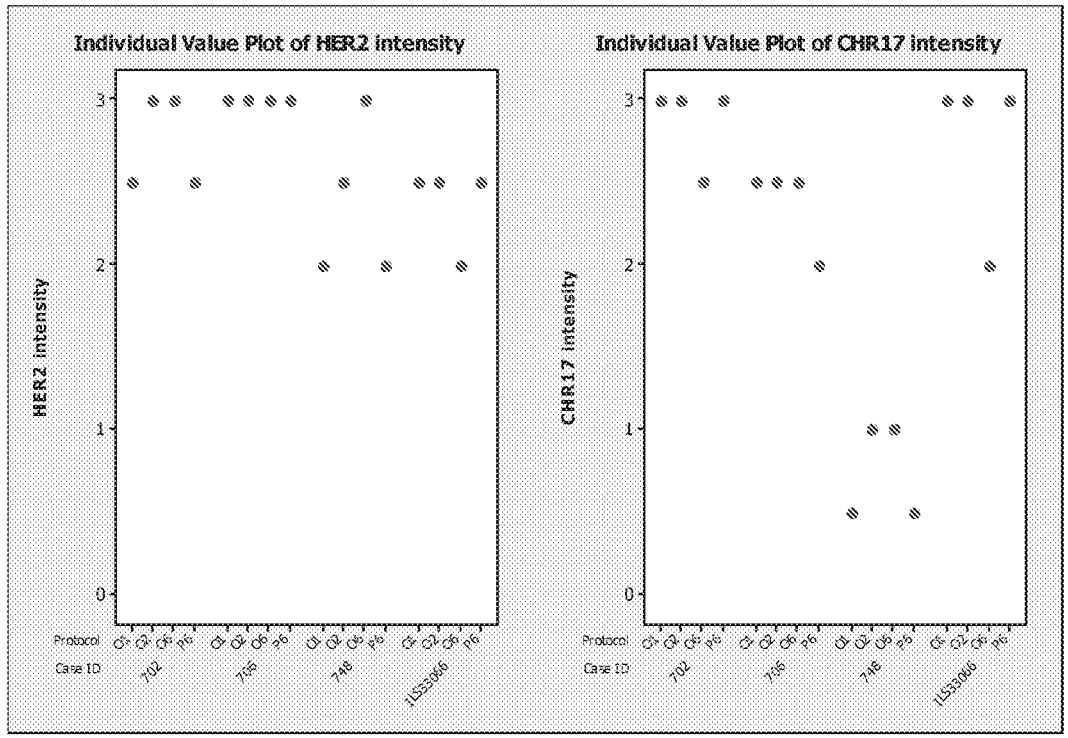
FIG. 10 is a series of graphs showing no consistent linkage between longer hybridization times (e.g. 2 and 6 hr) and improved staining intensity.

Functional test of the time course (1, 2 and 6 hr) of the full-set (1196) Her2 oligonucleotides was tested. The full-set (1196) Her2 oligonucleotides were tested for 1, 2 and 6 hr hybridization on 16 slides from 4 breast cases. HER2 oligonucleotides with 1 hr hybridization staining achieved comparable staining performance to INFORM HER2 DUAL ISH DNA Probe with 6 hr hybridization. We did not find consistent linkage between the longer hybridization times (e.g. 2 and 6 hr) and improved staining intensity (FIG. 10).

An equivalency study of HER2/CHR17 Oligonucleotide Probe DISH with 1 hr hybridization on individual breast tissues was performed to compare staining adequacy compared to INFORM HER2 DUAL ISH DNA Probe with 6 hr hybridization. Eighty-nine (89) breast tissues were selected for HER2/CHR17 Oligonucleotide Probe DISH performance evaluation. Similar to above, these samples demonstrated adequate or "boarder-line" staining intensity, i.e. HER2 signal intensity 1.5, CHR17 signal intensity on at least one slide stained by INFORM HER2 DUAL ISH DNA Probe with 6 hr hybridization. This pre-screening helped eliminate poor-quality tissues due to pre-analytical conditions. 128 slides (128/146, 85.5%) were considered "pass" for HER2 staining by INFORM HER2 DUAL ISH DNA Probe with 1 hr hybridization, while 156 slides (156/174, 87.67%) were considered pass for HER2 staining by HER2/CHR17 Oligonucleotide Probe DISH with 1 hr hybridization (p=0.578). 103 slides (103/149, 69.13%) were considered pass for CHR17 staining by INFORM HER2 DUAL ISH DNA Probe with 6 hr hybridization, while 129 slides (129/175, 73.71%) were considered pass for CHR17 staining by HER2/CHR17 Oligonucleotide Probe DISH with 1 hr hybridization (p=0.363). No significant difference was found for HER2 and CHR17 staining between the two assays. While no severe speckling or slide drying artifact was found for HER2/CHR17 Oligonucleotide Probe DISH with 1 hr hybridization, 6 slides stained by INFORM HER2 DUAL ISH DNA Probe with 6 hr hybridization failed for evaluation due to severe speckling background, and 5 slides stained by INFORM HER2 DUAL ISH DNA Probe with 6 hr hybridization failed for slide drying (11/175, 6.3%). See TABLE 5.

TABLE 5

| | HER2 signal | | | |
|---|---|---|---|---|
| | 1st-Pass | Fail | Pass rate | Significance |
| HER2/Chr17 oligonucleotide probe DISH | 156 | 18 | 87.67% | p = 0.578 |
| INFORM HER2 DUAL ISH DNA Probe | 128 | 18 | 85.50% | |

| | CHR17 signa | | | |
|---|---|---|---|---|
| | 1st-Pass | Fail | Pass rate | Significance |
| HER2/Chr17 oligonucleotide probe DISH | 129 | 46 | 73.71% | p = 0.363 |
| INFORM HER2 DUAL ISH DNA Probe | 103 | 46 | 69.13% | |

| Artifacts | INFORM HER2 DUAL ISH DNA Probe | HER2/Chr17 oligonucleotide probe DISH |
|---|---|---|
| Speckling (Background 2, failure) | 6 | 0 |
| Slide (failure) | 5 | 0 |

Figure 11A:
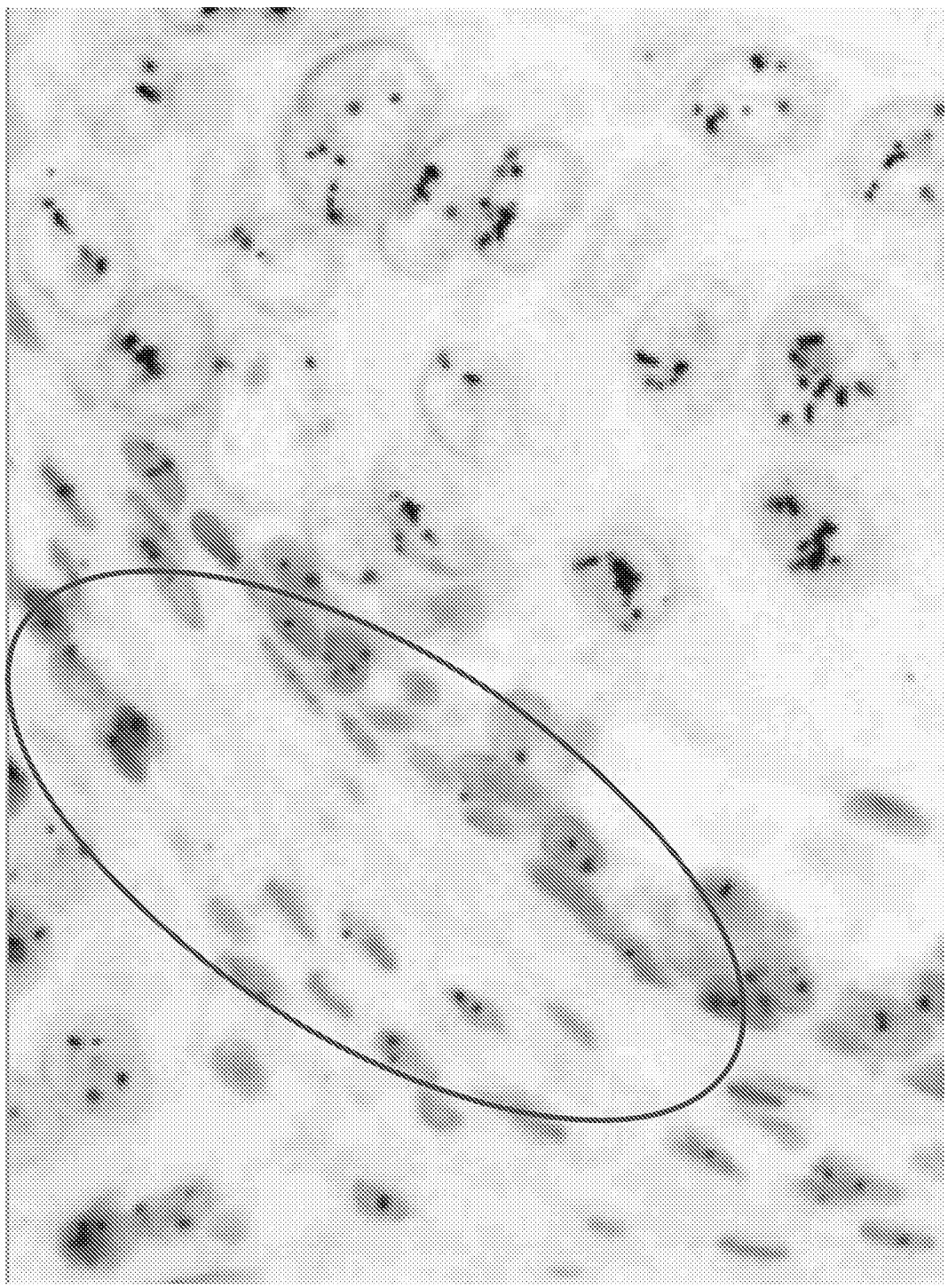
FIG. 11(A-B) are photomicrographs of a breast tissue stained with a DISH assay.

FIG. 11(A) is an example of staining on Case #709. HER2/CHR17 Oligonucleotide Probe ISH 1 hr hybridization staining had HER2 intensity 2.5, coverage 70%, background 0; Chr17 intensity 2.5, coverage 70%, and background 0; while INFORM HER2 DUAL ISH DNA Probe with 6 hr hybridization staining had HER2 intensity 1, coverage 40%, background 0; Chr17: Intensity 1, coverage 35%, background 0. In the circled stromal areas, INFORM HER2 DUAL ISH DNA Probe with 6 hr hybridization had lack of staining; hence the HER2 and CHR17 staining intensity were assigned to 1. The data suggest HER2/CHR17 Oligonucleotide Probe DISH with 1 hr hybridization staining performance is comparable to that of INFORM HER2 DUAL ISH DNA Probe with 6 hr hybridization. HER2/CHR17 Oligonucleotide Probe DISH with 1 hr hybridization staining has lower incidence of staining failure (i.e. severe speckling and slide drying) than that by INFORM HER2 DUAL ISH DNA Probe with 6 hr hybridization.

Concordance of HER2 gene status between HER2/CHR17 Oligonucleotide Probe DISH with 1 hr hybridization and INFORM HER2 DUAL ISH DNA Probe with 6 hr hybridization staining Sixty-three (63) cases with paired slides of intensity for both HER2 and CHR17 by HER2/CHR17 Oligonucleotide Probe DISH with 1 hr hybridization and INFORM HER2 DUAL ISH DNA Probe with 6 hr hybridization were selected for signal enumeration. Fifty (50) cases were diagnosed as HER2 non-amplified by both HER2/CHR17 Oligonucleotide Probe DISH with 1 hr hybridization and INFORM HER2 DUAL ISH DNA Probe with 6 hr hybridization staining. Twelve (12) cases were diagnosed as HER2 amplified by both HER2/CHR17 Oligonucleotide Probe DISH with 1 hr hybridization and INFORM HER2 DUAL ISH DNA Probe with 6 hr hybridization staining. One case (ILS32554) was diagnosed as HER2 amplified by HER2/CHR17 Oligonucleotide Probe DISH with 1 hr hybridization staining (HER2/Chr17 ratio: 2.08), while INFORM HER2 DUAL ISH DNA Probe with 6 hr hybridization staining is non-amplified (HER2/Chr17 ratio: 1.92). The Percent Positive Agreement (PPA) is 100% (95% score CI: 77.1-100%), and the Percent Negative Agreement (PNA) is 98.04% (95% score CI: 92.7-98.0%). The percentage of Coefficient of Variation (% CV) of non-clustered signal counts (for HER2 and CHR17) from the paired slides is 5.66±4.84 (<20% as acceptable). See TABLE 6.

TABLE 6

| HER2/CHR17 oligonucleotide probe DISH | INFORM HER2 DUAL ISH DNA Probe | | |
|---|---|---|---|
| | Amplified | Non-Amplified | Total |
| Amplified | 12 | 1* | 12 |
| Non-Amplified | 0 | 50 | 51 |
| Total | 12 | 51 | 63 |

| | n/N | % (95% Score CI) |
|---|---|---|
| Percent Positive Agreement (PPA) | 12/12 | 100 (77.1-100) |
| Percent Negative Agreement (PNA) | 50/51 | 98.04 (92.7-98.0) |

*ILS32554: PMA 1.92, Oligonucleotide 2.08

Figure 11B:
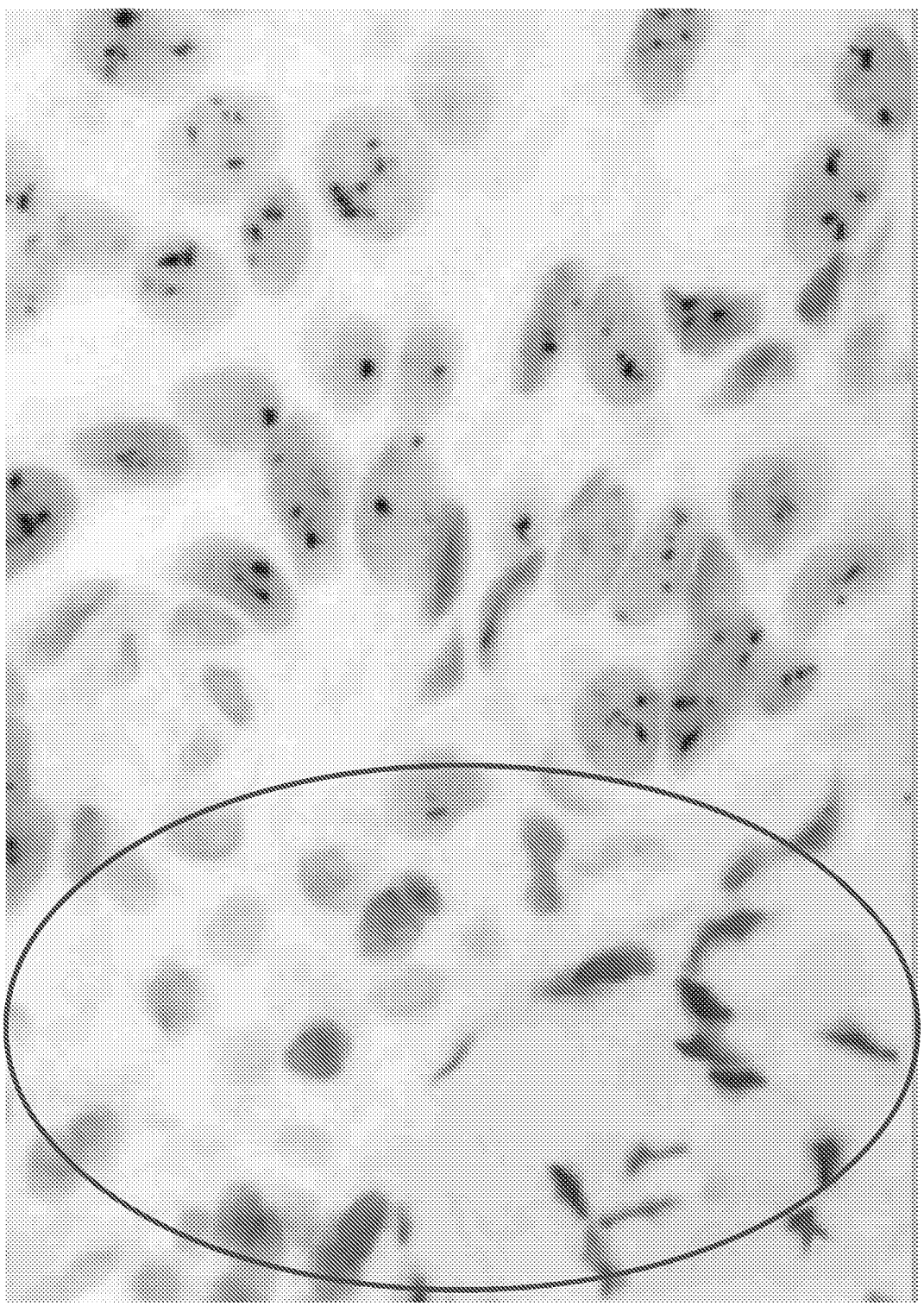

FIG. 11(B) is an example of staining on Case #731. HER2/CHR17 Oligonucleotide Probe DISH with 1 hr hybridization staining had HER2 intensity 3, coverage 80%, background 0; Chr17: Intensity 2.5, coverage 75%, background 0; HER2 counts: 46, Chr17 counts: 34, ratio: 1.35; while INFORM HER2 DUAL ISH DNA Probe with 6 hr hybridization staining had HER2 intensity 3, coverage 80%, background 0.5; CHR17 intensity 3, coverage 80%, background 0. Both stains generated similar HER2 and CHR17 signal counts, and hence similar HER2/CHR17 ratio. Silver dusting background was observed on INFORM HER2 DUAL ISH DNA Probe with 6 hr hybridization stains. The data suggest HER2/CHR17 Oligonucleotide Probe DISH with 1 hr hybridization staining and INFORM HER2 DUAL ISH DNA Probe with 6 hr hybridization staining have a high concordance on the diagnoses of HER2 gene status.

An evaluation of the two assays' robustness on a cohort of tissue microarray (TMA) that was not prescreened by INFORM HER2 DUAL ISH DNA Probe with 6 hr hybridization was completed. Ninety-five (95) breast tissue cores in a TMA slide were stained with HER2/CHR17 Oligonucleotide Probe DISH with 1 hr hybridization and INFORM HER2 DUAL ISH DNA Probe with 6 hr hybridization for the evaluation of assay robustness on these tissues without the information of pre-analytical conditions and tissue quality. This study was designed to assess the assay robustness as archived TMA tissues are generally considered difficult specimens for ISH assay. HER2/CHR17 Oligonucleotide Probe DISH with 1 hr hybridization had 73 cores (76.8%) stained HER2 intensity 2 and above, while INFORM HER2 DUAL ISH DNA Probe with 6 hr hybridization had 57 cores (60.0%) stained HER2 intensity 2 and above. The difference between the two assays on HER2 intensity reaches close to 90% CI significance (p=0.011). HER2/CHR17 Oligonucleotide Probe DISH with 1 hr hybridization had 53 cores (55.8%) stained CHR17 intensity 2 and above, while INFORM HER2 DUAL ISH DNA Probe with 6 hr hybridization: had 35 cores (36.80%) stained CHR17 intensity 2 and above. The difference between the two assays on CHR17 intensity reaches close to 90% CI significance (p=0.012). HER2/CHR17 Oligonucleotide Probe DISH with 1 hr hybridization stained slides had 1.89±0.76 on HER2 intensity, while INFORM HER2 DUAL ISH DNA Probe with 6 hr hybridization stained slides 1.58±0.76 on HER2 intensity (p=0.005). HER2/CHR17 Oligonucleotide Probe DISH with 1 hr hybridization stained slides had 1.49±0.83 on CHR17 intensity, while INFORM HER2 DUAL ISH DNA Probe with 6 hr hybridization stained slides 1.04±0.87 on CHR17 intensity (p=0.000). The background for both HER2/CHR17 Oligonucleotide Probe DISH with 1 hr hybridization (0.11±0.18) and INFORM HER2 DUAL ISH DNA Probe with 6 hr hybridization (0.04±0.11) are very low from the acceptable level (<2). See TABLE 7.

TABLE 7

The number of slides at given signal intensity level

| Intensity level | INFORM HER2 DUAL ISH DNA Probe (6 hr hyb) HER2 signal | HER2/CHR17 oligonucleotide probe DISH (1 hr hyb) HER2 signal | Significance | INFORM HER2 DUALISH DNA Probe (6 hr hyb) CHR17 signal | HER2/CHR17 oligonucleotide probe DISH (1 hr hyb) CHR17 signal | Significance |
|---|---|---|---|---|---|---|
| 3 | 0 | 5 | | 0 | 0 | |
| 2.5 | 10 | 28 | | 4 | 16 | |
| 2 | 47 | 40 | | 29 | 36 | |
| 1.5 | 16 | 2 | | 11 | 9 | |
| 1 | 3 | 10 | | 4 | 7 | |
| 0.5 | 8 | 4 | | 21 | 18 | |
| 0 | 11 | 6 | | 26 | 9 | |
| Total tissue cores | 95 | 95 | | 95 | 95 | |
| Percentage passed tissue cores | 60.0% (57/95) | 76.8% (73/95) | p = 0.011 | 35/95 (36.8%) | 53/95 (55.8%) | p = 0.012 |

HER2 and CHR17 staining scores

| | INFORM HER2 DUAL ISH DNA Probe (6 hr hyb) | HER2/CHR17 oligonucleotide probe DISH (1 hr hyb) | Significance |
|---|---|---|---|
| HER2 Intensity | 1.58 ± 0.76 | 1.89 ± 0.76 | p = 0.005 |
| HER2 Background | 0.04 ± 0.11 | 0.11 ± 0.18 | p = 0.001 |
| CHR17 Intensity | 1.04 ± 0.87 | 1.49 ± 0.83 | p = 0.000 |
| CHR17 Background | 0 | 0 | na |

The data suggest HER2/CHR17 Oligonucleotide Probe DISH with 1 hr hybridization has more robust staining on difficult tissues than INFORM HER2 DUAL ISH DNA Probe with 6 hr hybridization.

Figure 12A:
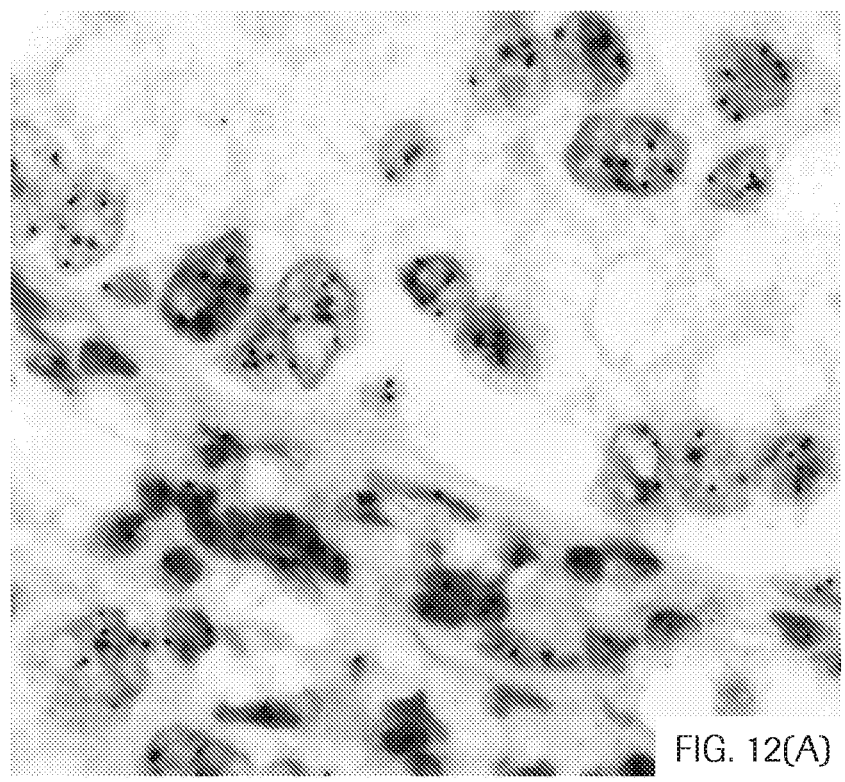
FIG. 12(A-B) are photomicrographs of a lung tissue stained with a DISH assay.
Figure 12B:
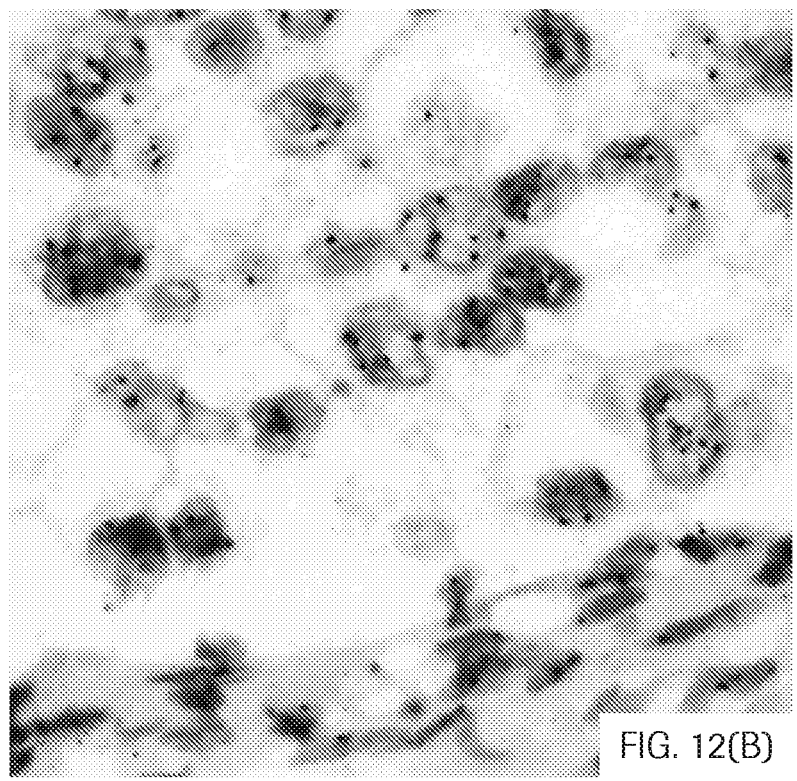
Figure 13A:
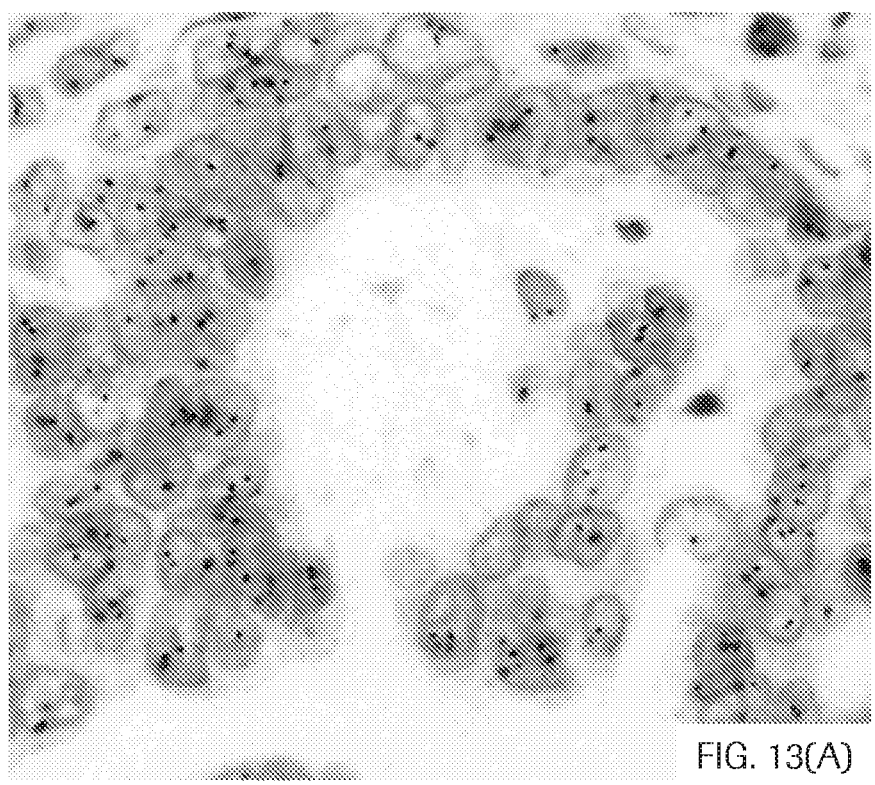
FIG. 13(A-B) are photomicrographs of a gastric tissue stained with a DISH assay.

In addition to testing on breast tissues, the feasibility of HER2/CHR17 Oligonucleotide Probe DISH with 1 hr hybridization was also demonstrated on lung (FIG. 12(A) showing the single strand probe and 12(B) showing the double strand probe) and gastric tissues (FIG. 13(A) showing the single strand probe and 13(B) showing the double strand probe). We further tested HER2/CHR17 Oligonucleotide Probe DISH with 1 hr hybridization on duplicate slides of 10 lung tissues and 10 gastric tissues. HER2/CHR17 Oligonucleotide Probe DISH with 1 hr hybridization has 65% pass for HER2 and 50% pass for CHR17 (based on criteria intensity 2), similar to 55% pass for HER2 and 50% pass for CHR17 by INFORM HER2 DUAL ISH DNA Probe with 6 hr hybridization (p=0.516 for HER2 and p=1.000 for CHR17). FIG. 12(A)-(B) is an example of staining on Case #F101411A1. HER2/CHR17 Oligonucleotide Probe DISH with 1 hr hybridization staining had HER2 intensity 3, coverage 80%, background 0; Chr17: Intensity 3.0, coverage 80%, background 0; while INFORM HER2 DUAL ISH DNA Probe with 6 hr hybridization staining had HER2 intensity 3, coverage 80%, background 0.5; CHR17 intensity 3, coverage 80%, background 0. Some silver background was observed on the tissue stained by INFORM HER2 DUAL ISH DNA Probe with 6 hr hybridization.

Figure 13B:
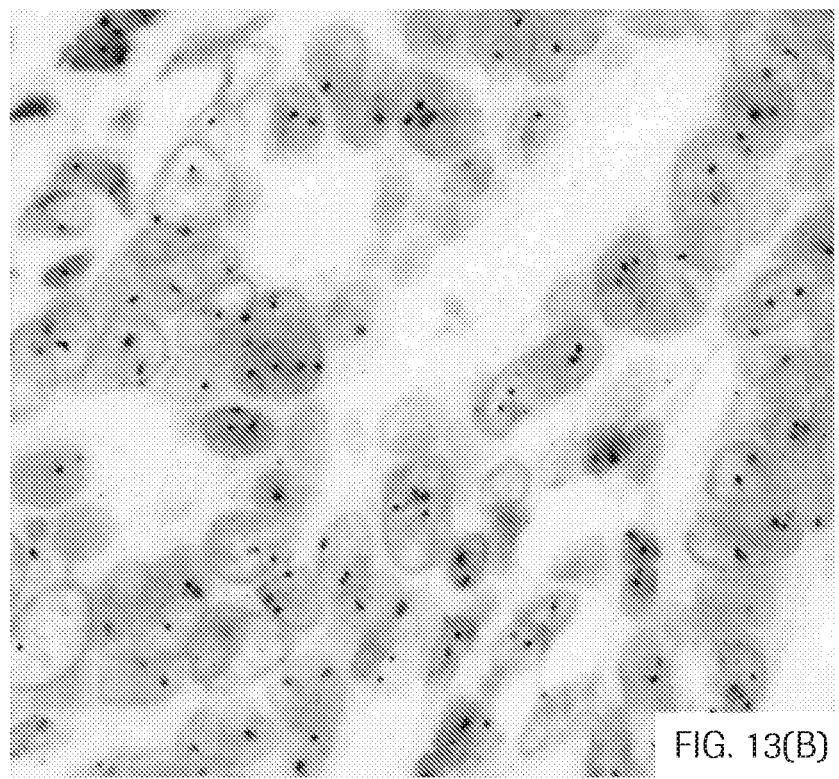

We chose 10 gastric tissue cases that were adequately stained by INFORM HER2 DUAL ISH DNA Probe with 6 hr hybridization. Duplicate slides for each case were stained with HER2/CHR17 Oligonucleotide Probe DISH with 1 hr hybridization. 18 slides stained by HER2/CHR17 Oligonucleotide Probe DISH passed (based on criteria intensity 2). For 2 cases, one of the duplicate slides had inadequate staining by HER2/CHR17 Oligonucleotide Probe DISH with 1 hr hybridization. FIG. 13(A)-(B) is an example of staining on Case #I-5189-C8a. HER2/CHR17 Oligonucleotide Probe DISH with 1 hr hybridization staining had HER2 intensity 3, coverage 80%, background 0; Chr17: Intensity 3.0, coverage 80%, background 0; while INFORM HER2 DUAL ISH DNA Probe with 6 hr hybridization staining had HER2 intensity 2.5, coverage 70%, background 0.5; CHR17 intensity 2.5, coverage 75%, background 0.

Example 2

Example 2 compares the p17H8 plasmid and the 42mer CHR17 oligonucleotide probe (and determines compatibility of the 42mer CHR17 oligonucleotide probe with the HER2 oligonucleotide probe).

p17H8 plasmid (PMA): The p17H8 plasmid probe contains this entire sequence. There are 16 repeats of the 166 bp sequence. This probe requires human placenta DNA because it gives weak signal from cross-hybridization to other chromosomes.

CHR17 (42mer) oligo: The 42mer CHR17 oligonucleotide probe (Ventana P/N: 90682, 10760, 95221) has good specificity for CHR17, does not require human placenta DNA, but the optimal hybridization conditions are different from the HER2 probe2 (INFORM FDA-approved product, made from PCR products). Its compatibility with the HER2 oligonucleotide probe is evaluated here.

Fixed assay conditions: StdCC2, P3 20 min, Denaturation 8 min, silver and red detection 8 min, H&E 8 min.

Conditions to be tested:
(1) Chr17 Oligonucleotide (42mer) concentrations: 0.35 ug/ml, 0.5 ug/ml, 0.75 ug/ml, 1.5 ug/ml and 3.0 ug/ml.
(2) Hybridization temperatures: 42° C., 44° C., and 46° C.
(3) Hybridization time: 1 hr, 2 hrs, and 6 hrs.

(4) Stringency wash temperatures: 54° C., 59° C., and 65° C.
(5) Formamide concentration in the hybridization buffer: 22.8% and 33.2%.

Figure 14A:
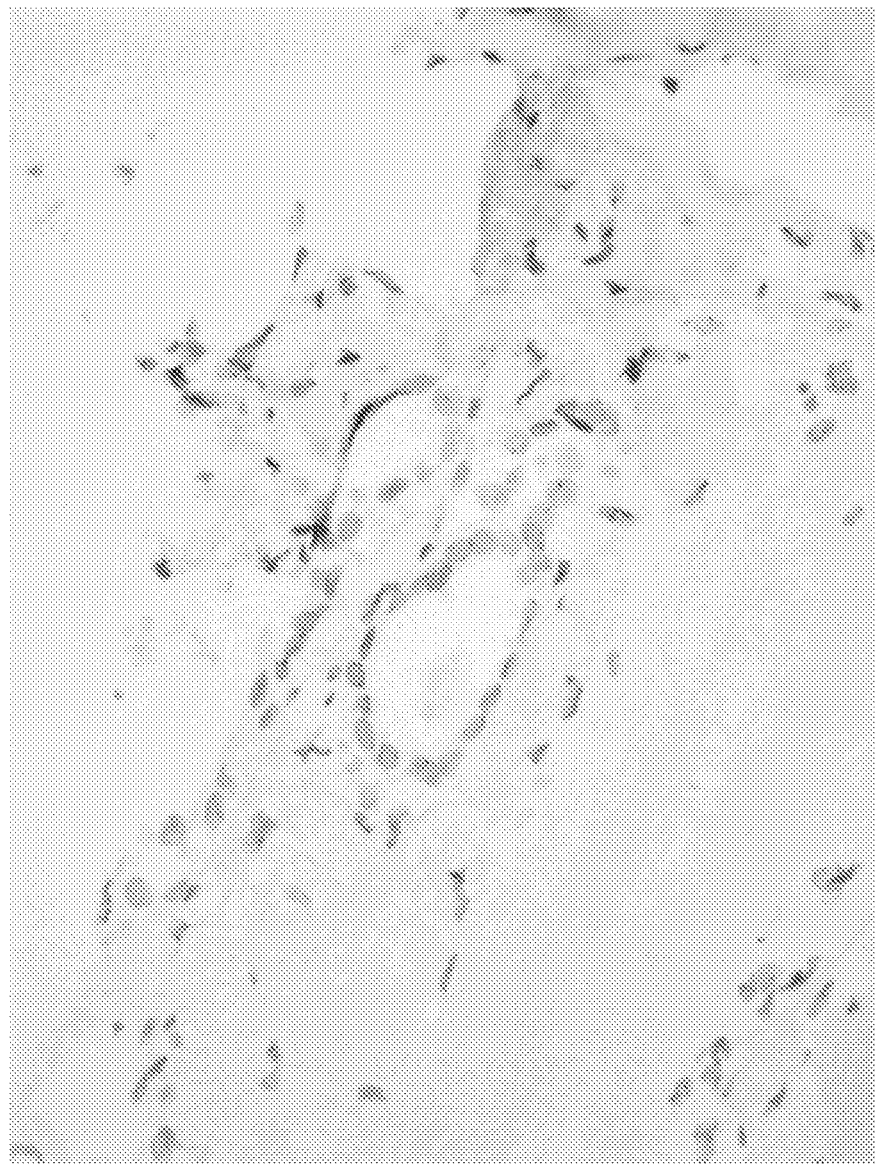
FIG. 14(A-D) are graphs showing (A) a weak signal for CHR17 using the 42-mer CHR17 oligonucleotide probe (B) that a 42-mer Chr17 oligonucleotide probe has weaker staining than the p17H8 probe at 33.2% formamide and increasing the concentration and hybridization time did not increase the signal with 33.2% formamide, (no 6 hr hybridization time point was performed as previous data suggested no difference between 1 to 6 hr hybridization time), (C) that 22.8% formamide gave a better signal for the 42-mer, but it was still weaker than PMA, and (D) that the stringency wash temperature for CHR17 oligonucleotide (42-mer) is not compatible with the HER2 oligonucleotide probes (68-72° C.).
Figure 14B:
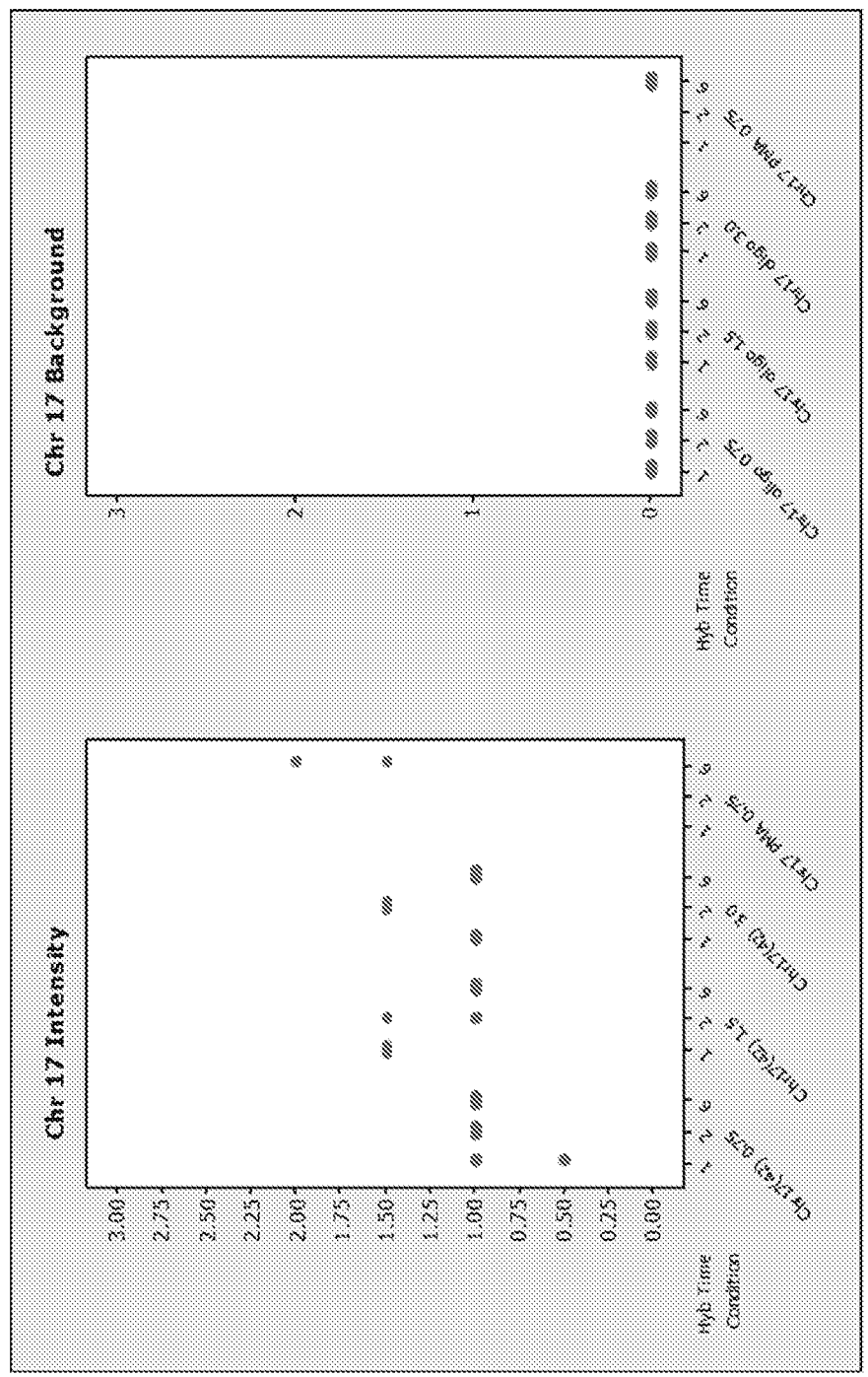
Figure 14C:
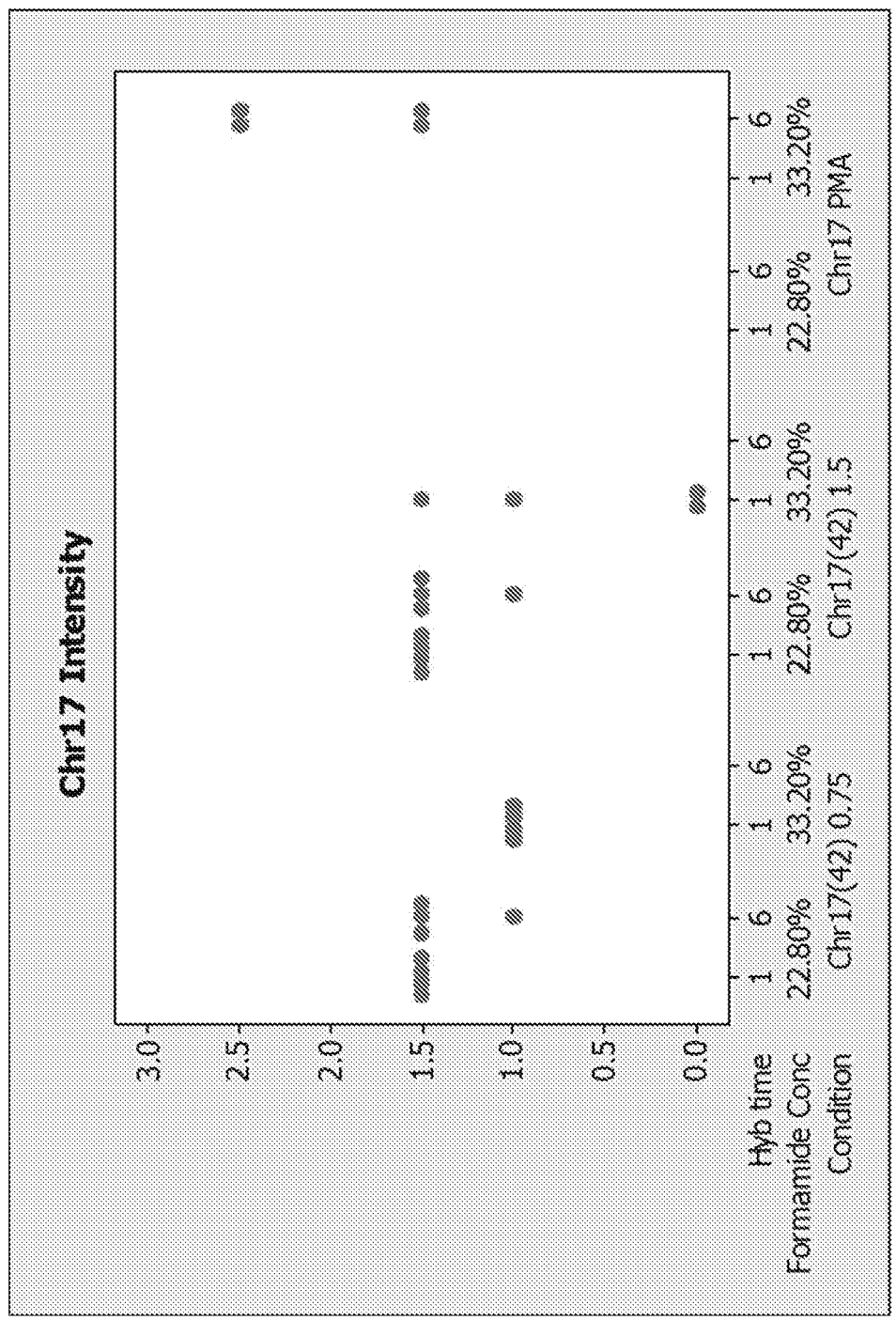
Figure 14D:
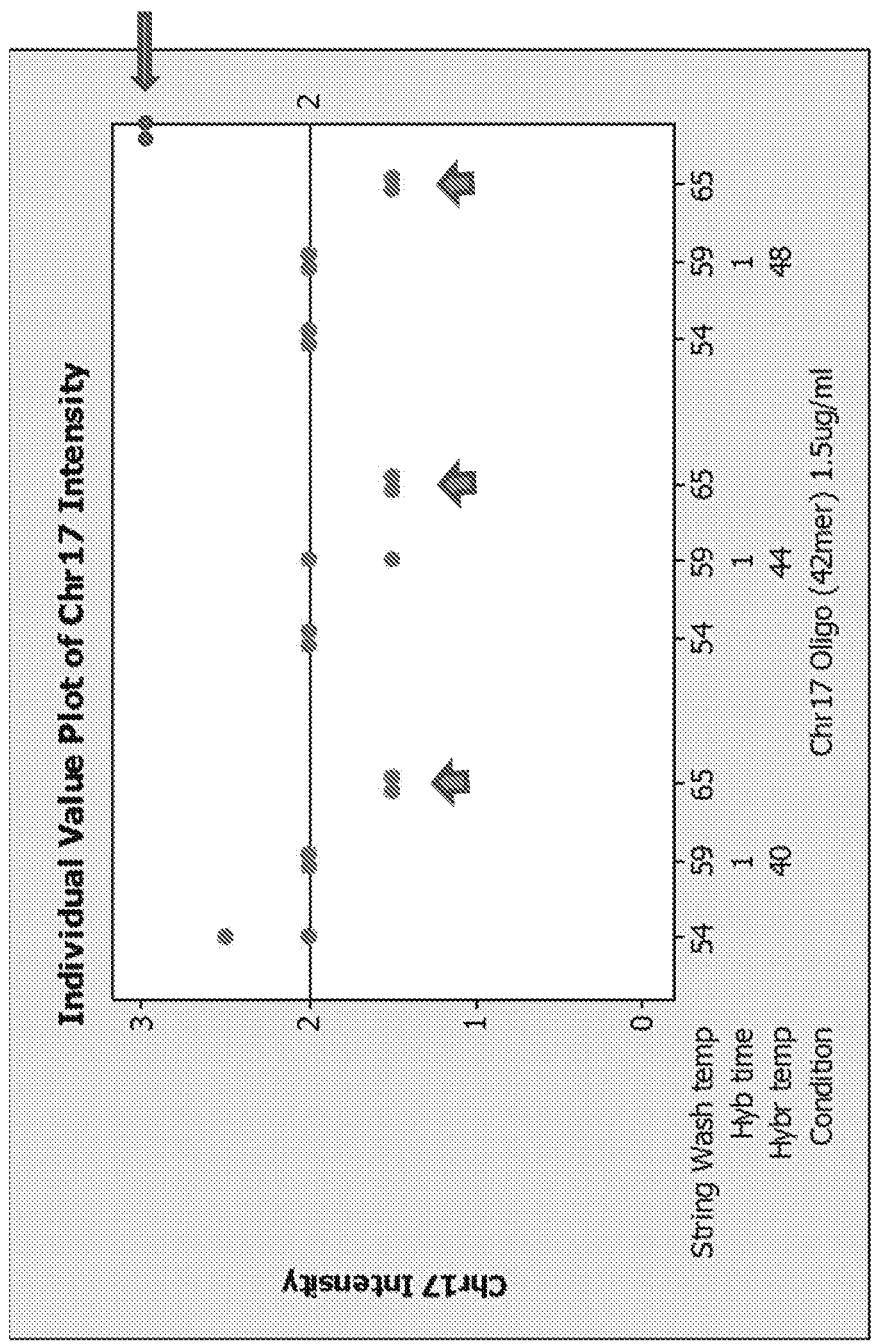
Figure 16A:
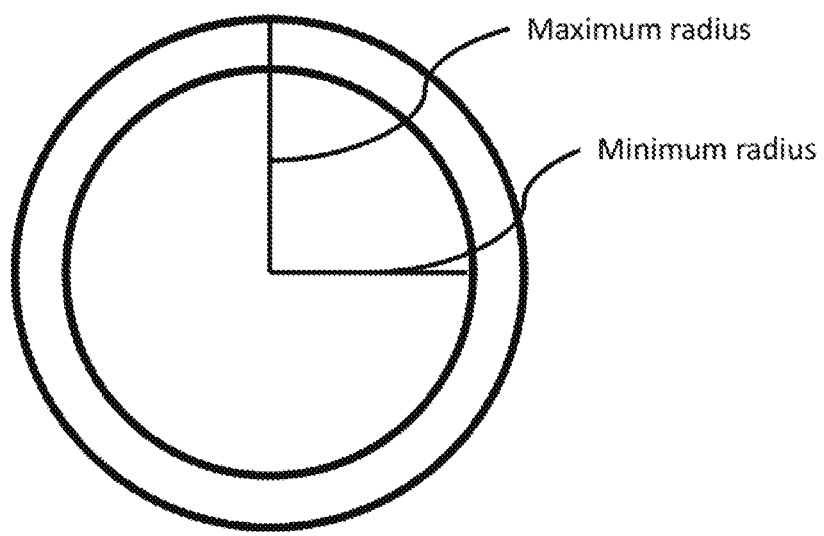
FIG. 16(A) shows the location of the maximum radius (or outer radius ($R_{out}$)) and the minimum radius (or inner radius ($R_{in}$)).
Figure 16B:
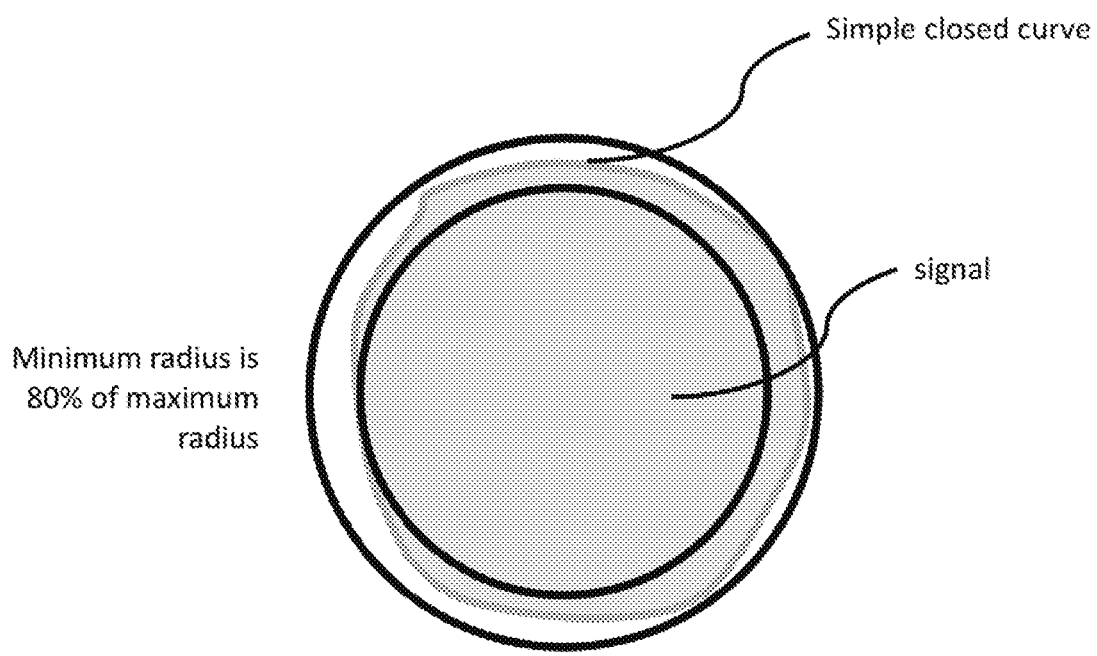
FIG. 16(A-D) shows examples of concentric circles and simple closed curves used for evaluating enumerable signals. The schematic helps describe a generally round shape as described herein. In particular.
Figure 16C:
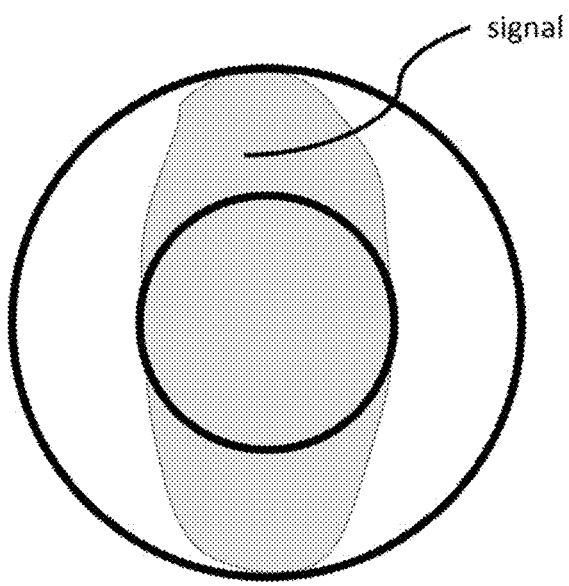
Figure 16D:
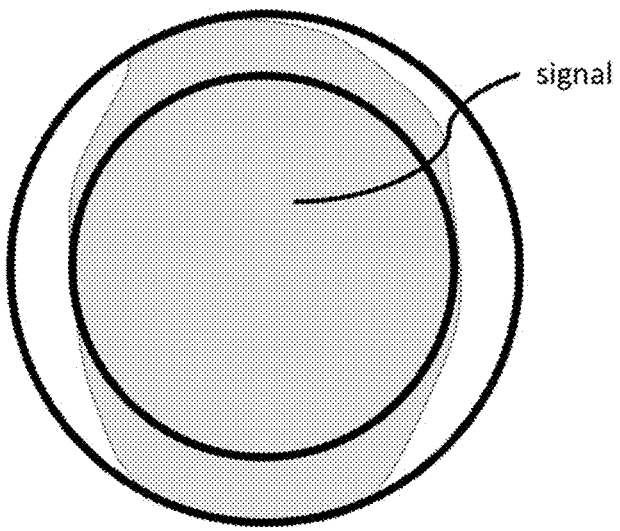

Results: FIG. 14(A) shows weak staining of the 42mer CHR17 oligonucleotide probe (Conditions were as follows: Chr17 Oligonucleotide (42mer) 0.75 ug/ml, 46° C. and 6 hrs Hyb (hybridization), 59° C. stringency wash, formamide concentration: 33.2%). FIG. 14(B) shows that Chr17 (42mer) staining is weaker than PMA at 33.2% formamide. Increasing the concentration and hybridization time did not increase the signal. (Conditions included a 59° C. stringency wash, 33.2% formamide). FIG. 14(C) shows that 22.8% formamide gave a better CHR17 signal, but it was still weaker than PMA. Increasing the concentration and hybridization time did not increase the signal intensity. No background observed with 59° C. stringency wash. However, 22.8% formamide is not optimal for HER2 Oligonucleotide ISH (not compatible). FIG. 14(D) shows that the stringency wash temperature for CHR17 oligonucleotide (42mer) is not compatible with the HER2 oligonucleotide (68-72° C.); a 65° C. stringency temperature reduced CHR17 signals.

In summary, the 42mer CHR17 Oligonucleotide probe generates specific signal, and 0.75 and 1.5 ug/ml for 1 hr offer the best staining. But, the staining is weaker than PMA control. Increasing the concentration and hybridization time did not improve signal intensity. The hybridization assay conditions for the 42mer CHR17 oligonucleotide probe are not compatible with that of HER2 oligonucleotide probe: the optimal range of stringency wash temperatures for HER2 oligonucleotide is 68-72° C.; and the drop on staining intensity of CHR17 oligonucleotide (42mer) becomes obvious when the temp goes up to 65° C.

All publications, patent applications, patents, and other references mentioned herein are incorporated by reference in their entirety for all purposes. In case of conflict, the present specification, including explanations of terms, will control. The following other patents are herein incorporated by reference in their entirety: U.S. Pat. Nos. 7,807,356; 8,445,206.

While a number of exemplary aspects and embodiments have been discussed above, those of skill in the art will recognize certain modifications, permutations, additions and sub-combinations thereof as being present in the disclosure. It is therefore intended that the following appended claims and claims hereafter introduced are interpreted to include all such modifications, permutations, additions and sub-combinations as are within their true spirit and scope.

TABLE 8

| | | Sequences |
|---|---|---|
| SEQ. ID. NO: 1 | | TCTCGTCTCGGCCCCCGACCTGCGTCCTGGGCCCGCAGGGGAGTCCTGCC CCATGCTCCCGGGCGGGGCCGCCCTGTGCCCT |
| SEQ. ID. NO: 2 | | TATTTTTATTTTAATTCGTTGGAAACGGGATAATTTCAGCTGACTAAACAGA AGCAGTCTCAGAATCTTCTTTGTGATGTTTGCATTCAAA |
| SEQ ID. NO: 3 | CHR17_M1.1 | AATTCGTTGGAAACGGGATAATTTCAGCTGACTAAACAGAAGCAGTCTCAGA ATCTTCTTTGTGATGTTTGCATTCAAA |
| SEQ ID. NO: 4 | CHR17_M2.1 | CTTCGTTCGAAACGGGTATATCTTCACATGCCATCTAGACAGAAGCATCCTCA GAAGCTTCTCTGTGATGACTGCATTC |
| SEQ ID. NO: 5 | CHR17_M2.2 | TGAACTCTCCTTTTGAGAGCGCAGTTTTGAAACTCTCTTTCTGTGGCATCTGCA AGGGGACATGTAGACCTCTTTGAAG |
| SEQ ID. NO: 6 | CHR17_M3.1 | TTTCGTTGGAAACGGAATCATCTTCACATAAAAACTACACAGATGCATTCTCA GGAACTTTTTGGTGATGTTTGTATTC |
| SEQ ID. NO: 7 | CHR17_M5.1 | CCTATGGTAGTAAAGGGAATAGCTTCATAGAAAAACTAGACAGAAGCATTCT CAGAAAATACTTTGTGATGATTGAGTTTAAC |
| SEQ ID. NO: 8 | CHR17_M5.2 | CACAGAGCTGAACATTCCTTTGGATGGAGCAGGTTTGAGACACTCTTTTTGTA CAATCTACAAGTGGATATTTGGACCTCTCTGAGG |
| SEQ ID. NO: 9 | CHR17_M8.2 | GTTTCACATTGCTTTTCATAGAGTAGTTCTGAAACATGCTTTTCGTAGTGTCTAC AAGTGGACATTTGGAG |
| SEQ ID. NO: 10 | CHR17_M9.1 | CCTGTGGTGGAAAACGAATTATCGTCACGTAAAAACTAGAGAGAAGCATTGT CAGAAA |
| SEQ ID. NO: 11 | CHR17_M9.2 | TGCATTCAACTCACAGAGTTGAAGGTTCCTTTTCAAAGAGCAGTTTCCAATCA CTCTTTGTGTGG |
| SEQ ID. NO: 12 | CHR17_M11.2 | CATTCCCTTTGACAGAGCAGTTTGGAAACTCTCTTTGTGTAGAATCTGCAAGT GGAGATATGGACCGCTTT |
| SEQ ID. NO: 13 | CHR17_M12.1 | CCTATGGTAGTAAAGGAAATAGCTTCATATAAAAGCTAGACAGTAGCATTCA CAGAAAACTCTTGGTGACGACTGAGTTT |
| SEQ ID. NO: 14 | CHR17_M13.1 | ATTTCGTTGGAAACGGGATAAACCGCACAGAACTAAACAGAAGCATTCTCAG AACCTTCTTCGTGATGTTTGCATTCAAC |
| SEQ ID. NO: 15 | CHR17_M16.1 | CGTAGTAAAGGAAATAACTTCCTATAAAAAGAAGACAGAAGCMCTCAGAA AATTCTTTGGGATGATTGAGTTGAACTC |
| SEQ ID. NO: 16 | CHR17_M16.2 | ACAGAGCTGAGCATTCCTTGCGATGTAGCAGTTTAGAAACACACTTTCTGCA GAATCTGCAATTGCATATTTGGACCTT |

Additional Exemplary Embodiments

The following additional embodiments are also specifically disclosed. This is not an exhaustive list.

1. A system for in situ detection of a control region of human chromosome 17, said system comprising: a set of two or more single-stranded control probes specific for X distinct monomers of an alpha satellite control region of human chromosome 17, wherein X=2-14, the control probes are each labeled with at least one first label.

2. The system of embodiment 1, wherein $X \geq 4$.

3. The system of embodiment 1, wherein $X \geq 6$.

4. The system of embodiment 1, wherein $X \geq 8$.

5. The system of embodiment 1, wherein $X \geq 10$.

6. The system of embodiment 1, wherein the control probes, when applied to a sample, are configured to achieve at least two enumerable signals per cell with a staining intensity of $\geq 2$ and staining coverage of $\geq 50\%$ of the number of total nuclei within 3 hours of hybridization.

7. The system of embodiment 1, wherein the control probes can achieve an enumerable signal when hybridized to chromosome 17, each enumerable signal having a generally round shape, wherein a round shape is a shape defined by a simple closed curve fitting within a first region, the first region being an area on and between an inner concentric circle and an outer concentric circle, the inner concentric circle having an inner radius ($R_{in}$) and the outer concentric circle having a outer radius ($R_{out}$) wherein $R_{in}$ is $\geq 50\%$ of $R_{out}$, and the simple closed curve having a radius $R_{simple}$, wherein $R_{in} \leq R_{simple} \leq R_{out}$, and wherein the simple closed curve is a connected curve that does not cross itself and ends at the same point where it begins.

8. The system of embodiment 1, wherein each probe comprises: a sequence selected from the group consisting of SEQ ID NOs: 3-16; or a sequence selected from the group consisting of a truncated version of SEQ ID NOs: 3-16, the truncated version being at least 40 contiguous bp of said SEQ ID NOs:3-16; or a sequence selected from the group consisting of a sequence that has at least 70% sequence identity to one of SEQ ID NOs: 3-16, or complements thereof.

9. The system of embodiment 1, wherein each probe comprises: a sequence selected from the group consisting of SEQ ID NOs: 3-16; or a sequence selected from the group consisting of a truncated version of SEQ ID NOs: 3-16, the truncated version being at least 40 contiguous bp of said SEQ ID NOs:3-16; or a sequence selected from the group consisting of a sequence that has at least 80% sequence identity to one of SEQ ID NOs: 3-16; or complements thereof.

10. The system of embodiment, wherein the probes are configured to hybridize uniquely and specifically to a portion of the control region of human chromosome 17 so that other chromosomes or portions thereof are not evidently labeled.

11. The system of embodiment 1, wherein the probes are configured to hybridize uniquely and specifically to a portion of the control region of human chromosome 17 so that other chromosomes or portions thereof are not evidently labeled without the influence of blocking DNA.

12. The system of embodiment, wherein the control probes each comprise between 50 to 100 nucleotides.

13. The system of embodiment 1, wherein the probes target between 2 and 14 distinct portions within the control region.

14. The system of embodiment 1, wherein the probes target between 4 and 14 distinct portions within the control region.

15. The system of embodiment 1, wherein the probes target between 6 and 14 distinct portions within the control region.

16. The system of embodiment 1, wherein the probes target between 8 and 14 distinct portions within the control region.

17. The system of embodiment 1, wherein the probes target between 10 and 14 distinct portions within the control region.

18. The system of embodiment 1, wherein the control probes are each labeled with at least 2, at least 3, at least 4, or at least 5 first labels.

19. The system of embodiment 1, wherein the at least one first label comprises a hapten.

20. The system of embodiment 1 further comprising a target probe specific to a target region of human chromosome 17, wherein the target probe is labeled with at least one second label.

21. The system of embodiment 20, wherein the target probe is specific to a target region near or around the HER2 gene locus.

22. The system of embodiment 20, wherein the target probe is specific to a region between nucleotides 35,027,979 and 35,355,516 of human chromosome 17.

23. The system of embodiment 1 further comprising an ISH staining instrument, the instrument being configured to contact the control probe to a tissue sample.

24. A kit comprising a vessel containing a system according embodiment 1.

25. A kit comprising a set of two or more single-stranded probes, each probe comprising a sequence selected from SEQ ID NOs: 3-16.

26. A slide comprising a plurality of nuclei chromogenically stained for chromosome 17, wherein more than 50% of the nuclei have enumerable signals for chromosome 17, each enumerable signal being a generally round shape, the round shape being a shape defined by a simple closed curve fitting within a first region, the first region being an area on and between an inner concentric circle and an outer concentric circle, the inner concentric circle having an inner radius ($R_{inn}$) and the outer concentric circle having a outer radius ($R_{out}$), wherein is $\geq 50\%$ of $R_{out}$, and the simple closed curve has a radius $R_{simple}$ wherein $R_{in} \leq R_{simple} \leq R_{out}$, and wherein the simple closed curve is a connected curve that does not cross itself and ends at the same point where it begins.

27. The slide of embodiment 26, wherein the slide is made using a system according to embodiment 1.

28. The slide of embodiment 26, wherein more than 60% of the nuclei have enumerable chromosome signals.

29. The slide of embodiment 26, wherein more than 70% of the nuclei have enumerable chromosome signals.

30. The slide of embodiment 26, wherein $R_{in}$ is $\geq 60\%$ of $R_{out}$.

31. The slide of embodiment 26, wherein $R_{in}$ is $\geq 75\%$ of $R_{out}$.

32. The slide of embodiment 26, wherein $R_{in}$ is $\geq 90\%$ of $R_{out}$.

33. The slide of embodiment 26, wherein the outer radius ($R_{out}$) is between about 0.25 to 0.675 μm.

34. The slide of embodiment 26, wherein the outer radius ($R_{out}$) is between about 0.2 to 0.75 μm.

35. The slide of embodiment 26, wherein the outer radius ($R_{out}$) is between about 0.15 to 1 μm.

36. The slide of embodiment 26, wherein the average radius ($R_{simple}$) of the enumerable signals is between about 0.2 to 0.75 μm.

37. The slide of embodiment 26, wherein the average radius ($R_{simple}$) of the enumerable signals has a standard deviation of less than 0.5 μm.

38. The slide of embodiment 26, wherein the average radius ($R_{simple}$) of the enumerable signals has a standard deviation of less than 0.25 μm.

39. A method for in situ hybridization comprising: contacting a tissue sample with a set of two or more single-stranded control probes specific for X distinct monomers of an alpha satellite control region of human chromosome 17, wherein X=2-14, and wherein the control probes are each labeled with at least one first label; hybridizing the set of control probes to the control region under conditions for a period of time less than about 3 hours; rinsing the sample to remove unbound probe; and staining the sample to detect hybridized probes so that at least two signals per cell with a staining intensity of ≥2 and staining coverage of ≥50% of the number of total nuclei are detectable.

40. The method of embodiment 39, wherein the method is for bright-field in situ hybridization.

41. The method of embodiment 39, wherein the control probes are hybridized to the control region for a period of time less than about 2 hours.

42 The method of embodiment 39, wherein the control probes are hybridized to the control region for a period of time less than about 1 hour.

43. The method of embodiment 39 further comprising contacting the tissue sample with a target probe specific to a region of chromosome 17, wherein the target probe is a single-stranded oligonucleotide probe labeled with at least one second label.

44. The method of embodiment 43, wherein the target probe is specific to a target region near or around the HER2 gene locus of chromosome 17.

45. The method of embodiment 44, wherein the target probe is specific to a region between nucleotides 178,640,071 and 179,399,807 of human chromosome 17.

46. The method of embodiment 39 further comprising applying chromogenic detection reagents that recognize the first label and amplify the signal associated with said first label.

47. The method of embodiment 39, wherein the tissue sample is a formalin-fixed paraffin-embedded (FFPE) tissue sample.

48. The method of any of embodiment 39, wherein the method is free from the use of blocking DNA.

49. The method of embodiment 39, wherein an amount of blocking DNA is used.

50. A method for in situ hybridization of a tissue sample, the method comprising contacting the tissue sample with a system according embodiment 1.

51. A method for dual bright-field in situ hybridization comprising: contacting a tissue sample with a set of two or more single-stranded control probes specific for X distinct monomers of an alpha satellite control region of human chromosome 17, wherein X=2-14, the control probes each being labeled with at least one first label; contacting the tissue sample with a single-stranded target probe specific for a target region near or around the HER2 gene locus of human chromosome 17, the target probe being labeled with at least one second label; hybridizing the probes under conditions for a period of time less than about 3 hours; rinsing the sample to remove unbound probe; and staining the sample to detect hybridized probes.

52. The method of embodiment 51, wherein the sample is stained with a first chromogenic color for detecting the control probes and a second distinct chromogenic color for detecting the target probe specific for a target region near or around the HER2 gene locus of human chromosome 17.

53. The method of embodiment 51, wherein the probes are hybridized under conditions for a period of time less than about 2 hours.

54. The method of embodiment 51, wherein the probes are hybridized under conditions for a period of time less than about 1 hour.

55. The method of embodiment 51 further comprising applying chromogenic detection reagents that recognize the first label and amplify the signal associated with said first label.

56. The method of embodiment 51, wherein the tissue sample is a formalin-fixed paraffin-embedded (FFPE) tissue sample.

57. The method of embodiment 51, wherein the method is free from the use of blocking DNA.

58. The method of embodiment 51, wherein an amount of blocking DNA is used.

59. A method for bright-field chromogenic in situ hybridization without the use of blocking DNA, said method comprising: contacting a tissue sample with a set of two or more single-stranded control probes specific for X distinct monomers of an alpha satellite control region of human chromosome 17, wherein X=2-14; hybridizing the control probes to the control region of human chromosome 17; rinsing the sample to remove unbound probe; and staining the sample with a first chromogen to detect hybridized control probes; wherein no blocking DNA is used in any of the above steps.

60. A method for obtaining two bright-field chromogenic in situ hybridization signals per cell, said method comprising: contacting a tissue sample containing a plurality of cells with a set of two or more single-stranded control probes specific for X distinct monomers of an alpha satellite control region of human chromosome 17, wherein X=2-14, and the probes are selected so as to not evidently bind non-specifically in the absence of blocking DNA; hybridizing the control probes to the control region of said human chromosome; rinsing the sample to remove unbound probe; and staining the sample with a chromogenic reagent to detect the presence of hybridized probes, wherein the probes are configured to generate two bright-field chromogenic in situ hybridization signals per cell.

61. The method of embodiment 60, wherein the control probes are each labeled with at least one first label.

62. A method for bright-field chromogenic in situ hybridization comprising: contacting a tissue sample with a set of two or more single-stranded control probes specific for X distinct monomers of an alpha satellite control region of human chromosome 17, wherein X=2-14; hybridizing the control probes to the control region of said human chromosome; rinsing the sample to remove unbound probe; and staining the sample with a first chromogen to detect hybridized control probes; wherein an amount of blocking DNA is used in one of the above steps, the amount of blocking DNA being sufficient to block out no more than 50% of the non-specific binding.

63. The method of embodiment 62, wherein the control probes are each labeled with at least one first label.

64. The method of embodiment 62, wherein the amount of blocking DNA is between about 1 pg/ml to 1 mg/ml.

65. A method of in situ hybridization, the method comprising: contacting a tissue sample with a set of two or more single-stranded control probes specific for X distinct monomers of an alpha satellite control region of human chromosome 17, wherein X=2-14, wherein the control probes are labeled with at least one first label, and wherein the control probes when applied to the tissue sample are configured to achieve two signals per cell with a staining intensity of ≥2 and staining coverage of ≥50% of the number of total nuclei within 3 hours of hybridization; hybridizing the control probes to the control region of said human chromosome under conditions for a period of time less than 3 hours; rinsing the sample to remove unbound probe; and staining the sample to detect the presence of hybridized probes;

wherein more than 50% of the nuclei of the tissue sample have enumerable signals for human chromosome 17, each enumerable signal being a generally round shape, the round shape being a shape defined by a simple closed curve fitting within a first region, the first region being an area on and between an inner concentric circle and an outer concentric circle, the inner concentric circle having an inner radius ($R_{in}$) and the outer concentric circle having a outer radius ($R_{out}$), wherein $R_{in}$ is ≥50% of $R_{out}$, and the simple closed curve having a radius $R_{simple}$ wherein $R_{in} \leq R_{simple} \leq R_{out}$.

66. The method of embodiment 65, wherein background signals being signals that show more than 2 enumerable signals per nuclei, are not observed in >80% of cells of the tissue sample.

67. The method of embodiment 65, wherein background signals have a staining intensity of 0 or 1.

68. The method of embodiment 65, wherein the tissue sample is contacted with a system according to embodiment 1.

69. The method of embodiment 65, wherein more than 60% of the nuclei have enumerable chromosome signals.

70. The method of embodiment 65, wherein more than 70% of the nuclei have enumerable chromosome signals.

71. The method of embodiment 65, wherein $R_{in}$ is ≥60% of $R_{out}$.

72. The method of embodiment 65, wherein $R_{in}$ is ≥75% of $R_{out}$.

73. The method of embodiment 65, wherein $R_{in}$ is ≥90% of $R_{out}$.

74. The method of embodiment 65, wherein the outer radius ($R_{out}$) is between about 0.25 to 0.675 um.

75. A method of scoring for a chromosome for HER2 gene copy number, said method comprising: obtaining a tissue sample having undergone in situ hybridization according embodiment 39, wherein a control probe specific for human chromosome 17 and a target probe specific for HER2 are used; identifying an area of neoplastic nuclei with most copy numbers; and counting enumerable signals for HER2 signal in at least 20 nuclei; and calculating the ratio of HER2 signal to chromosome 17 signal (HER2/CHR17 ratio).

76. The method of embodiment 75, wherein if the HER2/CHR17 ratio falls within 1.8-2.2, then enumerable signals are counted in 20 additional nuclei and the HER2/CHR17 ratio is calculated from the 40 total nuclei.

77. The method of embodiment 75, wherein a HER2/CHR17 ratio of less than 2.0 is considered non-amplified and a HER2/CHR17 ratio of greater than or equal to 2.0 is considered amplified.

78. The method of embodiment 75 further comprising calculating the average number of HER2 copies per nuclei.

79. A probe for use in a bright-field chromogenic in situ hybridization, the probe comprising a set of two or more single-stranded control probes specific for X distinct monomers of an alpha satellite control region of chromosome 17, wherein X=2-14, wherein the control probes are each labeled with at least one first label, and wherein the control probes are selected so as to not evidently bind non-specifically in the absence of blocking DNA.

80. A probe comprising a plurality of single-stranded oligonucleotide control probes, each control probe comprising: a sequence selected from the group consisting of SEQ ID NOs: 3-16; or a sequence selected from the group consisting of a truncated version of SEQ ID NOs: 3-16, the truncated version being at least 40 contiguous bp of said SEQ ID NOs:3-16; or a sequence selected from the group consisting of a sequence that has at least 70% sequence identity to one of SEQ ID NOs: 3-16.

The invention claimed is:

1. A system for in situ detection of a control region of human chromosome 17, said system comprising:
a set of two or more single-stranded control probes specific for X distinct monomers of an alpha satellite control region of human chromosome 17, wherein X=2-14, the control probes are each labeled with at least one first label, wherein the control probes, when applied to a sample, are configured to achieve at least two enumerable signals per cell with a staining intensity of ≥2 and staining coverage of ≥50% of the number of total nuclei within 3 hours of hybridization.

2. A system for in situ detection of a control region of human chromosome 17, said system comprising:
a set of two or more single-stranded control probes specific for X distinct monomers of an alpha satellite control region of human chromosome 17, wherein X=2-14, the control probes are each labeled with at least one first label, wherein the control probes can achieve an enumerable signal when hybridized to chromosome 17, each enumerable signal having a generally round shape, wherein a round shape is a shape defined by a simple closed curve fitting within a first region, the first region being an area on and between an inner concentric circle and an outer concentric circle, the inner concentric circle having an inner radius ($R_{in}$) and the outer concentric circle having an outer radius ($R_{out}$) wherein $R_{in}$ is ≥ 50% of $R_{out}$, and the simple closed curve having a radius $R_{simple}$, wherein $R_{in} \leq R_{simple} \leq R_{out}$, and wherein the simple closed curve is a connected curve that does not cross itself and ends at the same point where it begins.

3. The system of claim 1, wherein each probe comprises:
a sequence selected from the group consisting of SEQ ID NOs: 3-16; or
a sequence selected from the group consisting of a truncated version of SEQ ID NOs: 3-16, the truncated version being at least 40 contiguous bp of said SEQ ID NOs:3-16; or
a sequence selected from the group consisting of a sequence that has at least 70% sequence identity to one of SEQ ID NOs: 3-16, or
complements thereof.

4. The system of claim 1, further comprising a target probe specific to a target region of human chromosome 17, wherein the target probe is labeled with at least one second label.

5. The system of claim 4, wherein the target probe is specific to a target region near or around the HER2 gene locus.

6. The system of claim 4, wherein the target probe is specific to a region between nucleotides 35,027,979 and 35,355,516 of human chromosome 17.

7. A probe for use in a bright-field chromogenic in situ hybridization, the probe comprising a set of two or more single-stranded control probes specific for X distinct monomers of an alpha satellite control region of chromosome 17, wherein X=2-14, wherein the control probes are each labeled with at least one first label, wherein each control probe has a length from 40 to 120 nucleotides, and wherein the control probes are selected so as to not evidently bind non-specifically in the absence of blocking DNA.

8. A probe comprising a plurality of single-stranded oligonucleotide control probes, each control probe comprising:
a sequence selected from the group consisting of SEQ ID NOs: 3-16; or a sequence selected from the group consisting of a truncated version of SEQ ID NOs: 3-16, the truncated version being at least 40 contiguous bp of said SEQ ID NOs:3-16; or
a sequence selected from the group-consisting of a sequence that has at least 70% sequence identity to one of SEQ ID NOs: 3-16; and
wherein each control probe has a length from 40 to 120 nucleotides.

9. The system of claim 2, wherein each probe comprises:
a sequence selected from the group consisting of SEQ ID NOs: 3-16; or
a sequence selected from the group consisting of a truncated version of SEQ ID NOs: 3-16, the truncated version being at least 40 contiguous bp of said SEQ ID NOs:3-16; or
a sequence selected from the group consisting of a sequence that has at least 70% sequence identity to one of SEQ ID NOs: 3-16, or
complements thereof.

10. The system of claim 2, further comprising a target probe specific to a target region of human chromosome 17, wherein the target probe is labeled with at least one second label.

11. The system of claim 10, wherein the target probe is specific to a target region near or around the HER2 gene locus.

12. The system of claim 10, wherein the target probe is specific to a region between nucleotides 35,027,979 and 35,355,516 of human chromosome 17.

* * * * *